US008288406B2

(12) United States Patent  (10) Patent No.: US 8,288,406 B2
Frormann et al.  (45) Date of Patent: Oct. 16, 2012

(54) HYDROXYMETHYLCYCLOHEXYLAMINES

(75) Inventors: Sven Frormann, Aachen (DE); Saskia Zemolka, Aachen (DE); Klaus Linz, Wachtberg (DE); Werner Englberger, Stolberg (DE); Fritz Theil, Berlin (DE)

(73) Assignee: Gruenenthal GmbH, Aachen (DE)

( * ) Notice: Subject to any disclaimer, the term of this patent is extended or adjusted under 35 U.S.C. 154(b) by 16 days.

(21) Appl. No.: 12/887,997

(22) Filed: Sep. 22, 2010

(65) Prior Publication Data

US 2011/0059999 A1   Mar. 10, 2011

Related U.S. Application Data

(63) Continuation of application No. PCT/EP2009/002184, filed on Mar. 25, 2009.

(30) Foreign Application Priority Data

Mar. 27, 2008 (EP) .................... 08005809

(51) Int. Cl.
A61K 31/44 (2006.01)
C07D 209/44 (2006.01)
(52) U.S. Cl. .......... 514/292; 514/438; 514/416; 546/87; 548/482
(58) Field of Classification Search .......... 514/292, 514/438, 416; 546/87; 548/482
See application file for complete search history.

(56) References Cited

U.S. PATENT DOCUMENTS

| 3,328,412 | A | 6/1967 | Atkinson et al. |
| 4,065,573 | A | 12/1977 | Lednicer |
| 4,115,589 | A | 9/1978 | Lednicer |
| 4,291,039 | A | 9/1981 | Van Dyke, Jr. et al. |
| 4,366,172 | A | 12/1982 | Lednicer |
| 4,575,508 | A | 3/1986 | Steiner et al. |
| 5,328,905 | A | 7/1994 | Hamminga et al. |
| 5,631,265 | A | 5/1997 | Audia et al. |
| 5,760,051 | A | 6/1998 | Audia et al. |
| 5,869,691 | A | 2/1999 | Audia et al. |
| 7,173,045 | B2 | 2/2007 | Sundermann et al. |
| 7,183,436 | B2 | 2/2007 | Sundermann et al. |
| 7,211,694 | B2 | 5/2007 | Sundermann et al. |
| 7,232,847 | B2 | 6/2007 | Sundermann et al. |
| 7,241,802 | B2 | 7/2007 | Sundermann et al. |
| 7,288,560 | B2 | 10/2007 | Hinze et al. |
| 7,332,519 | B2 | 2/2008 | Hinze et al. |
| 7,348,354 | B2 | 3/2008 | Hinze et al. |
| 7,439,394 | B2 | 10/2008 | Sundermann et al. |
| 7,476,763 | B2 | 1/2009 | Sundermann et al. |
| 7,485,634 | B2 | 2/2009 | Martin et al. |
| 7,507,758 | B2 | 3/2009 | Sundermann et al. |
| 7,547,707 | B2 | 6/2009 | Hinze et al. |
| 7,589,113 | B2 | 9/2009 | Merla et al. |
| 7,595,311 | B2 | 9/2009 | Busch et al. |
| 7,608,619 | B2 | 10/2009 | Merla et al. |
| 7,728,028 | B2 | 6/2010 | Merla et al. |
| 7,759,385 | B2 | 7/2010 | Hinze et al. |
| 7,776,848 | B2 | 8/2010 | Sundermann et al. |
| 7,786,328 | B2 | 8/2010 | Sundermann et al. |
| 7,799,931 | B2 | 9/2010 | Hinze et al. |
| 7,960,404 | B2 | 6/2011 | Schunk et al. |
| 7,977,370 | B2 | 7/2011 | Zemolka et al. |
| 8,017,630 | B2 | 9/2011 | Hinze et al. |
| 8,034,936 | B2 | 10/2011 | Friderichs et al. |
| 8,053,576 | B2 | 11/2011 | Hinze et al. |
| 8,058,475 | B2 | 11/2011 | Oberboersch et al. |
| 8,088,763 | B2 | 1/2012 | Sundermann et al. |
| 8,093,272 | B2 | 1/2012 | Sundermann et al. |
| 8,124,788 | B2 | 2/2012 | Merla et al. |
| 8,133,992 | B2 | 3/2012 | Martin et al. |
| 8,138,187 | B2 | 3/2012 | Zemolka et al. |
| 8,143,257 | B2 | 3/2012 | Choi et al. |
| 2003/0236250 | A1 | 12/2003 | Pineiro et al. |
| 2004/0023947 | A1 | 2/2004 | Martin et al. |
| 2004/0162287 | A1 | 8/2004 | Sundermann et al. |
| 2005/0054634 | A1 | 3/2005 | Busch et al. |
| 2005/0192333 | A1 | 9/2005 | Hinze et al. |
| 2005/0267107 | A1 | 12/2005 | Sundermann et al. |
| 2006/0004034 | A1 | 1/2006 | Hinze et al. |
| 2006/0235012 | A1 | 10/2006 | Davidson et al. |
| 2007/0149557 | A1 | 6/2007 | Collins et al. |
| 2008/0125475 | A1 | 5/2008 | Linz et al. |
| 2008/0221141 | A1 | 9/2008 | Friderich et al. |
| 2008/0261956 | A1 | 10/2008 | Choi et al. |

(Continued)

FOREIGN PATENT DOCUMENTS

| AR | 071066 | 5/2010 |
| AR | 071067 | 5/2010 |
| AR | 071068 | 5/2010 |
| AR | 073841 | 12/2010 |
| AR | 074615 | 2/2011 |
| AU | 2009228637 | 10/2009 |
| AU | 2009228642 | 10/2009 |
| AU | 2009228643 | 10/2009 |
| AU | 2009228645 | 10/2009 |
| AU | 2009228647 | 10/2009 |

(Continued)

OTHER PUBLICATIONS

Abdulla et al, "Axotomy Reduces the Effect of Analgesic Opioids Yet Increases the Effect of Nociceptin on Dorsal Root Ganglion Neurons"; The Journal of Neurosciene, Dec. 1, 1998, 18 (23), pp. 9685-9694.

Manabe et al, "Facilitation of long-term potentiation and memory in mice lacking nociceptin receptors"; Nature, vol. 394, Aug. 6, 1998, pp. 577-581.

Nishi et al, "Unrestrained nociceptive response and disregulation of hearing ability in mice lacking the nociceptin/orphaninFQ receptor"; The EMBO Journal, vol. 16, No. 8, 1997, pp. 1858-1864.

(Continued)

Primary Examiner — Rei-tsang Shiao

(74) Attorney, Agent, or Firm — Norris McLaughlin & Marcus, PA

(57) ABSTRACT

The invention relates to compounds which have an affinity for the μ opioid receptor and the ORL1 receptor, processes for the preparation thereof, medicaments containing these compounds and the use of these compounds for the preparation of medicaments.

10 Claims, No Drawings

U.S. PATENT DOCUMENTS

| | | |
|---|---|---|
| 2008/0280942 A1 | 11/2008 | Diaz-Fernandez et al. |
| 2009/0042866 A1 | 2/2009 | Lennox et al. |
| 2009/0156593 A1 | 6/2009 | Zemolka et al. |
| 2009/0156626 A1 | 6/2009 | Hinze et al. |
| 2009/0163716 A1 | 6/2009 | Hinze et al. |
| 2009/0203577 A1 | 8/2009 | Baik et al. |
| 2009/0247505 A1 | 10/2009 | Zemolka et al. |
| 2009/0247530 A1 | 10/2009 | Nolte et al. |
| 2009/0247561 A1 | 10/2009 | Zemolka et al. |
| 2009/0247573 A1 | 10/2009 | Zemolka et al. |
| 2009/0247591 A1 | 10/2009 | Zemolka et al. |
| 2009/0326218 A1 | 12/2009 | Martin et al. |
| 2010/0009986 A1 | 1/2010 | Zemolka et al. |
| 2010/0048553 A1 | 2/2010 | Schunk et al. |
| 2010/0048554 A1 | 2/2010 | Schunk et al. |
| 2010/0173824 A1 | 7/2010 | Busch et al. |
| 2011/0015220 A1 | 1/2011 | Linz et al. |
| 2011/0059999 A1 | 3/2011 | Frormann et al. |

FOREIGN PATENT DOCUMENTS

| | | |
|---|---|---|
| AU | 2009228648 | 10/2009 |
| CA | 2446461 A1 | 11/2002 |
| CA | 2550868 | 7/2005 |
| CA | 2658376 A1 | 1/2008 |
| CA | 2658379 | 1/2008 |
| CA | 2718209 | 10/2009 |
| CA | 2719735 | 10/2009 |
| CA | 2719736 | 10/2009 |
| CA | 2719739 | 10/2009 |
| CA | 2719742 | 10/2009 |
| CA | 2719743 | 10/2009 |
| CA | 2446461 C | 4/2011 |
| CN | 102046591 | 5/2011 |
| CN | 102046595 | 5/2011 |
| CN | 102046596 | 5/2011 |
| CN | 102046597 | 5/2011 |
| CN | 102083790 | 6/2011 |
| CO | 6251240 | 2/2011 |
| CO | 6251244 | 2/2011 |
| DE | 28 39 891 | 4/1979 |
| EC | SP10010533 | 11/2010 |
| EC | SP11010529 | 11/2010 |
| EP | 2260022 | 10/2009 |
| EP | 2257526 | 12/2010 |
| EP | 2260021 | 12/2010 |
| EP | 2260042 | 12/2010 |
| EP | 2271613 | 1/2011 |
| EP | 2280941 | 2/2011 |
| GB | 1 055 203 | 1/1967 |
| JP | 2011515430 | 5/2011 |
| JP | 2011515431 | 5/2011 |
| JP | 2011517668 | 6/2011 |
| JP | 2011517669 | 6/2011 |
| JP | 2011517670 | 6/2011 |
| KR | 20100132048 | 12/2010 |
| KR | 20100136521 | 12/2010 |
| MX | 2010009955 | 9/2010 |
| MX | 2010010337 | 10/2010 |
| MX | 2010010339 | 10/2010 |
| MX | 2010010407 | 10/2010 |
| MX | 2010010446 | 11/2010 |
| MX | 2010010448 | 11/2010 |
| PE | 16502009 | 11/2009 |
| PE | 16572009 | 11/2009 |
| PE | 18222009 | 12/2009 |
| PE | 18232009 | 12/2009 |
| PE | 16892009 | 11/2011 |
| TW | 200940541 | 10/2009 |
| TW | 200944501 | 11/2009 |
| WO | 01 87838 | 11/2001 |
| WO | 02 90330 | 5/2002 |
| WO | 03 008370 | 7/2002 |
| WO | 02 090317 | 11/2002 |
| WO | 02090317 | 11/2002 |
| WO | 03 008731 | 1/2003 |
| WO | 03 080557 | 1/2003 |
| WO | 2004 043899 | 5/2004 |
| WO | 2004 043900 | 5/2004 |
| WO | 2004 043902 | 5/2004 |
| WO | 2004 043909 | 5/2004 |
| WO | 2004 043949 | 5/2004 |
| WO | 2004 043967 | 5/2004 |
| WO | 2005 063769 | 7/2005 |
| WO | 2005 066183 | 7/2005 |
| WO | 2005 110970 | 11/2005 |
| WO | 2005 110971 | 11/2005 |
| WO | 2005 110973 | 11/2005 |
| WO | 2005 110974 | 11/2005 |
| WO | 2005 110975 | 11/2005 |
| WO | 2005 110976 | 11/2005 |
| WO | 2005 110977 | 11/2005 |
| WO | 2006 018184 | 2/2006 |
| WO | 2006058088 | 6/2006 |
| WO | 2006065479 | 6/2006 |
| WO | 2006065480 | 6/2006 |
| WO | 2006 108565 | 10/2006 |
| WO | 2007 079927 | 7/2007 |
| WO | 2007 079928 | 7/2007 |
| WO | 2007 079930 | 7/2007 |
| WO | 2007 079931 | 7/2007 |
| WO | 2007 124903 | 11/2007 |
| WO | 2008 009416 | 1/2008 |
| WO | 2008009415 | 1/2008 |
| WO | 2008040481 | 4/2008 |
| WO | 2008101659 | 8/2008 |
| WO | 2008101660 | 8/2008 |
| WO | 2009118163 | 10/2009 |
| WO | 2009118168 | 10/2009 |
| WO | 2009118169 | 10/2009 |
| WO | 2009118171 | 10/2009 |
| WO | 2009118173 | 10/2009 |
| WO | 2009118174 | 10/2009 |

OTHER PUBLICATIONS

Calo, et al, "Pharmacology of nociceptin and its receptor: a novel therapeutic target"; British Journal of Pharmacology (2000) 129, pp. 1261-1283.

Patani et al Chem rev. 1996, vol. 96, p. 3147-3176.

Dorwald, F. A., Side reactions in Oranic Synthesis, 2005, Wiley: VCH, Weinheim p. IX of Preface.

Ardati et al. Interaction of [3H]Orphanin FQ and 125I-Tyr14-Orphanin FQ with the Orphanin FQ Receptor: Kinetics and Modulation by Cations and Guanine Nucleotides. Mol. Pharmacol., 51, 1997, p. 816-824.

Bavetsias et al., "Design and Synthesis of Cyclopenta[g]quinazoline-Based Antifolates as Inhibitors of Thymidylate Synthase and Potential Antitumor Agents", J. Med. Chem, No. 43, pp. 1910-1926, (2000).

Catterall et al., "Binding of Batrachotoxinin a 20-α-Benzoate to a Receptor Site Associated with Sodium Channels in Synaptic Nerve Ending Particles", The Journal of Biological Chemistry, vol. 256, No. 17, pp. 8922-8927, Sep. 10, 1981.

Dirat et al., "Expeditious systhesis of novel NK1 antagonists based on a 1,2,4-trisubstituted cyclohexane", Tetrahedron Letters, No. 47, pp. 1295-1298, (2006).

Elliot et al., "NK1 antagonists based on seven membered lactam scaffolds", Bioorganic & Medicinal Chemistry Letters No. 16, pp. 2929-2932, (2006).

Hamzé et al., "Systhesis of Various 3-Substituted 1,2,4-Oxadiazole-Containing Chiral B3- and α-Amino Acids from Fmoc-Protected Aspartic Acid", J. Org. Chem. No. 68, pp. 7316-7321, (2003).

Hashmi et al., "Gold Catalysis: Mild Conditions for the Synthesis of Oxazoles from N-Propargylcarboxamides and Mechanistic Aspects", Organic Letters, 2004, vol. 6.

Katritzky et al., "The Chemistry of N-Substituted Benzotriazoles; Part 11.1 The Preparation of Tertiary Amines Containing Tertiary-Alkyl Groups from Ketones, Secondary Amines and Organometallic Reagents", Communications, pp. 66-69, Jan. 1989.

Kudzma et al., "4-Phenyl- and a 4-Heteroaryl-4-anilidopiperidines. A Novel Class of Analgesic and Anesthetic Agents1", J. Med. Chem. No. 32, pp. 2534-2542, (1989).

Layer, Robert W. "The Chemistry of Imines", B.F. Goodrich Co., Research Center, pp. 489-510; Dec. 7, 1963.

Lednicer et al., "4-Amino-4-arylcyclohexanones and Their Derivatives, a Novel Class of Analgesics. 1. Modification of the Aryl Ring", The Upjohn Company, Research Laboratories, Aug. 7, 1979.

Lee et al., "Introduction of Heterocycles at the 2-position of Indoline as Ester Bioisosteres", Bull. Koren Chem. Soc. vol. 25, No. 2 pp. 207-212, (2004).

Maddox et al., "The Synthesis of Phencyclidine and Other 1-Arylcyclohexylamines", Research Laboratories, Parke, Davis and Company; vol. 8, pp. 230-232, 1965.

Morwick et al., "A Practical Approach to the Synthesis of 2,4-Disubstituted Oxazoles from Amino Acids", Organic Letters, vol. 4, No. 16, pp. 2665-2668, (2002).

Thompson et al., "Structure-Based Design of Cathepsin K Inhibitors Containing a Benzyloxy-Substituted Benzoyl Peptidomimetic", Journal of Medical Chemistry, vol. 41, No. 21, 1998, pp. 3923-3927.

Regitz et al.; Chem. Ber., No. 101, 1968, pp. 3734-3743.

Ma et al. J. Org. Chem. 2001, 66, 4525-4542.

Finlayson, et al., European Journal of Pharmacology, 412 (2001), pp. 203-212.

Prashad et al., Tetahedron LEtters, No. 46, 2005, pp. 5455-5458.

D'Amour et al., The Biological Research Laboratory, Jan. 27, 1941, pp. 74-79.

Katritzky et al., Synthesis, Dec. 1992, pp. 1295-1298.

Corey et al.; Tetrahedron Letters, No. 36, 1972, pp. 3769-3772.

Harned et al.; Tetrahedron, No. 61, 2005, pp. 12093-12099.

Shiner et al. J. Am. Chem. Soc. 1981, 103, 436-442.

Yamagishi et al., J. Med. Chem. 35, 1992, pp. 2085-2094.

Gleave et al.; Bioorganic & Medicinal Chemistry Letters 8, 1998, pp. 1231-1236.

Sandmeyer, Helv.Chim.Acta; 2; 1919; 239 (cited on p. 53 of the specification).

Katz et al.; J. Med. Chem. 31, 1988; pp. 1244-1250.

Van Bac et al. Tetrahedron Letters, 1988, vol. 29, pp. 2819-2822.

Kato et al. J. Fluorine Chemistry, 99, 1999, pp. 5-7.

Kim et al., J.M, Pain, 50 (1992) 355-363.

Piper, et al; Journal of Medicinal Chemistry, US American Chemical Society, Washington, No. 9, Jan. 1, 1966; pp. 911-920.

Gilbert, et al; Journal of the American Chemical Society, 1950, No. 72, pp. 2411-2417.

Chu, et al.; Tetrahedron, Elsevier Science Publishers, Amsterdam, NL, No. 62, 2006, pp. 5536-5548.

Rose et al, Can J. Chem., 74, 1996, 1836.

Meunier, et al, "Isolation and structure of the endogenous agonist of opioid receptor-like ORL1 receptor", Nature, vol. 377, Oct. 12, 1995, pp. 532-535.

Reinscheid, et al, "Orphanin FQ: A Neuropepetide that Activates an Opioidlike G Protein-Coupled Receptor", Science, vol. 270, Nov. 3, 1995, pp. 792-794.

Mogil, et al, "Orphanin FQ is a Functional Anti-Opioid Peptide"; Neuroscience, vol. 75, No. 2, 1996, pp. 333-337.

Jenck, et al, "Orphanin FQ acts as an anxiolytic to attenuate behavioral responses to stress"; Proc. Natl. Acad. Sci. USA, vol. 94, Dec. 1997, pp. 14854-14858.

King et al, "Spinal analgesic activity of orphanin FQ/nociceptin and its fragments", Neuroscience Letters 223 (1997), pp. 113-116.

Gaspar et al. Mild Cobalt-Catalyzed Hydrocyanation of Olefins with Tosyl Cyanide. Angew. Chemie. Int. Ed. 2007, vol. 46, pp. 4519-4522.

Xia et al. Organic Letters 2005, vol. 7, No. 7, 1315-1318.

Messina, F. et al.; Tetrahedron: Asymmetry 11 (2000) 1681-1685.

Greene et al, Protective Groups in Organic Synthesis; Wiley Interscience Publication; 3rd Edition, 1999.

Jirkovsky et al., J. Heterocycl. Chem., 12, 1975, pp. 937-940.

Beck et al., J. Chem. Soc. Perkin 1, 1992, pp. 813-822.

Shinada et al., Tetrahedron Letters, vol. 39, 1996, pp. 7099-7102.

Garden et al., Tetrahedron, 58, 2002, pp. 8399-8412.

Lednicer et al., J. Med. Chem., 23, 1980, pp. 424-430.

Williams et al., J. Org. Chem. 1980, 45, pp. 5082-5088.

Bandini et al. J. Org. Chem. 67, 2002, pp. 5386-5389.

Davis et al., J. Med. Chem. 35, 1992, pp. 177-184.

HYDROXYMETHYLCYCLOHEXYLAMINES

This application is a Continuation of PCT/EP2009/002184, filed Mar. 25, 2009, which claims foreign priority benefit under 35 U.S.C. §119 of the European Patent Application No. 08005809.2 filed Mar. 27, 2008.

The present invention relates to hydroxymethylcyclohexylamines which have an affinity for the μ opioid receptor and the ORL1 receptor, processes for the preparation thereof, medicaments containing these compounds and the use of these compounds for the preparation of medicaments.

Cyclohexane derivatives which have an affinity for the μ opioid receptor and the ORL1 receptor are known in the prior art. In this connection, reference may be made by way of example, in the full scope, to WO2002/090317, WO2002/90330, WO2003/008370, WO2003/008731, WO2003/080557, WO2004/043899, WO2004/043900, WO2004/043902, WO2004/043909, WO2004/043949, WO2004/043967, WO2005/063769, WO2005/066183, WO2005/110970, WO2005/110971, WO2005/110973, WO2005/110974, WO2005/110975, WO2005/110976, WO2005/110977, WO2006/018184, WO2006/108565, WO2007/079927, WO2007/079928, WO2007/079930, WO2007/079931, WO2007/124903, WO2008/009415 and WO2008/009416.

However, the known compounds are not satisfactory in every respect. Thus, the known compounds sometimes show a not always optimum affinity for the ORL1 receptor. In general, it can be assumed that as the affinity of a compound for the ORL1 receptor increases, the dose required to bring about the same pharmacological action decreases. The lower the dose required, however, the lower also the probability of the occurrence of undesirable side effects.

Furthermore, in suitable binding assays the known compounds sometimes show a certain affinity for the hERG ion channel, for the L-type calcium ion channel (phenylalkylamine, benzothiazepine, hydropyridine binding sites) or for the sodium channel in the BTX assay (batrachotoxin), which can in each case be interpreted as an indication of cardiovascular side effects. Numerous of the known compounds furthermore show only a low solubility in aqueous media, which can have an adverse effect, inter alia, on the bioavailability. The chemical stability of the known compounds moreover is often only inadequate. Thus, the compounds sometimes do not show an adequate pH, UV or oxidation stability, which can have an adverse effect, inter alia, on the storage stability and also on the oral bioavailability. The known compounds furthermore in some cases have an unfavourable PK/PD (pharmacokinetic/pharmacodynamic) profile, which can manifest itself e.g. in too long a duration of action.

The metabolic stability of the known compounds also appears to be in need of improvement. An improved metabolic stability can indicate an increased bioavailability. A weak or non-existent interaction with transporter molecules involved in the uptake and excretion of drugs is also to be evaluated as an indication of an improved bioavailability and at best low drug interactions.

Furthermore, the interactions with the enzymes involved in the breakdown and excretion of enzymes should be as low as possible, since such test results likewise indicate that at best low drug interactions or none at all are to be expected.

There is a need for further compounds which bind to the ORL1 receptor. The compounds should as far as possible show at least a comparable, preferably a higher affinity for the ORL1 receptor. Additional binding to other receptors (e.g. μ opioid receptor, δ opioid receptor) and the additional antagonistic action on other receptors (e.g. B1R receptor) can bring additional advantages.

The compounds moreover should as far as possible have a comparable, but preferably a better solubility in aqueous media.

The invention is based on the object of providing compounds which are suitable for pharmaceutical purposes and have advantages over the compounds of the prior art.

This object is achieved by the subject matter of the claims. It has been found, surprisingly, that substituted cyclohexane derivatives which have an affinity for the μ opioid receptor and the ORL1 receptor can be prepared.

The invention relates to compounds of the general formula (1)

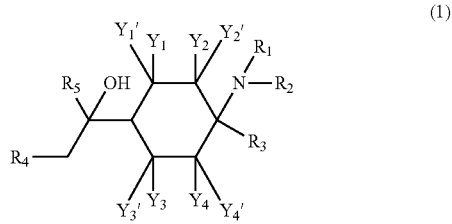

wherein $Y_1, Y_1', Y_2, Y_2', Y_3, Y_3', Y_4$ and $Y_4'$ in each case independently of each other are chosen from the group consisting of —H, —F, —Cl, —Br, —I, —CN, —NO$_2$, —CHO, —R$_0$, —C(=O)R$_0$, —C(=O)H, —C(=O)—OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —S(=O)$_{1-2}$R$_0$, —S(=O)$_{1-2}$OH, —S(=O)$_{1-2}$OR$_0$, —S(=O)$_{1-2}$NH$_2$, —S(=O)$_{1-2}$NHR$_0$ or —S(=O)$_{1-2}$N(R$_0$)$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NH—C(=O)N(R$_0$)$_2$; preferably in each case independently of each other are chosen from the group consisting of —H, —F, —Cl, —CN and —C$_{1-8}$-aliphatic; or $Y_1$ and $Y_1'$, or $Y_2$ and $Y_2'$, or $Y_3$ and $Y_3'$, or $Y_4$ and $Y_4'$ together represent =O;

$R_0$ in each case independently represents —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;

$R_1$ and $R_2$ independently of each other represent —H or —C$_{1-8}$-aliphatic, wherein $R_1$ and $R_2$ preferably do not both represent —H; or $R_1$ and $R_2$ together form a ring and represent —(CH$_2$)$_{2-4}$;

$R_3$ represents —R$_0$;

$R_4$ represents —H, —F, —Cl, —Br, —I, —R$_0$, —C(=O)H, —C(=O)R$_0$, —C(=O)OR$_0$, —CN, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)—N(R$_0$)$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NHR$_0$, —NHC(=O)—N(R$_0$)$_2$, —NO$_2$, —SH, —SR$_0$, —S(=O)$_{1-2}$R$_0$, —S(=O)$_{1-2}$OH, —S(=O)$_{1-2}$OR$_0$, —S(=O)$_{1-2}$NH$_2$, —S(=O)$_{1-2}$NHR$_0$, —S(=O)$_{1-2}$N(R$_0$)$_2$, —OS(=O)$_{1-2}$R$_0$, —OS(=O)$_{1-2}$OH, —OS(=O)$_{1-2}$OR$_0$, —OS(=O)$_{1-2}$NH$_2$, —OS(=O)$_{1-2}$NHR$_0$ or —OS(=O)$_{1-2}$N(R$_0$)$_2$;

$R_5$ represents —H, —$R_0$, —C(=O)H, —C(=O)$R_0$, —C(=O)O$R_0$, —CN, —C(=O)$NH_2$, —C(=O)$NHR_0$ or —C(=O)N($R_0$)$_2$;

wherein

"aliphatic" in each case is a branched or unbranched, saturated or mono- or polyunsaturated, unsubstituted or mono- or polysubstituted, aliphatic hydrocarbon radical;

"cycloaliphatic" in each case is a saturated or mono- or polyunsaturated, unsubstituted or mono- or polysubstituted, alicyclic, mono- or multicyclic hydrocarbon radical, the number of ring carbon atoms of which is preferably in the stated range (i.e. "$C_{3-8}$-"cycloaliphatic preferably has 3, 4, 5, 6, 7 or 8 ring carbon atoms);

wherein with respect to "aliphatic" and "cycloaliphatic", "mono- or polysubstituted" is understood as meaning substitution once or several times of one or more hydrogen atoms, i.e. substitution once, twice, three times or completely, by substituents chosen independently of each other from the group consisting of —F, —Cl, —Br, —I, —CN, —$NO_2$, —CHO, =O, —$R_0$, —C(=O)$R_0$, —C(=O)H, —C(=O)OH, —C(=O)O$R_0$, —C(=O)$NH_2$, —C(=O)$NHR_0$, —C(=O)N($R_0$)$_2$, —OH, —O$R_0$, —OC(=O)H, —OC(=O)$R_0$, —OC(=O)O$R_0$, —OC(=O)$NHR_0$, —OC(=O)—N($R_0$)$_2$, —SH, —S$R_0$, —$SO_3$H, —S(=O)$_{1-2}$—$R_0$, —S(=O)$_{1-2}$$NH_2$, —$NH_2$, —$NHR_0$, —N($R_0$)$_2$, —$N^+$($R_0$)$_3$, —$N^+$($R_0$)$_2$$O^-$, —NHC(=O)$R_0$, —NHC(=O)O$R_0$, —NHC(=O)$NH_2$, —NHC(=O)—$NHR_0$, —NH—C(=O)N($R_0$)$_2$, —Si($R_0$)$_3$, —PO(O$R_0$)$_2$;

"aryl" in each case independently represents a carbocyclic ring system having at least one aromatic ring, but without hetero atoms in this ring, wherein the aryl radicals can optionally be fused with further saturated, (partially) unsaturated or aromatic ring systems, which in their turn can have one or more hetero ring atoms, in each case independently of each other chosen from N, O and S, and wherein each aryl radical can be unsubstituted or mono- or polysubstituted, wherein the substituents on aryl can be identical or different and can be in any desired and possible position of the aryl;

"heteroaryl" represents a 5-, 6- or 7-membered cyclic aromatic radical which contains 1, 2, 3, 4 or 5 hetero atoms, wherein the hetero atoms are identical or different and are nitrogen, oxygen or sulfur and the heterocyclyl can be unsubstituted or mono- or polysubstituted; wherein in the case of substitution on the heterocyclyl the substituents can be identical or different and can be in any desired and possible position of the heteroaryl; and wherein the heterocyclyl can also be part of a bi- or polycyclic system;

wherein with respect to "aryl" and "heteroaryl", "mono- or polysubstituted" is understood as meaning substitution once or several times of one or more hydrogen atoms of the ring system by substituents chosen from the group consisting of —F, —Cl, —Br, —I, —CN, —$NO_2$, —CHO, =O, —$R_0$, —C(=O)$R_0$, —C(=O)H, —C(=O)OH, —C(=O)O$R_0$, —C(=O)$NH_2$, —C(=O)$NHR_0$, —C(=O)N($R_0$)$_2$, —OH, —O($CH_2$)$_{1-2}$O—, —O$R_0$, —OC(=O)H, —OC(=O)$R_0$, —OC(=O)O$R_0$, —OC(=O)$NHR_0$, —OC(=O)—N($R_0$)$_2$, —SH, —S$R_0$, —$SO_3$H, —S(=O)$_{1-2}$—$R_0$, —S(=O)$_{1-2}$$NH_2$, —$NH_2$, —$NHR_0$, —N($R_0$)$_2$, —$N^+$($R_0$)$_3$, —$N^+$($R_0$)$_2$$O^-$, —NHC(=O)$R_0$, —NHC(=O)O$R_0$, —NHC(=O)$NH_2$, —NHC(=O)—$NHR_0$, —NH—C(=O)N($R_0$)$_2$, —Si($R_0$)$_3$, —PO(O$R_0$)$_2$; wherein N ring atoms optionally present can in each case be oxidized (N-oxide);

in the form of an individual stereoisomer or mixture thereof, the free compounds and/or their physiologically acceptable salts and/or solvates.

Where various radicals are combined, for example $R_1$ and $R_2$, and where radicals on substituents thereof are combined, such as e.g. —O$R_0$, —OC(=O)$R_0$, —OC(=O)$NHR_0$, a substituent, e.g. $R_0$, can assume different meanings for two or more radicals, for example —O$R_0$, —OC(=O)$R_0$, —OC(=O)$NHR_0$, within a substance.

The compounds according to the invention show good binding to the ORL1 receptor and the µ opioid receptor.

In a preferred embodiment, the compounds according to the invention have a ratio of ORL1/µ affinity of at least 0.1. The ORL1/µ ratio is defined as $1/[K_{i(ORL1)}/K_{i(µ)}]$. Particularly preferably, the ORL1/µ ratio is at least 0.2 or at least 0.5, more preferably at least 1.0 or at least 2.0, still more preferably at least 3.0 or at least 4.0, most preferably at least 5.0 or at least 7.5, and in particular at least 10 or at least 15. In a preferred embodiment the ORL1/µ ratio is in the range of from 0.1 to 30, more preferably 0.1 to 25.

In another preferred embodiment, the compounds according to the invention have a ratio of ORL1/µ affinity of more than 30, more preferably at least 50, still more preferably at least 100, most preferably at least 200 and in particular at least 300.

The compounds according to the invention preferably have a $K_i$ value on the µ opioid receptor of at most 500 nM, more preferably at most 100 nM, still more preferably 50 nM, most preferably at most 10 nM and in particular at most 1.0 nM.

Methods for determination of the $K_i$ value on the µ opioid receptor are known to the person skilled in the art. The determination is preferably carried out as described in connection with the examples.

The compounds according to the invention preferably have a $K_i$ value on the ORL1 receptor of at most 500 nM, more preferably at most 100 nM, still more preferably 50 nM, most preferably at most 10 nM and in particular at most 1.0 nM.

Methods for determination of the $K_i$ value on the ORL1 receptor are known to the person skilled in the art. The determination is preferably carried out as described in connection with the examples.

It has been found, surprisingly, that compounds with an affinity for the ORL1 and µ opioid receptor in which the ratio of ORL1 to µ defined by $1/[K_{i(ORL1)}/K_{i(µ)}]$ is in the range of from 0.1 to 30, preferably from 0.1 to 25, have a pharmacological profile which has clear advantages compared with the other opioid receptor ligands:

1. The compounds according to the invention show an activity in acute pain models which is sometimes comparable to that of the usual level 3 opioids. At the same time, however, they are distinguished by a clearly better tolerability compared with conventional µ opioids.
2. In contrast to the usual level 3 opioids, the compounds according to the invention show a clearly higher activity in mono- and polyneuropathy pain models, which is to be attributed to a synergism of the ORL1 and µ opioid component.
3. In contrast to the usual level 3 opioids, the compounds according to the invention show a substantial, preferably a complete separation of antiallodynic or antihyperalgesic action and antinociceptive effect in neuropathic animals.
4. In contrast to the usual level 3 opioids, the compounds according to the invention show a clear intensification of action against acute pain in animal models for chronic inflammation pain (inter alia carrageenan- or CFA-induced hyperalgesia, visceral inflammation pain).
5. In contrast to the usual level 3 opioids, side effects typical of µ-opioids (inter alia respiratory depression, opioid-induced hyperalgesia, physical dependency/ withdrawal, emotional dependency/addiction) are clearly reduced or preferably are not to be observed with the compounds according to the invention in the therapeutically active dose range.

On the basis of the reduced μ opioid side effects on the one hand and the increased activity on chronic, preferably neuropathic pain on the other hand, the mixed ORL1/μ agonists are thus distinguished by clearly increased safety margins compared with pure μ opioids. This results in a clearly increased "therapeutic window" in the treatment of states of pain, preferably chronic pain, still more preferably neuropathic pain.

Preferably, $Y_1, Y_1', Y_2, Y_2', Y_3, Y_3', Y_4$ and $Y_4'$ in each case independently of each other are chosen from the group consisting of —H, —F, —Cl, —Br, —I, —CN, —NH$_2$, —NH—C$_{1-6}$-aliphatic, —NH—C$_{3-8}$-cycloaliphatic, —NH—C$_{1-6}$-aliphatic-OH, —N(C$_{1-6}$-aliphatic)$_2$, —N(C$_{3-8}$-cycloaliphatic)$_2$, —N(C$_{1-6}$-aliphatic-OH)$_2$, —NO$_2$, —NH—C$_{1-6}$-aliphatic-C$_{3-8}$-cycloaliphatic, —NH—C$_{1-6}$-aliphatic-aryl, —NH—C$_{1-6}$-aliphatic-heteroaryl, —NH-aryl, —NH-heteroaryl, —SH, —S—C$_{1-6}$-aliphatic, —S—C$_{3-8}$-cycloaliphatic, —S—C$_{1-6}$-aliphatic-C$_{3-8}$-cycloaliphatic, —S—C$_{1-6}$-aliphatic-aryl, —S—C$_{1-6}$-aliphatic-heteroaryl, —S-aryl, —S-heteroaryl, —OH, —O—C$_{1-6}$-aliphatic, —O—C$_{3-8}$-cycloaliphatic, —O—C$_{1-6}$-aliphatic-OH, —O—C$_{1-6}$-aliphatic-C$_{3-8}$-cycloaliphatic, —O—C$_{1-6}$-aliphatic-aryl, —O—C$_{1-6}$-aliphatic-heteroaryl, —O-aryl, —O-heteroaryl, —O—C(═O)C$_{1-6}$-aliphatic, —O—C(═O)C$_{3-8}$-cycloaliphatic, —O—C(═O)C$_{1-6}$-aliphatic-OH, —O—C(═O)C$_{1-6}$-aliphatic-C$_{3-8}$-cycloaliphatic, —O—C(═O)C$_{1-6}$-aliphatic-aryl, —O—C(═O)C$_{1-6}$-aliphatic-heteroaryl, —O—C(═O)aryl, —O—C(═O)heteroaryl, —C$_{1-6}$-aliphatic, —C$_{3-8}$-cycloaliphatic, —C$_{1-6}$-aliphatic-C$_{3-8}$-cycloaliphatic, —C$_{1-6}$-aliphatic-aryl, —C$_{1-6}$-aliphatic-heteroaryl, -aryl, -heteroaryl, —C(═O)C$_{1-6}$-aliphatic, —C(═O)C$_{3-8}$-cycloaliphatic, —C(═O)C$_{1-6}$-aliphatic-C$_{3-8}$-cycloaliphatic, —C(═O)C$_{1-6}$-aliphatic-aryl, —C(═O)C$_{1-6}$-aliphatic-heteroaryl, —C(═O)aryl, —C(═O)heteroaryl, —CO$_2$H, —CO$_2$—C$_{1-6}$-aliphatic, —CO$_2$—C$_{3-8}$-cycloaliphatic, —CO$_2$—C$_{1-6}$-aliphatic-C$_{3-8}$-cycloaliphatic, —CO$_2$—C$_{1-6}$-aliphatic-aryl, —CO$_2$—C$_{1-6}$-aliphatic-heteroaryl, —CO$_2$-aryl, —CO$_2$-heteroaryl; or $Y_1$ and $Y_1'$, or $Y_2$ and $Y_2'$, or $Y_3$ and $Y_3'$, or $Y_4$ and $Y_4'$ together represent ═O. Preferably, $Y_1, Y_1', Y_2, Y_2', Y_3, Y_3', Y_4$ and $Y_4'$ in each case independently of each other are chosen from the group consisting of —H, —F, —Cl, —Br, —I, —CN, —NH$_2$ and —OH.

In a preferred embodiment, one of the radicals $Y_1, Y_1', Y_2, Y_2', Y_3, Y_3', Y_4$ and $Y_4'$ differs from —H and the remaining radicals represent —H.

Particularly preferably, $Y_1, Y_1', Y_2, Y_2', Y_3, Y_3', Y_4$ and $Y_4'$ each represent —H.

$R_0$ preferably in each case independently represents —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl or —C$_{1-8}$-aliphatic-heteroaryl. In this context, —C$_{1-8}$-aliphatic-C$_{3-12}$-cycloaliphatic, —C$_{1-8}$-aliphatic-aryl or —C$_{1-8}$-aliphatic-heteroaryl means that the radicals —C$_{3-12}$-cycloaliphatic, -aryl or -heteroaryl are in each case bonded via a divalent —C$_{1-8}$-aliphatic-bridge. Preferred examples for —C$_{1-8}$-aliphatic-aryl are —CH$_2$—C$_6$H$_5$, —CH$_2$CH$_2$—C$_6$H$_5$, and —CH═CH—C$_6$H$_5$.

$R_1$ and $R_2$ independently of each other represent —H or —C$_{1-5}$-aliphatic, or the radicals $R_1$ and $R_2$ together form a ring and denote —(CH$_2$)$_2$—, —(CH$_2$)$_3$— or —(CH$_2$)$_4$—. Preferably, $R_1$ and $R_2$ independently of each other represent —H, —CH$_3$ or —CH$_2$CH$_3$, or $R_1$ and $R_2$ together form a ring and represent —CH$_2$CH$_2$— or —CH$_2$CH$_2$CH$_2$—. Compounds wherein $R_1$ and $R_2$ independently of each other represent —CH$_3$ or —H, wherein $R_1$ and $R_2$ do not simultaneously denote —H, are particularly preferred. In a preferred embodiment, $R_1$=$R_2$. In another preferred embodiment, $R_1$≠$R_2$. Preferably, $R_1$ and $R_2$ together with the nitrogen atom to which they are bonded form one of the following functional groups:

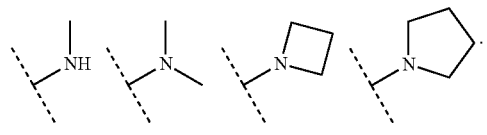

Preferably, $R_3$ represents —C$_{1-8}$-aliphatic, —C$_{3-8}$-cycloaliphatic, -aryl, -heteroaryl; or -aryl, -heteroaryl or —C$_{3-8}$-cycloaliphatic in each case bonded via a —C$_{1-3}$-aliphatic group.

Preferably, $R_3$ represents -ethyl, -propyl, -butyl, -pentyl, -hexyl, -heptyl, -cyclopentyl, -cyclohexyl, -phenyl, -naphthyl, -anthracenyl, -thiophenyl, -benzothiophenyl, -furyl, -thienyl, -thiazolyl, -benzofuranyl, -benzodioxolanyl, -indolyl, -indanyl, -benzodioxanyl, -pyrrolyl, -pyridyl, -pyrimidyl or -pyrazinyl, in each case unsubstituted or mono- or polysubstituted; -cyclopentyl, -cyclohexyl, -phenyl, -naphthyl, -anthracenyl, -thiophenyl, -benzothiophenyl, -furyl, -thienyl, -thiazolyl, -benzofuranyl, -benzodioxolanyl, -indolyl, -indanyl, -benzodioxanyl, -pyrrolyl, -pyridyl, -pyrimidyl or -pyrazinyl bonded via a saturated, unbranched —C$_{1-3}$-aliphatic group and in each case unsubstituted or mono- or polysubstituted.

More preferably, $R_3$ represents -ethyl, -propyl, -butyl, -pentyl, -hexyl, -heptyl, -cyclopentyl, -cyclohexyl, -phenyl, -benzyl, -naphthyl, -anthracenyl, -thiophenyl, -benzothiophenyl, -furyl, -thienyl, thiazolyl, -benzofuranyl, -benzodioxolanyl, -indolyl, -indanyl, -benzodioxanyl, -pyrrolyl, -pyridyl, -pyrimidyl or -pyrazinyl, in each case unsubstituted or mono- or polysubstituted; or —C$_{5-6}$-cycloaliphatic, -phenyl, -naphthyl, -anthracenyl, -thiophenyl, -benzothiophenyl, pyridyl, -furyl, -thienyl, -thiazolyl, -benzofuranyl, -benzodioxolanyl, -indolyl, -indanyl, -benzodioxanyl, -pyrrolyl, -pyrimidyl, -triazolyl or -pyrazinyl bonded via a saturated, unbranched —C$_{1-3}$-aliphatic group and in each case unsubstituted or mono- or polysubstituted.

More preferably, $R_3$ represents -propyl, -butyl, -pentyl, -hexyl, -phenyl, -thiophenyl, -furyl, -thienyl, thiazolyl, -naphthyl, benzyl, -benzofuranyl, -indolyl, -indanyl, -benzodioxanyl, -benzodioxolanyl, -pyridyl, -pyrimidyl, -pyrazinyl, triazolyl or benzothiophenyl, in each case substituted or mono- or polysubstituted; or -phenyl, -furyl, -thienyl or -thiazolyl bonded via a saturated, unbranched —C$_{1-3}$-aliphatic group and in each case unsubstituted or mono- or polysubstituted.

Still more preferably, $R_3$ represents -propyl, -butyl, -pentyl, -hexyl, -phenyl, -phenethyl, -thiophenyl, -pyridyl, -triazolyl, -benzothiophenyl or -Benzyl, in each case substituted or unsubstituted, particularly preferably -propyl, -3-methoxypropyl, -butyl, -pentyl, -hexyl, -phenyl, -3-methylphenyl, -3-fluorophenyl, -benzo[1,3]-dioxolyl, -thienyl, -benzothiophenyl, -4-chlorobenzyl, -benzyl, -3-chlorobenzyl, -4-methylbenzyl, -2-chlorobenzyl, -4-fluorobenzyl, -3-methylbenzyl, -2-methylbenzyl, -3-fluorobenzyl, -2-fluorobenzyl, -1-methyl-1,2,4-triazolyl or -phenethyl.

Very particularly preferably, $R_3$ represents -butyl, -ethyl, -3-methoxypropyl, -benzothiophenyl, -phenyl, -3-methylphenyl, -3-fluorophenyl, -benzo[1,3]-dioxolyl, -benzyl, -1-methyl-1,2,4-triazolyl, -thienyl or -phenethyl.

Most preferably, $R_3$ represents -phenyl, -benzyl or -phenethyl, in each case unsubstituted or mono- or polysubstituted on the ring; —$C_{1-5}$-aliphatic, —$C_{4-6}$-cycloaliphatic, -pyridyl, -thienyl, -thiazolyl, -imidazolyl, -1,2,4-triazolyl or -benzimidazolyl, unsubstituted or mono- or polysubstituted.

Particularly preferably, $R_3$ represents -phenyl, -benzyl, -phenethyl, -thienyl, -pyridyl, -thiazolyl, -imidazolyl, -1,2,4-triazolyl, -benzimidazolyl or -benzyl, unsubstituted or mono- or polysubstituted by —F, —Cl, —Br, —CN, —$CH_3$, —$C_2H_5$, —$NH_2$, —$NO_2$, —SH, —$CF_3$, —OH, —$OCH_3$, —$OC_2H_5$ or —$N(CH_3)_2$; -ethyl, -n-propyl, -2-propyl, -allyl, -n-butyl, -iso-butyl, -sec-butyl, -tert-butyl, -n-pentyl, -iso-pentyl, -neo-pentyl, -n-hexyl, -cyclopentyl or -cyclohexyl, in each case unsubstituted or mono- or polysubstituted by —OH, —$OCH_3$ or —$OC_2H_5$, -thienyl, -pyridyl, -thiazolyl, -imidazolyl, -1,2,4-triazolyl and -benzimidazolyl preferably being unsubstituted.

In a preferred embodiment, $R_3$ represents —$C_{1-6}$-aliphatic, -aryl (preferably -phenyl) or -heteroaryl (preferably -thienyl, -thiazolyl or -pyridyl), wherein -aryl and -heteroaryl are in each case unsubstituted or mono- or polysubstituted by substituents independently of each other chosen from —F, —Cl, —Br, —I, —$CH_3$, —$OCH_3$ and —OH.

Particularly preferably, $R^3$ represents -phenyl, unsubstituted or monosubstituted by —F, —Cl, —CN, —$CH_3$; -thienyl, -ethyl, -n-propyl or -n-butyl, unsubstituted or mono- or polysubstituted by —$OCH_3$, —OH or —$OC_2H_5$, in particular by —$OCH_3$.

Preferably, $R_4$ represents —H, —F, —Cl, —Br, —I, —$C_{1-8}$-aliphatic, —$C_{3-12}$-cycloaliphatic, -aryl, -heteroaryl, —$C_{1-8}$-aliphatic-$C_{3-12}$-cycloaliphatic, —$C_{1-8}$-aliphatic-aryl, —$C_{1-8}$-aliphatic-heteroaryl, —C(=O)H, —C(=O)—$C_{1-8}$-aliphatic, —C(=O)—$C_{3-12}$-cycloaliphatic, —C(=O)-aryl, —C(=O)-heteroaryl, —C(=O)—$C_{1-8}$-aliphatic-$C_{3-12}$-cycloaliphatic, —C(=O)—$C_{1-8}$-aliphatic-aryl, —C(=O)—$C_{1-8}$-aliphatic-heteroaryl, —C(=O)O—$C_{1-8}$-aliphatic, —C(=O)O—$C_{3-12}$-cycloaliphatic, —C(=O)O-aryl, —C(=O)O-heteroaryl, —C(=O)O—$C_{1-8}$-aliphatic-$C_{3-12}$-cycloaliphatic, —C(=O)O—$C_{1-8}$-aliphatic-aryl, —C(=O)O—$C_{1-8}$-aliphatic-heteroaryl, —CN, —C(=O)$NH_2$, —C(=O)—NH—$C_{1-8}$-aliphatic, —C(=O)NH—$C_{3-12}$-cycloaliphatic, —C(=O)NH-aryl, —C(=O)NH-heteroaryl, —C(=O)—NH—$C_{1-8}$-aliphatic-$C_{3-12}$-cycloaliphatic, —C(=O)NH—$C_{1-8}$-aliphatic-aryl, —C(=O)NH—$C_{1-8}$-aliphatic-heteroaryl, —C(=O)N($C_{1-8}$-aliphatic)$_2$, —C(=O)N($C_{3-12}$-cycloaliphatic)$_2$, —C(=O)N(aryl)$_2$, —C(=O)N-(heteroaryl)$_2$, —C(=O)N($C_{1-8}$-aliphatic-$C_{3-12}$-cycloaliphatic)$_2$, —C(=O)N($C_{1-8}$-aliphatic-aryl)$_2$, —C(=O)—N($C_{1-8}$-aliphatic-heteroaryl)$_2$, —OH, —$OC_{1-8}$-aliphatic, —$OC_{3-12}$-cycloaliphatic, -Oaryl, -Oheteroaryl, —$OC_{1-8}$-aliphatic-$C_{3-12}$-cycloaliphatic, —$OC_{1-8}$-aliphatic-aryl, —$OC_{1-8}$-aliphatic-heteroaryl, —OC(=O)H, —OC(=O)—$C_{1-8}$-aliphatic, —OC(=O)—$C_{3-12}$-cycloaliphatic, —OC(=O)-aryl, —OC(=O)-heteroaryl, —OC(=O)—$C_{1-8}$-aliphatic-$C_{3-12}$-cycloaliphatic, —OC(=O)—$C_{1-8}$-aliphatic-aryl, —OC(=O)—$C_{1-8}$-aliphatic-heteroaryl, —OC(=O)O—$C_{1-8}$-aliphatic, —OC(=O)O—$C_{3-12}$-cycloaliphatic, —OC(=O)O-aryl, —OC(=O)—O-heteroaryl, —OC(=O)O—$C_{1-8}$-aliphatic-$C_{3-12}$-cycloaliphatic, —OC(=O)O—$C_{1-8}$-aliphatic-aryl, —OC(=O)—O—$C_{1-8}$-aliphatic-heteroaryl, —OC(=O)NH—$C_{1-8}$-aliphatic, —OC(=O)NH—$C_{3-12}$-cycloaliphatic, —OC(=O)NH-aryl, —OC(=O)NH-heteroaryl, —OC(=O)NH—$C_{1-8}$-aliphatic-$C_{3-12}$-cycloaliphatic, —OC(=O)NH—$C_{1-8}$-aliphatic-aryl, —OC(=O)NH—$C_{1-8}$-aliphatic-heteroaryl, —OC(=O)N($C_{1-8}$-aliphatic)$_2$, —OC(=O)N($C_{3-12}$-cycloaliphatic)$_2$, —OC(=O)N(aryl)$_2$, —OC(=O)—N(heteroaryl)$_2$, —OC(=O)N($C_{1-8}$-aliphatic-$C_{3-12}$-cycloaliphatic)$_2$, —OC(=O)N($C_{1-8}$-aliphatic-aryl)$_2$, —OC(=O)N($C_{1-8}$-aliphatic-heteroaryl)$_2$, —$NH_2$, —$NO_2$, —NH—$C_{1-8}$-aliphatic, —NH—$C_{3-12}$-cycloaliphatic, —NH-aryl, —NH-heteroaryl, —NH—$C_{1-8}$-aliphatic-$C_{3-12}$-cycloaliphatic, —NH—$C_{1-8}$-aliphatic-aryl, —NH—$C_{1-8}$-aliphatic-heteroaryl, —N($C_{1-8}$-aliphatic)$_2$, —N($C_{3-12}$-cycloaliphatic)$_2$, —N(aryl)$_2$, —N(heteroaryl)$_2$, —N($C_{1-8}$-aliphatic-$C_{3-12}$-cycloaliphatic)$_2$, —N($C_{1-8}$-aliphatic-aryl)$_2$, —N($C_{1-8}$-aliphatic-heteroaryl)$_2$, —NHC(=O)—$C_{1-8}$-aliphatic, —NHC(=O)—$C_{3-12}$-cycloaliphatic, —NHC(=O)-aryl, —NHC(=O)-heteroaryl, —NHC(=O)—$C_{1-8}$-aliphatic-$C_{3-12}$-cycloaliphatic, —NHC(=O)—$C_{1-8}$-aliphatic-aryl, —NHC(=O)—$C_{1-8}$-aliphatic-heteroaryl, —NHC(=O)O—$C_{1-8}$-aliphatic, —NHC(=O)O—$C_{3-12}$-cycloaliphatic, —NHC(=O)O-aryl, —NHC(=O)O-heteroaryl, —NHC(=O)O—$C_{1-8}$-aliphatic-$C_{3-12}$-cycloaliphatic, —NHC(=O)O—$C_{1-8}$-aliphatic-aryl, —NHC(=O)O—$C_{1-8}$-aliphatic-heteroaryl, —NHC(=O)NH—$C_{1-8}$-aliphatic, —NHC(=O)NH—$C_{3-12}$-cycloaliphatic, —NHC(=O)NH-aryl, —NHC(=O)—NH-heteroaryl, —NHC(=O)NH—$C_{1-8}$-aliphatic-$C_{3-12}$-cycloaliphatic, —NHC(=O)NH—$C_{1-8}$-aliphatic-aryl, —NHC(=O)NH—$C_{1-8}$-aliphatic-heteroaryl, —NHC(=O)N($C_{1-8}$-aliphatic)$_2$, —NHC(=O)N($C_{3-12}$-cycloaliphatic)$_2$, —NHC(=O)N(aryl)$_2$, —NHC(=O)—N(heteroaryl)$_2$, —NHC(=O)—N($C_{1-8}$-aliphatic-$C_{3-12}$-cycloaliphatic)$_2$, —NHC(=O)N($C_{1-8}$-aliphatic-aryl)$_2$, —NHC(=O)N($C_{1-8}$-aliphatic-heteroaryl)$_2$, —SH, —$SC_{1-8}$-aliphatic, —$SC_{3-12}$-cycloaliphatic, -Saryl, -Sheteroaryl, —$SC_{1-8}$-aliphatic-$C_{3-12}$-cycloaliphatic, —$SC_{1-8}$-aliphatic-aryl, —$SC_{1-8}$-aliphatic-heteroaryl, —S(=O)$_{1-2}C_{1-8}$-aliphatic, —S(=O)$_{1-2}C_{3-12}$-cycloaliphatic, —S(=O)$_{1-2}$aryl, —S(=O)$_{1-2}$heteroaryl, —S(=O)$_{1-2}C_{1-8}$-aliphatic-$C_{3-12}$-cycloaliphatic, —S(=O)$_{1-2}C_{1-8}$-aliphatic-aryl, —S(=O)$_{1-2}C_{1-8}$-aliphatic-heteroaryl, —S(=O)$_{1-2}$OH, —S(=O)$_{1-2}OC_{1-8}$-aliphatic, —S(=O)$_{1-2}OC_{3-12}$-cycloaliphatic, —S(=O)$_{1-2}$Oaryl, —S(=O)$_{1-2}$Oheteroaryl, —S(=O)$_{1-2}OC_{1-8}$-aliphatic-$C_{3-12}$-cycloaliphatic, —S(=O)$_{1-2}OC_{1-8}$-aliphatic-aryl, —S(=O)$_{1-2}OC_{1-8}$-aliphatic-heteroaryl, —S(=O)$_{1-2}NH_2$, —S(=O)$_{1-2}NHC_{1-8}$-aliphatic, —S(=O)$_{1-2}NHC_{3-12}$-cycloaliphatic, —S(=O)$_{1-2}$NHaryl, —S(=O)$_{1-2}$NHheteroaryl, —S(=O)$_{1-2}NHC_{1-8}$-aliphatic-$C_{3-12}$-cycloaliphatic, —S(=O)$_{1-2}NHC_{1-8}$-aliphatic-aryl, —S(=O)$_{1-2}NHC_{1-8}$-aliphatic-heteroaryl, —S(=O)$_{1-2}N(C_{1-8}$-aliphatic)$_2$, —S(=O)$_{1-2}N(C_{3-12}$-cycloaliphatic)$_2$, —S(=O)$_{1-2}N(aryl)_2$, —S(=O)$_{1-2}N(heteroaryl)_2$, —S(=O)$_{1-2}N(C_{1-8}$-aliphatic-$C_{3-12}$-cycloaliphatic)$_2$, —S(=O)$_{1-2}N(C_{1-8}$-aliphatic-aryl)$_2$, —S(=O)$_{1-2}N(C_{1-8}$-aliphatic-heteroaryl)$_2$, —OS(=O)$_{1-2}C_{1-8}$-aliphatic, —OS(=O)$_{1-2}C_{3-12}$-cycloaliphatic, —OS(=O)$_{1-2}$aryl, —OS(=O)$_{1-2}$heteroaryl, —OS(=O)$_{1-2}C_{1-8}$-aliphatic-$C_{3-12}$-cycloaliphatic, —OS(=O)$_{1-2}C_{1-8}$-aliphatic-aryl, —OS(=O)$_{1-2}C_{1-8}$-aliphatic-heteroaryl, —OS(=O)$_{1-2}$OH, —OS(=O)$_{1-2}OC_{1-8}$-aliphatic, —OS(=O)$_{1-2}OC_{3-12}$-cycloaliphatic, —OS(=O)$_{1-2}$Oaryl, —OS(=O)$_{1-2}$Oheteroaryl, —OS(=O)$_{1-2}OC_{1-8}$-aliphatic-$C_{3-12}$-cycloaliphatic, —OS(=O)$_{1-2}OC_{1-8}$-aliphatic-aryl, —OS(=O)$_{1-2}OC_{1-8}$-aliphatic-heteroaryl, —OS(=O)$_{1-2}NH_2$, —OS(=O)$_{1-2}NHC_{1-8}$-aliphatic, —OS(=O)$_{1-2}NHC_{3-12}$-cycloaliphatic, —OS(=O)$_{1-2}$NHaryl, —OS(=O)$_{1-2}$NHheteroaryl, —OS(=O)$_{1-2}NHC_{1-8}$-aliphatic-$C_{3-12}$-cycloaliphatic, —OS(=O)$_{1-2}NHC_{1-8}$-aliphatic-aryl, —OS(=O)$_{1-2}NHC_{1-8}$-aliphatic-heteroaryl, —OS(=O)$_{1-2}N(C_{1-8}$- aliphatic)$_2$, —OS(=O)$_{1-2}$N(C$_{3-12}$-cycloaliphatic)$_2$, —OS(=O)$_{1-2}$N(aryl)$_2$, —OS(=O)$_{1-2}$N(heteroaryl)$_2$, —OS(=O)$_{1-2}$N(C$_{1-8}$-aliphatic-C$_{3-12}$-cycloaliphatic)$_2$, —OS(=O)$_{1-2}$N(C$_{1-8}$-aliphatic-aryl)$_2$ or —OS(=O)$_{1-2}$N(C$_{1-8}$-aliphatic-heteroaryl)$_2$.

More preferably, R$_4$ is —C$_{1-8}$-aliphatic, —C$_{3-12}$-cycloaliphatic, -aryl, -heteroaryl, —O—C$_{1-8}$-aliphatic, —O—C$_{3-12}$-cycloaliphatic, —O-aryl, —O-heteroaryl, —NH—C$_{1-8}$-aliphatic, —NH—C$_{3-12}$-cycloaliphatic, —NH-aryl, —NH-heteroaryl, —N(C$_{1-8}$-aliphatic)$_2$, —N(C$_{3-12}$-cycloaliphatic)$_2$, —N(aryl)$_2$, —N(heteroaryl)$_2$, —S—C$_{1-8}$-aliphatic, —S—C$_{3-12}$-cycloaliphatic, —S-aryl or —S-heteroaryl.

Still more preferably, R$_4$ represents —C$_{3-12}$-cycloaliphatic, -aryl, -heteroaryl, —O—C$_{1-8}$-aliphatic, —O—C$_{3-12}$-cycloaliphatic, —O-aryl, —O-heteroaryl, —NH—C$_{1-8}$-aliphatic, —NH—C$_{3-12}$-cycloaliphatic, —NH-aryl, —NH-heteroaryl, —N(C$_{1-8}$-aliphatic)$_2$, —N(C$_{3-12}$-cycloaliphatic)$_2$, —N(aryl)$_2$, —N(heteroaryl)$_2$, —S—C$_{1-8}$-aliphatic, —S—C$_{3-12}$-cycloaliphatic or —S-aryl or —S-heteroaryl.

Particularly preferably, R$_4$ represents -aryl (preferably -phenyl, optionally substituted), —O-aryl (preferably —O-phenyl, optionally substituted) or -heteroaryl (preferably -indolyl or -indanyl, in each case optionally substituted). In a particularly preferred embodiment, R$_4$ represents -aryl, -heteroaryl, —C$_{3-12}$-cycloaliphatic, —O-aryl, —O-heteroaryl, —O—C$_{3-12}$-cycloaliphatic, —NH-aryl, —NH-heteroaryl, —NH—C$_{3-12}$-cycloaliphatic, —N(aryl)$_2$, —N(heteroaryl)$_2$, —N(C$_{3-12}$-cycloaliphatic)$_2$, —S-aryl, —S-heteroaryl or —S—C$_{3-12}$-cycloaliphatic; -aryl, -heteroaryl and —C$_{3-12}$-cycloaliphatic being particularly preferred.

Preferred examples of R$_4$ are shown below:

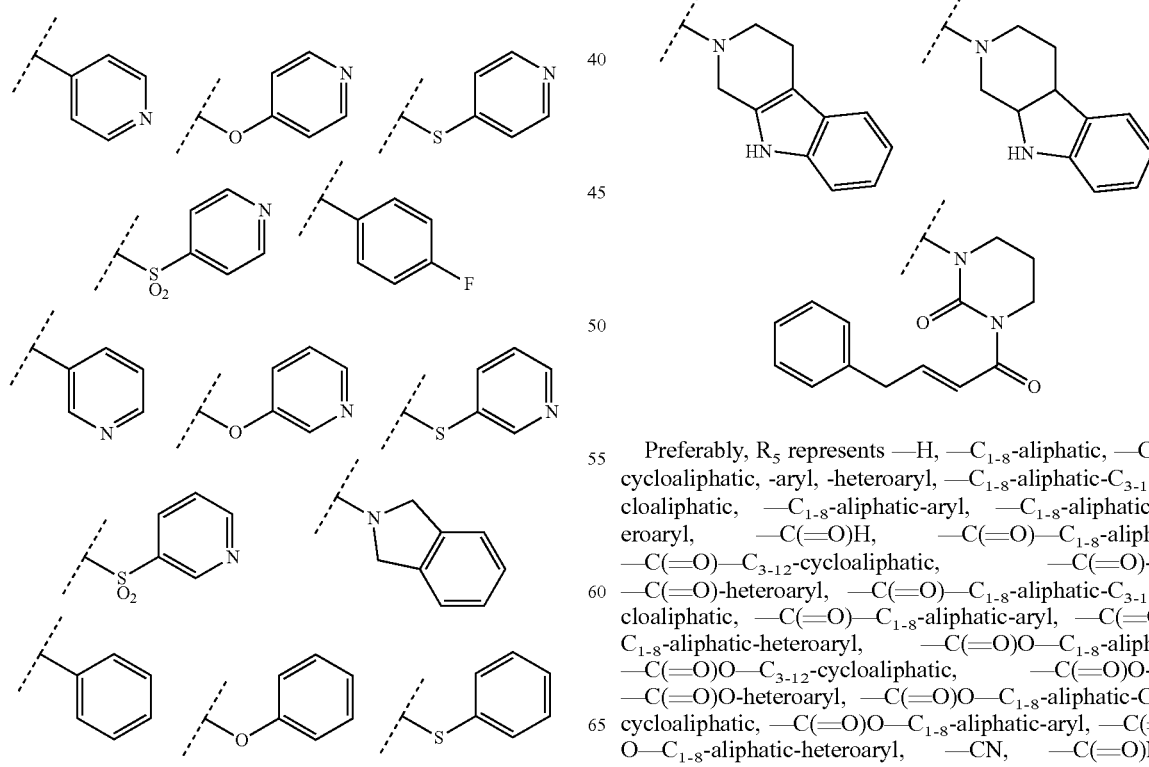

Preferably, R$_5$ represents —H, —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C(=O)H, —C(=O)—C$_{1-8}$-aliphatic, —C(=O)—C$_{3-12}$-cycloaliphatic, —C(=O)-aryl, —C(=O)-heteroaryl, —C(=O)—C$_{1-8}$-aliphatic-C$_{3-12}$-cycloaliphatic, —C(=O)—C$_{1-8}$-aliphatic-aryl, —C(=O)—C$_{1-8}$-aliphatic-heteroaryl, —C(=O)O—C$_{1-8}$-aliphatic, —C(=O)O—C$_{3-12}$-cycloaliphatic, —C(=O)O-aryl, —C(=O)O-heteroaryl, —C(=O)O—C$_{1-8}$-aliphatic-C$_{3-12}$-cycloaliphatic, —C(=O)O—C$_{1-8}$-aliphatic-aryl, —C(=O)O—C$_{1-8}$-aliphatic-heteroaryl, —CN, —C(=O)NH$_2$, —C(=O)—NH—C$_{1-8}$-aliphatic, —C(=O)NH—C$_{3-12}$-cycloaliphatic, —C(=O)NH-aryl, —C(=O)NH-heteroaryl, —C(=O)—NH—C$_{1-8}$-aliphatic-C$_{3-12}$-cycloaliphatic, —C(=O)NH—C$_{1-8}$-aliphatic-aryl, —C(=O)NH—C$_{1-8}$-aliphatic-heteroaryl,—C(=O)N(C$_{1-8}$-aliphatic)$_2$,—C(=O)N(C$_{3-12}$-cycloaliphatic)$_2$, —C(=O)N(aryl)$_2$, —C(=O)N-(heteroaryl)$_2$, —C(=O)N(C$_{1-8}$-aliphatic-C$_{3-12}$-cycloaliphatic)$_2$, —C(=O)N(C$_{1-8}$-aliphatic-aryl)$_2$ or —C(=O)—N(C$_{1-8}$-aliphatic-heteroaryl)$_2$.

More preferably, R$_5$ is chosen from —H, —C$_{1-8}$-aliphatic, —C$_{3-12}$-cycloaliphatic, —C$_{1-8}$-aliphatic-C$_{3-12}$-cycloaliphatic, —C$_{1-8}$-aliphatic-aryl, —C$_{1-8}$-aliphatic-heteroaryl, -aryl and -heteroaryl.

Preferred examples of R$_5 \ne$ —H are shown below:

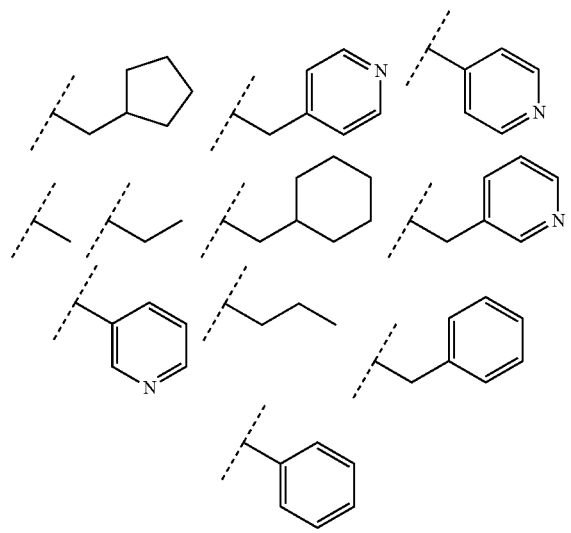

In a preferred embodiment, R$_5$ represents —H.

Particularly preferred embodiments of the compounds according to the invention are summarized in the following table:

|  | preferably | more preferably | still more preferably |
|---|---|---|---|
| R$_1$ | —H or —C$_{1-8}$-aliphatic | —H or C$_{1-8}$-alkyl | —H or —CH$_3$ |
| R$_2$ | —H or —C$_{1-8}$-aliphatic | —H or C$_{1-8}$-alkyl | —H or —CH$_3$ |
| R$_3$ | —C$_{1-8}$-aliphatic; aryl, optionally substituted; or heteroaryl, optionally substituted | —C$_{1-8}$-alkyl; -phenyl, optionally substituted; or -thienyl, optionally substituted | -butyl, -phenyl, -methoxyphenyl, or -fluorophenyl |
| R$_4$ | -aryl, —O-aryl, —S-aryl, -heteroaryl, —O—C$_{1-8}$-aliphatic-aryl, —O—C$_{3-12}$-cycloaliphatic | -phenyl, —O-phenyl, —S-phenyl, in each case optionally substituted; indolyl, optionally substituted, isoindolyl, optionally substituted; —O—C$_{3-12}$-cycloalkyl | -phenyl, —O-phenyl, —S-phenyl, in each case optionally substituted; indolyl, optionally substituted; isoindolyl, optionally substituted; —O—C$_{3-12}$-cycloalkyl |
| R$_5$ | —H | —H | —H |
| Y$_1$,Y$_1$', Y$_2$,Y$_2$', Y$_3$,Y$_3$', Y$_4$,Y$_4$' | —H | —H |  |

For the purpose of the description, hydrocarbon radicals are divided into aliphatic hydrocarbon radicals on the one hand and aromatic hydrocarbon radicals on the other hand.

Aliphatic hydrocarbon radicals are in their turn divided into non-cyclic aliphatic hydrocarbon radicals on the one hand (="aliphatic") and cyclic aliphatic hydrocarbon radicals, i.e. alicylic hydrocarbon radicals, on the other hand (="cycloaliphatic"). Cycloaliphatics can be monocyclic or multicyclic. Alicyclic hydrocarbon radicals ("cycloaliphatic") include both pure aliphatic carbocyclyls and aliphatic heterocyclyls, i.e. —if not expressly specified— "cycloaliphatic" includes pure aliphatic carbocyclyls (e.g. cyclohexyl), pure aliphatic heterocyclyls (e.g. piperidyl or piperazyl) and non-aromatic, multicyclic, optionally mixed systems (e.g. decalinyl, decahydroquinolinyl).

Aromatic hydrocarbon radicals are in their turn divided into carbocyclic aromatic hydrocarbons on the one hand (="aryl") and heterocyclic aromatic hydrocarbon radicals on the other hand (="heteroaryl").

The assignment of multicyclic, at least partly aromatic systems preferably depends on whether at least one aromatic ring of the multicyclic system contains at least one hetero atom (conventionally N, O or S) in the ring. If at least one such hetero atom is present in this ring, the radical is preferably a "heteroaryl" (even if a further carbocyclic aromatic or non-aromatic ring with or without a hetero atom is present optionally as an additionally present ring of the multicyclic system); if such a hetero atom is present in none of the optionally several aromatic rings of the multicyclic system, the radical is preferably "aryl" (even if a ring hetero atom is present in an optionally additionally present non-aromatic ring of the multicyclic system).

Within the multicyclic substituents, the following priority of assignment accordingly preferably applies: heteroaryl>aryl>cycloaliphatic. The following substituent is therefore preferably interpreted as "aryl":

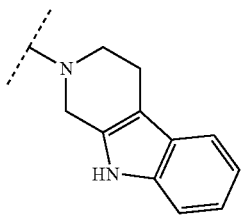

For the purpose of the description, monovalent and polyvalent, e.g. divalent hydrocarbon radicals are not differentiated with respect to terminology, i.e. "C$_{1-3}$-aliphatic" includes, depending on the sense, e.g. both —C$_{1-3}$-alkyl, —C$_{1-3}$-alkenyl and —C$_{1-3}$-alkynyl and e.g. —C$_{1-3}$-alkylene-, —C$_{1-3}$-alkenylene- and —C$_{1-3}$-alkynylene-.

Preferably, "aliphatic" is in each case a branched or unbranched, saturated or a mono- or polyunsaturated, unsubstituted or mono- or polysubstituted, aliphatic hydrocarbon radical. If aliphatic is mono- or polysubstituted, the substituents independently of each other are chosen from the group consisting of —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)—N(R$_0$)$_2$, —SH, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC (=O)—NHR$_0$, —NH—C(=O)N(R$_0$)$_2$, —Si(R$_0$)$_3$, —PO(OR$_0$)$_2$. "Aliphatic" thus includes acyclic saturated or unsaturated hydrocarbon radicals, which can be branched or straight-chain, i.e. alkanyls, alkenyls and alkynyls. In this context, alkenyls have at least one C=C double bond and alkynyls have at least one C≡C triple bond. Preferred unsubstituted monovalent aliphatics include —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH$_2$CH$_2$CH$_2$—CH$_2$CH$_3$ and —CH$_2$CH$_2$—CH$_2$CH$_2$CH$_2$CH$_3$; but also —CH=CH$_2$, —C≡CH, —CH$_2$CH=CH$_2$, —CH=CHCH$_3$, —CH$_2$C≡CH, —C≡CCH$_3$ and —CH=CHCH=CH$_2$. Preferred unsubstituted divalent aliphatics include —CH$_2$—, —CH$_2$CH$_2$—, —CH$_2$CH(CH$_3$)—, —CH(CH$_3$)—CH$_2$—, —CH$_2$CH$_2$CH$_2$—, —CH(CH$_3$)CH$_2$CH$_2$—, —CH$_2$CH(CH$_3$)—CH$_2$—, —CH$_2$CH$_2$CH(CH$_3$)—, —CH(CH$_2$CH$_3$)CH$_2$— and —CH$_2$CH$_2$—CH$_2$CH$_2$—; but also —CH=CH—, C≡C—, —CH$_2$CH=CH—, —CH=CHCH$_2$—, —CH$_2$C≡C— and —C≡CCH$_2$—. Preferred substituted monovalent aliphatics include —CH$_2$F, —CHF$_2$, —CF$_3$, —CH$_2$CF$_3$, —CF$_2$CF$_3$, —CH$_2$OH, —CH$_2$CH$_2$OH, —CH$_2$CHOHCH$_3$, —CH$_2$OCH$_3$ and CH$_2$CH$_2$OCH$_3$. Preferred substituted divalent aliphatics include —CF$_2$—, —CF$_2$CF$_2$—, —CH$_2$CHOH—, —CHOHCH$_2$— and —CH$_2$CHOHCH$_2$—. Methyl, ethyl, n-propyl and n-butyl are particularly preferred Preferably, cycloaliphatic is in each case a saturated or a mono- or polyunsaturated, unsubstituted or mono- or polysubstituted, aliphatic (i.e. not aromatic), mono- or multicyclic hydrocarbon radical, The number of ring carbon atoms is preferably in the stated range (i.e. a "C$_{3-8}$"-cycloaliphatic preferably has 3, 4, 5, 6, 7 or 8 ring carbon atoms). For the purpose of the description, "C$_{3-8}$-cycloaliphatic" is preferably a cyclic hydrocarbon having 3, 4, 5, 6, 7 or 8 ring carbon atoms, saturated or unsaturated, but not aromatic, one or two carbon atoms independently of each other optionally being replaced by a hetero atom S, N or O. If cycloalkyl is mono- or polysubstituted, the substituents independently of each other are chosen from the group consisting of —F, —Cl, —Br, —I, —CN, —NO$_2$, —CHO, =O, —R$_0$, —C(=O)R$_0$, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NH—C(=O)N(R$_0$)$_2$, —Si(R$_0$)$_3$, —PO(OR$_0$)$_2$. C$_{3-8}$-Cycloaliphatic is advantageously chosen from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl. If cycloaliphatic is substituted by R$_0$ and R$_0$ represents aryl or heteroaryl, this aryl or heteroaryl substituent can be bonded via a bond to cycloaliphatic, but it can also be bonded via two vicinal ring atoms of the cycloaliphatic, i.e. fused.

Preferably, in connection with "aliphatic" or "cycloaliphatic", "mono- or polysubstituted" is understood as meaning substitution once or several times, e.g. once, twice, three times or four times, of one or more hydrogen atoms by —F, —Cl, —Br, —I, —OH, —OC$_{1-6}$-alkyl, —OC(=O)C$_{1-6}$-alkyl, —SH, —NH$_2$, —NHC$_{1-6}$-alkyl, —N(C$_{1-6}$-alkyl)$_2$, —C(=O)OC$_{1-6}$-alkyl or —C(=O)OH. Compounds wherein "aliphatic substituted" or "cycloaliphatic substituted" means aliphatic or cycloaliphatic substituted by —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$ are preferred. Particularly preferred substituents are —F, —Cl, —OH, —SH, —NH$_2$ and —C(=O)OH.

Polysubstituted radicals are to be understood as meaning those radicals which are polysubstituted, e.g. di- or trisubstituted, either on different or on the same atoms, for example trisubstituted on the same C atom, as in the case of —CF$_3$ or —CH$_2$CF$_3$, or at different places, as in the case of —CH(OH)—CH=CH—CHCl$_2$. Polysubstitution can be with the same or with various substituents. A substituent can optionally also be substituted in its turn; thus -Oaliphatic, inter alia, also includes —O—CH$_2$CH$_2$O—CH$_2$CH$_2$—OH. It is preferable for aliphatic or cycloaliphatic to be substituted by —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$. It is very particularly preferable for aliphatic or cycloaliphatic to be substituted by —OH, —OCH$_3$ or —OC$_2$H$_5$.

Preferably, aryl in each case independently represents a carbocyclic ring system having at least one aromatic ring, but without hetero atoms in this ring, wherein the aryl radicals can optionally be fused with further saturated, (partially) unsaturated or aromatic ring systems, which in their turn can have one or more hetero ring atoms, in each case independently of each other chosen from N, O and S, and wherein each aryl radical can be unsubstituted or mono- or polysubstituted, wherein the substituents on aryl can be identical or different and can be in any desired and possible position of the aryl. Preferred aryls are phenyl, naphthyl, anthracenyl, phenanthrenyl, fluoranthenyl, fluorenyl, indanyl and tetralinyl. Phenyl and naphthyl are particularly preferred. If aryl is mono- or polysubstituted, the substituents on aryl can be identical or different and can be in any desired and possible position of the aryl, and are independently of each other chosen from the group consisting of —F, —Cl, —Br, —I, —CN, —NO$_2$, —CHO, =O, —R$_0$, —C(=O)R$_0$, —C(=O)OH, —C(=O)OR$_0$, —C(=O)—NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)—NHR$_0$, —OC(=O)N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, —NH—C(=O)N(R$_0$)$_2$, —Si(R$_0$)$_3$, —PO(OR$_0$)$_2$. Preferred substituted aryls are 2-fluoro-phenyl, 3-fluoro-phenyl, 4-fluoro-phenyl, 2,3-difluoro-phenyl, 2,4-difluoro-phenyl, 3,4-difluoro-phenyl, 2-chloro-phenyl, 3-chloro-phenyl, 4-chloro-phenyl, 2,3-dichloro-phenyl, 2,4-dichloro-phenyl, 3,4-dichloro-phenyl, 2-methoxy-phenyl, 3-methoxy-phenyl, 4-methoxy-phenyl, 2,3-dimethoxy-phenyl, 2,4-dimethoxy-phenyl, 3,4-dimethoxy-phenyl, 2-methyl-phenyl, 3-methyl-phenyl, 4-methyl-phenyl, 2,3-dimethyl-phenyl, 2,4-dimethyl-phenyl and 3,4-dimethyl-phenyl.

Preferably, heteroaryl represents a 5-, 6- or 7-membered cyclic aromatic radical which contains 1, 2, 3, 4 or 5 hetero atoms, wherein the hetero atoms are identical or different and are nitrogen, oxygen or sulfur and the heterocyclyl can be unsubstituted or mono- or polysubstituted; wherein in the case of substitution on the heterocyclyl the substituents can be identical or different and can be in any desired and possible position of the heteroaryl; and wherein the heterocyclyl can also be part of a bi- or polycyclic system. Preferably, "heteroaryl" is chosen from the group consisting of pyrrolyl, indolyl, furyl (furanyl), benzofuranyl, thienyl (thiophenyl), benzothienyl, benzothiadiazolyl, benzooxadiazolyl, benzothiazolyl, benzooxazolyl, benzotriazolyl, benzodioxolanyl, benzodioxanyl, phthalazinyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, where bonding can be via any desired and possible ring member of the heteroaryl radical. If heteroaryl is mono- or polysubstituted, the substituents on heteroaryl can be identical or different and in any desired and possible position of the heteroaryl, and are independently of each other chosen from the group consisting of —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O—, —NHC(=O)R$_0$, —NHC(=O)OR$_0$, —NHC(=O)NH$_2$, —NHC(=O)—NHR$_0$, —NH—C(=O)N(R$_0$)$_2$, —Si(R$_0$)$_3$, —PO(OR$_0$)$_2$.

With respect to "aryl" or "heteroaryl", "mono- or polysubstituted" is understood as meaning substitution once or several times, e.g. twice, three times, four times or five times, of one or more hydrogen atoms of the ring system.

The substituents on aryl and heteroaryl are particularly preferably in each case independently of each other chosen from —F, —Cl, —Br, —I, —CN, —CHO, —CO$_2$H, —NH$_2$, —NO$_2$, —NHR$_0$, —N(R$_0$)$_2$, —N$^+$(R$_0$)$_3$, —N$^+$(R$_0$)$_2$O$^-$, —SH, —SR$_0$, —OH, —OR$_0$, —C(=O)R$_0$, —CO$_2$R$_0$, —C(=O)NH$_2$, —C(=O)NHR$_0$, —C(=O)N(R$_0$)$_2$, —S(=O)$_{1-2}$R$_0$, —S(=O)$_{1-2}$NH$_2$, —SO$_3$H, =O or —R$_0$. Preferred substituents are —F, —Cl, —Br, —I, —OH, —OC$_{1-6}$-alkyl, —O—C(=O)—C$_{1-6}$-alkyl, —SH, —NH$_2$, —NHC$_{1-6}$-alkyl, —N(C$_{1-6}$-alkyl)$_2$, —C(=O)OC$_{1-6}$-alkyl or —C(=O)OH. Compounds wherein "aryl substituted" or "heteroaryl substituted" means aryl or heteroaryl substituted by —F, —Cl, —Br, —I, —CN, —CH$_3$, —C$_2$H$_5$, —NH$_2$, —NO$_2$, —SH, —CF$_3$, —OH, —OCH$_3$, —OC$_2$H$_5$ or —N(CH$_3$)$_2$ are preferred. Particularly preferred substituents are —F, —Cl, —OH, —SH, —NH$_2$ and —C(=O)OH.

The compounds according to the invention can be in the form of an individual stereoisomer or mixture thereof, the free compounds and/or their physiologically acceptable salts and/or solvates.

The compounds according to the invention can be chiral or achiral, depending on the substitution pattern.

Depending on the substitution with respect to the cyclohexane ring, the compounds according to the invention can be isomers in which the substitution pattern in the 1,4-position (1-position: >C(NR$_1$R)R$_3$; 4-position: >COHR$_5$CH$_2$R$_4$) can also be called syn/anti. "Syn/anti isomers" are a sub-group of stereoisomers (configuration isomers).

In a preferred embodiment, the diastereomer excess of the syn isomer is at least 50% de, more preferably at least 75% de, still more preferably at least 90% de, most preferably at least 95% de and in particular at least 99% de. In another preferred embodiment, the diastereomer excess of the anti isomer is at least 50% de, more preferably at least 75% de, still more preferably at least 90% de, most preferably at least 95% de and in particular at least 99% de.

Suitable methods for separation of the isomers (diastereomers) are known to the person skilled in the art. Examples which may be mentioned are column chromatography, preparative HPLC and crystallization processes.

If the compounds according to the invention are chiral, they are preferably in the form of the racemate or in an enriched form of one enantiomer. In a preferred embodiment, the enantiomer excess (ee) of the S enantiomer is at least 50% ee, more preferably at least 75% ee, still more preferably at least 90% ee, most preferably at least 95% ee and in particular at least 99% ee. In another preferred embodiment, the enantiomer excess (ee) of the R enantiomer is at least 50% ee, more preferably at least 75% ee, still more preferably at least 90% ee, most preferably at least 95% ee and in particular at least 99% de.

Suitable methods for separation of the enantiomers are known to the person skilled in the art. Examples which may be mentioned are preparative HPLC on chiral stationary phases and conversion into diastereomeric intermediates. The conversion into diastereomeric intermediates can be carried out, for example, as salt formation with the aid of chiral, enantiomerically pure acids. After the separation of the diastereomers formed in this way, the salt can then be converted back into the free base or another salt.

If not expressly specified, any reference to the compounds according to the invention includes all the isomers (e.g. stereoisomers, diastereomers, enantiomers) in any desired mixing ratio.

If not expressly stated, any reference to the compounds according to the invention includes the free compounds (i.e. the forms which are not in the form of a salt) and all physiologically acceptable salts.

For the purpose of the description, physiologically acceptable salts of the compounds according to the invention are in the form of salts with anions or acids of the particular compound with inorganic or organic acids which are physiologically acceptable—in particular when used in humans and/or mammals.

Examples of physiologically acceptable salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethylbenzoic acid, α-liponic acid, acetylglycine, acetylsalicylic acid, hippuric acid and/or aspartic acid. The hydrochloride, the citrate and the hemicitrate are particularly preferred.

Physiologically acceptable salts with cations or bases are salts of the particular compound—as the anion with at least one, preferably inorganic cation—which are physiologically acceptable—in particular when used in humans and/or mammals. The salts of alkali metals and alkaline earth metals but also ammonium salts are particularly preferred, but in particular (mono)- or (di)sodium, (mono)- or (di)potassium, magnesium or calcium salts.

Preferred embodiments of the compounds according to the invention are in each case explained in the following. If not expressly specified, all the particular definitions explained above for the substituents and the particular preferred embodiments thereof apply accordingly and are therefore not repeated.

Preferred embodiments of the compounds of the general formula (1) according to the invention have the general formula (2), (3), (4), (5), (6), (7), (8) or (9).

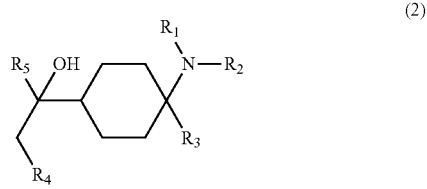

(2)

(3)

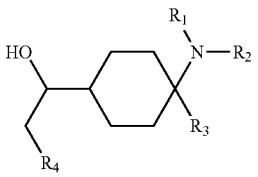

(4)

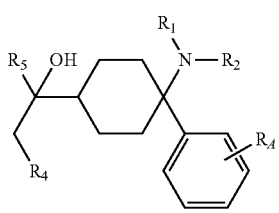

(5)

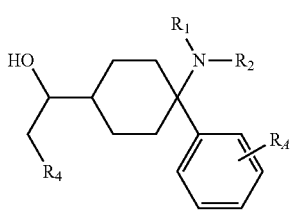

(6)

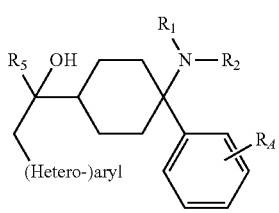

(7)

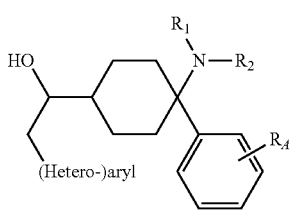

(8)

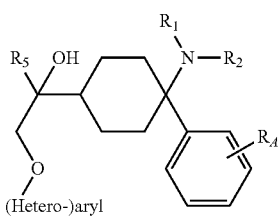

(9)

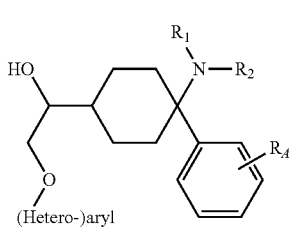

wherein, if present, $R_A$ represents —H, —F, —Cl, —CN, —NO$_2$ or —OCH$_3$ and (Hetero-)aryl represents heteroaryl or aryl, in each case unsubstituted or mono- or polysubstituted.

The compounds according to the invention are defined by substituents, for example by $R_1$, $R_2$ and $R_3$ (substituents of the 1st generation), which in their turn are optionally substituted (substituents of the 2nd generation). Depending on the definition, these substituents of the substituents can in their turn be substituted again (substituents of the 3rd generation). For example, if $Y_1$=$R_0$, wherein $R_0$=—C$_{1-8}$-aliphatic (substituent of the 1st generation), —C$_{1-8}$-aliphatic can in its turn be substituted, e.g. by —OR$_0$, wherein $R_0$=-aryl (substituent of the 2nd generation). The functional group —C$_{1-8}$-aliphatic-Oaryl results from this. -Aryl can then in its turn be substituted again, e.g. by —Cl (substituents of the 3rd generation). The functional group —C$_{1-8}$-aliphatic-Oaryl-Cl overall then results from this.

In a preferred embodiment, however, the substituents of the 3rd generation cannot be substituted again, i.e. there are then no substituents of the 4th generation.

In another preferred embodiment, however, the substituents of the 2nd generation cannot be substituted again, i.e. there are then already no substituents of the 3rd generation. In other words, in this embodiment the functional groups for $R_0$ to $R_5$ can in each case be optionally substituted, but the particular substituents cannot then in their turn be substituted again.

In another preferred embodiment, the substituents of the 1st generation already cannot be substituted again, i.e. there are then neither substituents of the 2nd nor substituents of the 3rd generation. In other words, in this embodiment the functional groups for $R_0$ to $R_5$ in each case cannot be substituted.

Very particularly preferred compounds are those from the group:

1-(4-(dimethylamino)-4-phenylcyclohexyl)-2-phenylethanol;
1-(4-(dimethylamino)-4-phenylcyclohexyl)-2-phenoxyethanol;
1-(4-(dimethylamino)-4-phenylcyclohexyl)-2-(1H-indol-1-yl)ethanol;
1-(4-(dimethylamino)-4-phenylcyclohexyl)-2-(isoindolin-2-yl)ethanol,
1-(4-(dimethylamino)-4-phenylcyclohexyl)-2-(4-fluorophenyl)ethanol;
1-(4-(dimethylamino)-4-(3-fluorophenyl)cyclohexyl)-2-phenylethanol;
1-(4-(dimethylamino)-4-(3-methoxyphenyl)cyclohexyl)-2-phenylethanol;
1-(4-(dimethylamino)-4-(thiophen-2-yl)cyclohexyl)-2-phenylethanol;
1-(4-butyl-4-(dimethylamino)cyclohexyl)-2-phenylethanol;
1-cyclopentyl-2-(4-(dimethylamino)-4-phenylcyclohexyl)-3-phenylpropan-2-ol;
1-(4-(dimethylamino)-4-phenylcyclohexyl)-1-phenyl-2-(pyridin-4-yl)ethanol;
1-(4-(dimethylamino)-4-phenylcyclohexyl)-2-(phenylthio)ethanol;
1-(4-(dimethylamino)-4-phenylcyclohexyl)-2-(phenylsulfonyl)ethanol;

2-(cyclohexyloxy)-1-(4-(dimethylamino)-4-phenylcyclohexyl)ethanol;
2-(benzyloxy)-1-(4-(dimethylamino)-4-phenylcyclohexyl)ethanol;
1-(4-(dimethylamino)-4-phenylcyclohexyl)-2-phenethoxyethanol;
2-((1H-indol-3-yl)methoxy)-1-(4-(dimethylamino)-4-phenylcyclohexyl)ethanol;
2-(2-(1H-indol-3-yl)ethoxy)-1-(4-(dimethylamino)-4-phenylcyclohexyl)ethanol;
1-(4-(dimethylamino)-4-phenylcyclohexyl)-2-((2-(triethylsilyl)-1H-indol-3-yl)methoxy)ethanol;
1-(2-(4-(dimethylamino)-4-(3-fluorophenyl)cyclohexyl)-2-hydroxyethyl)piperidin-2-one;
2-(4,4a-dihydro-1H-pyrido[3,4-b]indol-2(3H,9H,9aH)-yl)-1-(4-(dimethylamino)-4-(3-fluorophenyl)cyclohexyl)ethanol;
1-cinnamoyl-3-(2-(4-(dimethylamino)-4-(3-fluorophenyl)cyclohexyl)-2-hydroxyethyl)tetrahydropyrimidin-2(1H)-one;
2-(4-(dimethylamino)-4-phenylcyclohexyl)-1-phenylpropan-2-ol;
2-(4-(dimethylamino)-4-phenylcyclohexyl)-1,3-diphenylpropan-2-ol;
2-(4-(dimethylamino)-4-phenylcyclohexyl)-1-phenyl-3-(pyridin-2-yl)propan-2-ol;
2-(4-(dimethylamino)-4-phenylcyclohexyl)-1-phenyl-3-(pyridin-3-yl)propan-2-ol; and
2-(4-(dimethylamino)-4-phenylcyclohexyl)-1-phenyl-3-(pyridin-4-yl)propan-2-ol;
and physiologically acceptable salts and/or solvates thereof.

Further preferred compounds are
2-(9-(benzenesulfonyl)-2,3,4,9-tetrahydro-1H-beta-carbolin-2-yl)-1-(4-dimethylamino-4-phenylcyclohexyl)ethanol;
2-(2,3-dihydro-1H-isoindol-2-yl)-1-(4-(dimethylamino)-4-phenylcyclohexyl)ethanol;
2-cyclohexyloxy-1-(4-dimethylamino-4-thiophen-2-ylcyclohexyl)ethanol;
2-(4-dimethylamino-4-phenylcyclohexyl)-1-phenoxypropan-2-ol; and
3-((3S)-3-(4-dimethylamino-4-phenylcyclohexyl)-3-hydroxy-prop-1-ynyl)-1H-indole-1-carboxylic acid tert-butyl ester;
and physiologically acceptable salts thereof.

The compounds according to the invention act, for example, on the ORL1 receptor relevant in connection with various diseases, so that they are suitable as a pharmaceutical active compound in a medicament.

The invention therefore also provides medicaments which contain at least one compound according to the invention and optionally suitable additives and/or auxiliary substances and/or optionally further active compounds.

The compounds according to the invention have a comparable affinity for the μ opioid or for the ORL1 receptor to the compounds which are disclosed as example compounds in WO 2004043967. Compared with these compounds, however, they have a higher solubility and are therefore suitable in particular for the development of medicaments.

The medicaments according to the invention optionally contain, in addition to at least one compound according to the invention, suitable additives and/or auxiliary substances, that is to say also carrier materials, fillers, solvents, diluents, dyestuffs and/or binders, and can be administered as liquid medicament forms in the form of injection solutions, drops or juices or as semi-solid medicament forms in the form of granules, tablets, pellets, patches, capsules, plasters/spray-on plasters or aerosols. The choice of auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example on the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Compounds according to the invention in a depot, in dissolved form or in a plaster, optionally with the addition of agents which promote penetration through the skin, are suitable formulations for percutaneous administration. Formulation forms which can be used orally or percutaneously can release the compounds according to the invention in a delayed manner. The compounds according to the invention can also be used in parenteral long-term depot forms, such as e.g. implants or implanted pumps. In principle, other further active compounds known to the person skilled in the art can be added to the medicaments according to the invention.

The amount of active compound to be administered to patients varies as a function of the weight of the patient, of the mode of administration, the indication and the severity of the disease. 0.00005 to 50 mg/kg, preferably 0.001 to 0.5 mg/kg of at least one compound according to the invention are conventionally administered.

For all the above forms of the medicaments according to the invention, it is particularly preferable if the medicament also contains, in addition to at least one compound according to the invention, a further active compound, in particular an opioid, preferably a potent opioid, in particular morphine, or an anaesthetic, preferably hexobarbital or halothane.

In a preferred form of the medicament, a compound according to the invention contained therein is in the form of a pure diastereomer and/or enantiomer.

The ORL1 receptor has been identified in particular in the pain event. Compounds according to the invention can accordingly be used for the preparation of a medicament for treatment of pain, in particular acute, neuropathic or chronic pain.

The invention therefore also provides the use of a compound according to the invention for the preparation of a medicament for treatment of pain, in particular acute, visceral, neuropathic or chronic pain.

The invention also provides the use of a compound according to the invention for the preparation of a medicament for treatment of anxiety states, of stress and syndromes associated with stress, depression, epilepsy, Alzheimer's disease, senile dementia, general cognitive dysfunctions, learning and memory disorders (as a nootropic), withdrawal symptoms, alcohol and/or drug and/or medicament abuse and/or dependency, sexual dysfunctions, cardiovascular diseases, hypotension, hypertension, tinnitus, pruritus, migraine, impaired hearing, lack of intestinal motility, impaired food intake, anorexia, obesity, locomotor disorders, diarrhoea, cachexia, urinary incontinence or as a muscle relaxant, anti-convulsive or anaesthetic or for co-administration in treatment with an opioid analgesic or with an anaesthetic, for diuresis or antinatriuresis, anxiolysis, for modulation of motor activity, for modulation of neurotransmitter secretion and treatment of neurodegenerative diseases associated therewith, for treatment of withdrawal symptoms and/or for reduction of the addiction potential of opioids.

In this context, in one of the above uses it may be preferable for a compound which is used to be in the form of a pure diastereomer and/or enantiomer, a racemate or a non-equimolar or equimolar mixture of the diastereomers and/or enantiomers.

The invention also provides a method for the treatment, in particular in one of the abovementioned indications, of a non-human mammal or a human requiring treatment of pain, in particular chronic pain, by administration of a therapeutically active dose of a compound according to the invention, or of a medicament according to the invention.

The present invention also provides a process for the preparation of the compounds according to the invention as described in the following description and examples. In this context, a process for the preparation of a compound according to the invention wherein compounds of the general formula I can be obtained by addition of suitable nucleophiles on to suitable carbonyl compounds is suitable in particular. In the case where $R^5$ differs from —H, either $R^5$ or $R^4$—$CH_2$ can be introduced in a varying sequence (equation 1):

Equation 1

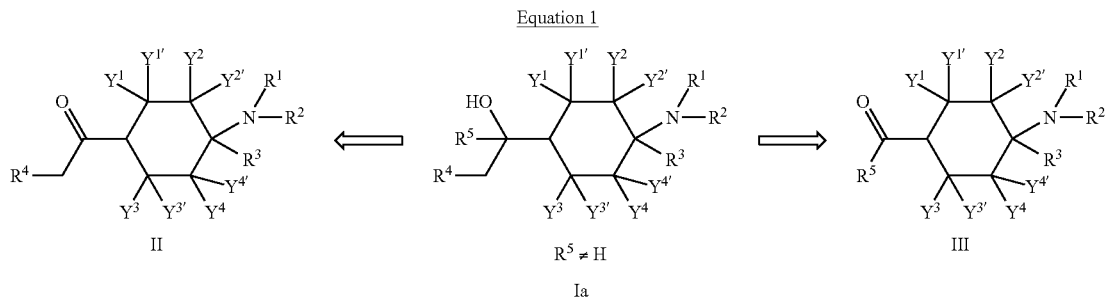

In this context, the ketones II or III can be introduced in an intermediate synthesis by addition of suitable carbon nucleophiles on to aldehydes VI. The alcohol V obtained can then be converted into the ketones II or III by means of oxidation methods familiar to the person skilled in the art. Alternatively to this, carbonyl compounds of the Weinreb amide type (IV) can be converted into ketones by substitution with carbon nucleophiles (equation 2):

Equation 2

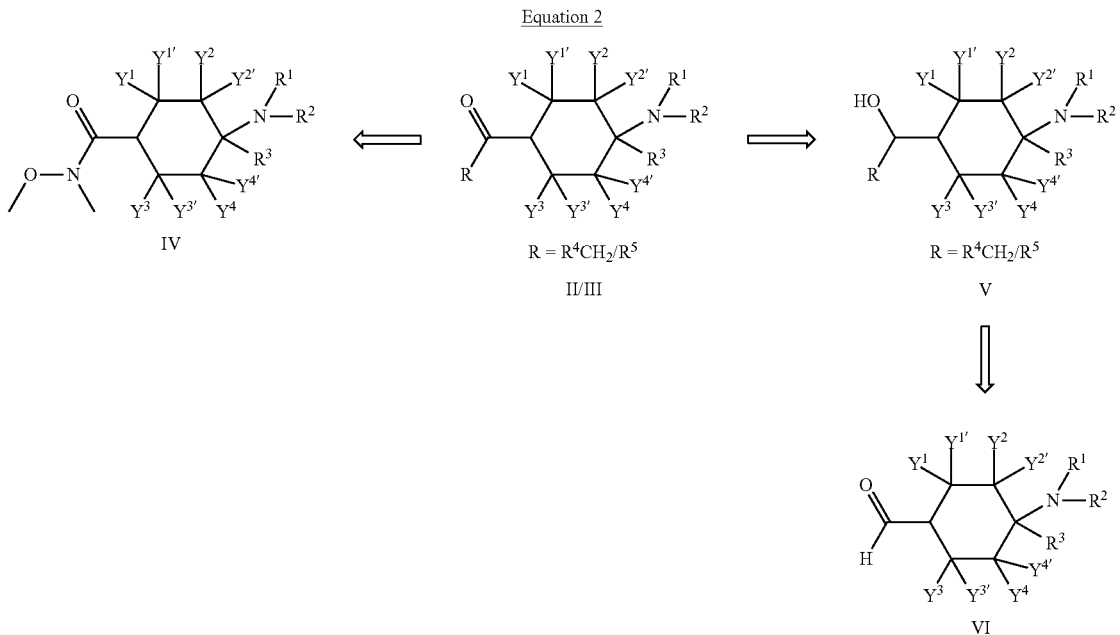

The preparation of Weinreb amides is known to the person skilled in the art.

In the case where $R^5$ is identical to $R^4$—$CH_2$—, compounds of the general formula I can also be obtained by addition of at least 2 equivalents of a suitable carbon nucleophile on to corresponding carboxylic acids esters or other suitable carbonyl compounds.

In the case where $R^5$ is —H, intermediate stages V and VI are eliminated.

An alternative process for the preparation of compounds of the general formula I comprises ring-opening substitution by means of suitable nucleophiles containing $R^4$ on terminal epoxides VII (equation 3). In this context, acetal-protected precursors VIII, preferably ketals, can advantageously be used as starting substances. The ketal VIII resulting from ring-opening substitution is deprotected to give IX. In a further step, a suitable protective group is introduced on to the alcohol function, e.g. another acetal, resulting in compounds of the general formula X. The keto functions obtained beforehand are converted into aminonitriles XI by processes known to the person skilled in the art, which are then converted into amines of the type XII with carbon nucleophiles by familiar methods. The compounds of the general formula I are then obtained by removal of the acetal protective group on the alcohol.

This process is particularly advantageous in the case where $R^4$ is bonded via a hetero atom, i.e. $R^4$ starts with a hetero atom chosen from N, S and O.

Terminal epoxides of the type VII can be prepared by processes known to the person skilled in the art. e.g. by addition of methylides on to suitable carbonyl compounds III or e.g. by epoxidation of corresponding olefins XIV (equation 4):

Equation 4

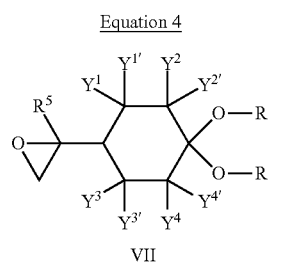

Equaztion 3

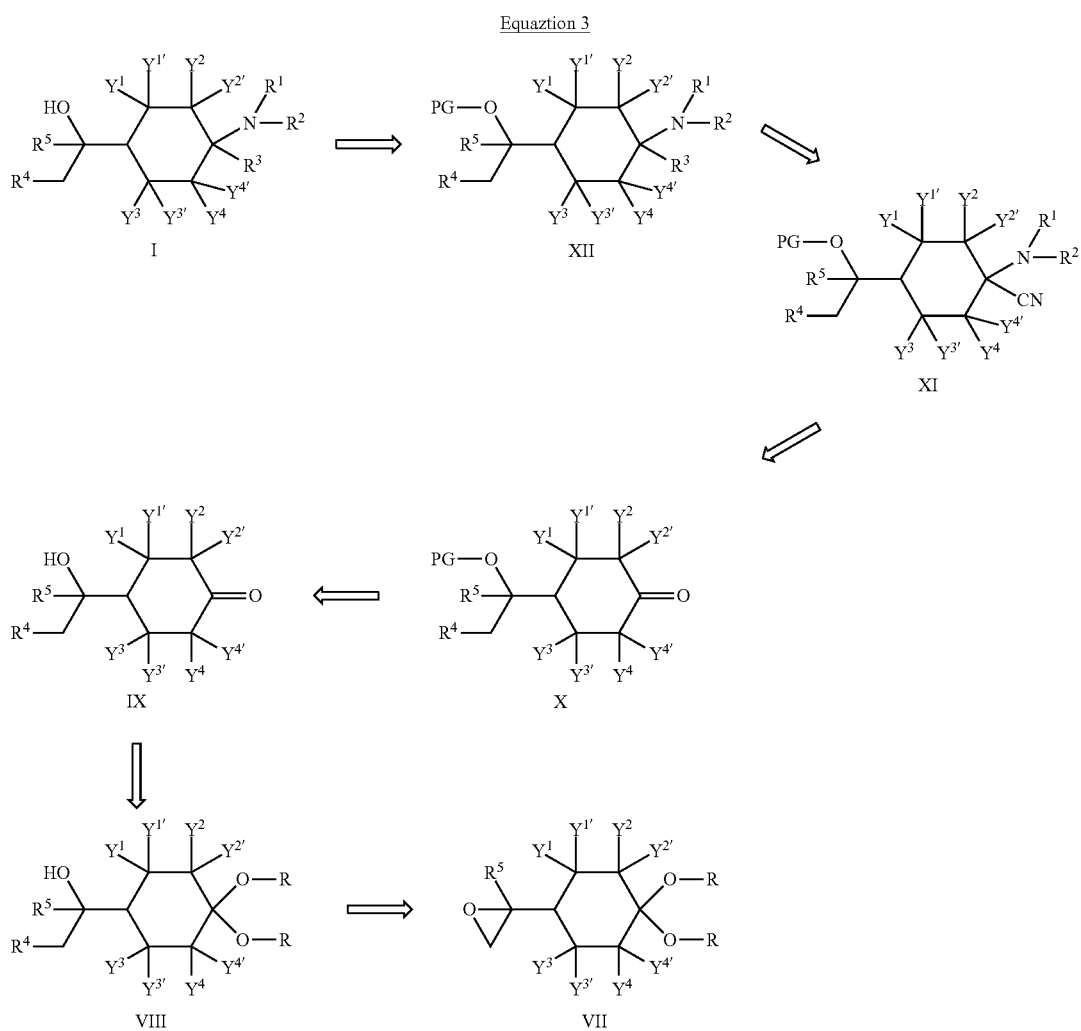

-continued

XIV → III

With respect to further details of the synthesis of the compounds according to the invention, reference may be made in full scope to WO2002/090317, WO2002/90330, WO2003/008370, WO2003/008731, WO2003/080557, WO2004/043899, WO2004/043900, WO2004/043902, WO2004/043909, WO2004/043949, WO2004/043967, WO2005/063769, WO2005/066183, WO2005/110970, WO2005/110971, WO2005/110973, WO2005/110974, WO2005/110975, WO2005/110976, WO2005/110977, WO2006/018184, WO2006/108565, WO2007/079927, WO2007/079928, WO2007/079930, WO2007/079931, WO2007/124903, WO2008/009415 and WO2008/009416.

EXAMPLES

The following examples serve to illustrate the invention in more detail, but are not to be interpreted as limiting.

The yields of the compounds prepared are not optimized. All the temperatures are uncorrected. The term "ether" means diethyl ether, "EA" ethyl acetate and "MC" methylene chloride. The term "equivalent" means equivalent substance amount, "m.p." melting point or melting range, "decomp." decomposition, "RT" room temperature, "abs." absolute (anhydrous), "rac." racemic, "conc." concentrated, "min" minutes, "h" hours, "d" days, "vol. %" percent by volume, "wt. %" percent by weight, and "M" is a concentration stated in mol/l.

Silica gel 60 (0.040-0.063 mm) from E. Merck, Darmstadt was employed as the stationary phase for the column chromatography. The thin layer chromatography investigations were carried out with HPTLC precoated plates, silica gel 60 F 254 from E. Merck, Darmstadt. The mixing ratios of mobile phases for chromatography investigations are always stated in volume/volume.

$^1$H-NMR: Varian Mercury 400BB, 400 MHz or Varian Mercury 300 BB, 300 MHz;

$^{13}$C-NMR: Varian Mercury 400BB, 100 MHz or Varian Mercury 300 BB, 75 MHz;

internal standard: TMS, chemical shifts in ppm; br: broad signal $^{19}$F-NMR: Varian Mercury 400BB, 376.8 MHz internal standard: CFCl$_3$ LC-MS: Agilent LC-MS 1200 Rapid Resolution with MSD6140

Gradient: Time 0 min: 95% water (+1% formic acid)/5% methanol (+1% formic acid)→time 5.4 min: 0% water/100% methanol+1% formic acid)

Column temperature: 50° C.; injection volume: 5 µl; flow rate 0.8 ml/min; fragmenter voltage: 100 V [pos/neg]; detection: MM-ES+APCI+DAD (254 nm); column: SB-C18, 2.1 mm×30 mm, 3.5 micron.

| Method No. | Duration [min] | Flow rate [ml/min] |
|---|---|---|
| 1 | 7 | 0.8 |
| 7 | 7.5 | 0.8 |
| 8 | 7 | 0.8 |

Continuation of method table LC/MS

| Method no. | Gradient | Column temp. [° C.] | Wavelength [nm] | UV scan | Mass range | Pos/neg | Fragmenting [V] |
|---|---|---|---|---|---|---|---|
| 1 | 5-100 | 30 | 254 | * | 100-800 | */* | 50 |
| 7 | 5-100 | 50 | 254 | * | 100-600 | */* | 100 |
| 8 | 5-100 | 80 | 254 | * | 80-800 | */* | 100 |

Example 1

1-(4-Dimethylamino-4-(3-fluoro-phenyl)cyclohexyl)-2-phenyl-ethanol

Stage 1

4-Dimethylamino-4-(3-fluorophenyl)cyclohexanecarbaldehyde

A 60% dispersion of sodium hydride in mineral oil (254 mg, 6.36 mmol) was added to a suspension of methoxymethyltriphenylphosphonium chloride (2.18 g, 6.36 mmol) in anhydrous tetrahydrofuran (5 ml) and anhydrous N,N-dimethylformamide (5 ml) under argon. The mixture was stirred at room temperature for 2 h. A solution of 4-dimethylamino-4-(3-fluorophenyl)cyclohexanone (1.0 g, 4.24 mmol) in anhydrous tetrahydrofuran (5 ml) and anhydrous N,N-dimethylformamide (5 ml) was then added dropwise in the course of 30 min and the mixture was stirred at room temperature overnight. 2 M hydrochloric acid (25 ml) was then added dropwise, while cooling with ice, and the mixture was stirred at room temperature for 5 h. Thereafter, the mixture was extracted with ethyl acetate (5×20 ml) and diethyl ether (3×20 ml). The aqueous phase was adjusted to pH 11 with 4 M sodium hydroxide solution and extracted with ethyl acetate (4×20 ml). The combined organic extracts from the alkaline solution were dried with sodium sulfate and concentrated i. vac.

Yield: 1.49 g (>100%), brown oil $^1$H-NMR (DMSO-d$_6$): The product is a diastereoisomer mixture. All the characteristic signals could be identified.

Stage 2

1-(4-Dimethylamino-4-(3-fluoro-phenyl)cyclohexyl)-2-phenyl-ethanol

A 2 M solution of benzylmagnesium chloride in tetrahydrofuran (6.00 ml, 12 mmol) was added dropwise to a solution of 4-dimethylamino-4-(3-fluorophenyl)cyclohexanecarbaldehyde (1.49 g, 5.97 mmol) in anhydrous tetrahydrofuran (30 ml), while cooling with ice. The mixture was stirred at room temperature for 2 d and saturated ammonium chloride solution (30 ml) was then added, while cooling with ice. The tetrahydrofuran was removed i. vac. and the residue was brought to pH 8 with 4 M sodium hydroxide solution. The aqueous suspension was extracted with diethyl ether (3×30 ml). The combined organic phases were dried with sodium sulfate and concentrated i. vac. The crude product (2.18 g) was purified by flash chromatography with methylene chloride/methanol [95:5+1% $NH_3$ (32% in $H_2O$)]. The impure polar diastereoisomer (500 mg) was purified again by flash chromatography with methylene chloride/methanol [95:5+1% $NH_3$ (32% in $H_2O$)].

Yield: 125 mg (6%), white solid

Melting point: 170° C.

$^1$H-NMR (DMSO-$d_6$): 0.56-1.10 (m, 2H); 1.20-1.60 (m, 4H); 1.74 (br d, 1H, J=13.0 Hz); 1.91 (s, 6H); 2.46 (m, 1H, overlapped by the DMSO signal); 2.56-2.70 (m, 3H); 3.27 (m, 1H); 4.23 (d, 1H, J=6.0 Hz); 7.02-7.25 (m, 8H); 7.41 (dd, 1H, J=7.9 and 14.5 Hz).

$^{13}$C-NMR (DMSO-$d_6$): 23.2; 25.8; 32.4; 32.7; 37.9; 40.7; 42.8; 61.0; 74.5; 112.8 (d, J=21 Hz); 114.6 (d, J=21 Hz); 123.9; 125.3; 127.8; 129.2; 140.2; 162.2 (d, J=242 Hz).

Example 2

1-(4-Butyl-4-dimethylaminocyclohexyl)-2-phenylethanol

By replacing 4-dimethylamino-4-(3-fluorophenyl)cyclohexanone by 4-butyl-4-dimethylaminocyclohexanone in Example 1, stage 1 and subsequent analogous reaction in stage 2, Example 2 was obtained:

$^1$H-NMR (CDCl$_3$): 0.90 (3H, t, J=7.1 Hz); 1.14-1.49 (9H, m); 1.56-1.82 (6H, m); 2.28 (6H, s); 2.63 (1H, dd, J=8.9, 13.6 Hz); 2.88 (1H, dd, J=4.7, 13.6 Hz); 3.66 (1H, m); 7.16-7.22 (3H, m); 7.27-7.29 (2H, m). The OH proton could not be identified.

$^{13}$C-NMR (CDCl$_3$): 14.0; 21.8; 23.5; 23.7 (2C); 26.7 (2C); 31.1; 31.7; 31.8; 37.0 (2C); 41.0; 42.3; 76.4; 126.0; 128.3 (2C); 129.3 (2C); 139.3.

LC-MS (method 8): [M+H]$^+$: m/z=304.3, $R_t$=2.4 min.

Example 3 and Example 4

(1-(4-Dimethylamino-4-phenylcyclohexyl)-2-phenylethanol hydrochloride, Less Polar Diastereomer)

(1-(4-Dimethylamino-4-phenylcyclohexyl)-2-phenylethanol, More Polar Diastereomer)

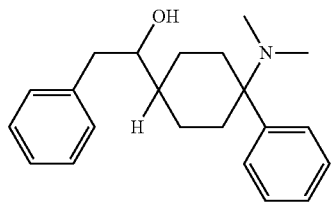

By replacing 4-dimethylamino-4-(3-fluorophenyl)cyclohexanecarbaldehyde by 4-dimethylamino-4-phenylcyclohexanecarbaldehyde in Example 1, stage 2, Examples 3 and 4 were obtained analogously:

1-(4-Dimethylamino-4-phenylcyclohexyl)-2-phenylethanol (Nonpolar Diastereoisomer)

Yield: 170 mg (16%), yellowish oil.

$^1$H-NMR (CDCl$_3$): 1.35-1.90 (m, 6H); 2.05 (s, 6H); 2.58-2.72 (m, 3H); 2.94-3.06 (m, 1H); 3.42-3.50 (m, 1H); 3.72 (br s, 1H); 4.20-4.23 (m, 1H); 7.02-7.95 (m, 10H).

1-(4-Dimethylamino-4-phenylcyclohexyl)-2-phenylethanol (Polar Diastereoisomer)

Yield: 142 mg (14%), white solid

Melting point: 161-166° C.

$^1$H-NMR (CDCl$_3$): 0.99-1.16 (m, 2H); 1.46-1.78 (m, 5H); 1.89-1.98 (m, 1H); 2.07 (s, 6H); 2.49 (dd, 1H, J=9.5 and 13.5 Hz); 2.76 (br d, 1H, J=12.5 Hz); 2.80 (dd, 1H, J=13.7, 3.2 Hz); 3.40 (ddd, 1H, J=9.6, 6.4, 3.3 Hz); 7.11-7.43 (m, 10H).

Stage 2

(1-(4-Dimethylamino-4-phenylcyclohexyl)-2-phenylethanol hydrochloride, Less Polar Diastereomer)

A 7.5 M solution of hydrogen chloride in diethyl ether (25 ml) was added to 1-(4-dimethylamino-4-phenylcyclohexyl)-2-phenylethanol (nonpolar Diastereoisomer, 140 mg, 0.41 mmol). The supernatant solution was decanted and the precipitate was dried over potassium hydroxide i. vac. in a desiccator.

Yield: 80 mg (51%), white solid

Melting point: 235° C.

$^1$H-NMR (DMSO-$d_6$): 1.29-1.44 (m, 3H); 1.76-1.90 (m, 1H); 1.92-2.04 (m, 1H); 2.24-2.38 (m, 2H); 2.43 (t, 6H, J=5.3 Hz); 2.45-2.58 (m, 3H, partly overlapped by the DMSO signal); 2.90 (dd, 1H, J=3.1 and 13.7 Hz); 3.80-3.88 (m, 1H); 4.44 (s, 1H); 7.13-7.19 (m, 1H); 7.22-7.29 (m, 4H); 7.47-7.55 (m, 3H); 7.66-7.71 (m, 2H); 10.48 (s, 1H).

Example 5

1-(4-Dimethylamino-4-phenylcyclohexyl)-2-(4-fluorophenyl)ethanol

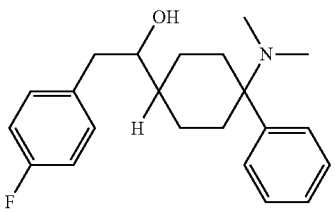

By replacing benzylmagnesium chloride by 4-fluorobenzylmagnesium chloride in Example 3 and 4, stage 1, Example 5 was obtained analogously:

Melting point: 75° C.

$^1$H-NMR (CDCl$_3$): 1.32-1.56 (m, 3H); 1.58-1.84 (m, 6H); 2.05 (s, 6H); 2.66 (m, 2H); 2.95 (d, 1H, J=13.8 Hz); 3.68 (m, 1H); 6.96-7.05 (m, 2H); 7.18-7.40 (m, 7H).

$^{13}$C-NMR (DMSO-$d_6$): 23.1; 24.1; 32.8; 32.9; 37.8; 40.3; 42.5; 58.9; 76.4; 115.2 (d, J=21 Hz); 126.4; 126.6; 127.2; 130.7 (d, J=8 Hz); 134.9; 139.6; 161.6 (d, J=244 Hz).

LC-MS (method 8): [M+H]$^+$: m/z=342.3, $R_t$=2.4 min.

Example 6 and Example 7

1-(4-Dimethylamino-4-thiophen-2-yl-cyclohexyl)-2-phenylethanol (Polar Diastereomer) and 1-(4-dimethylamino-4-thiophen-2-yl-cyclohexyl)-2-phenylethanol (Nonpolar Diastereomer)

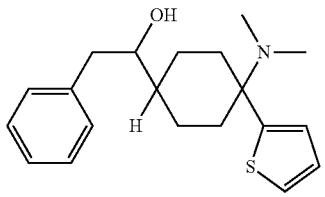

Stage 1

1-(1,4-Dioxaspiro[4.5]dec-8-Yl)-2-phenylethanol

A 2 M solution of benzylmagnesium chloride (26 ml, 52 mmol) was added dropwise to a solution of 1,4-dioxaspiro[4,5]decane-8-carbaldehyde (4.42 g, 25.9 mmol) in anhydrous tetrahydrofuran (30 ml), while cooling with ice. The mixture was stirred at room temperature overnight. Saturated ammonium chloride solution (10 ml) and water (10 ml) were then added to the reaction mixture, while cooling with ice. The solvent was concentrated i. vac. The residue was extracted with diethyl ether (3×10 ml). The combined organic phases were dried with sodium sulfate and concentrated i. vac.

Yield: 2.23 g (32%), white solid
Melting point: 86° C.
$^1$H-NMR (DMSO-$d_6$): 1.15-1.85 (m, 9H); 2.54 (dd, 1H, J=13.6, 8.4 Hz); 2.72 (dd, 1H, J=13.6, 4.2 Hz); 3.45 (m, 1H); 3.83 (s, 4H); 4.38 (d, 1H; J=6.0 Hz); 7.10-7.30 (m, 5H).

In analogous batches with 3 to 48.11 mmol employing from 2 to 4 molar equivalents of benzylmagnesium chloride, yields of from 26 to 47% were achieved.

Stage 2

4-(1-Hydroxy-2-phenylethyl)cyclohexanone

2 M hydrochloric acid (30 ml) was added to a solution of 1-(1,4-dioxaspiro[4.5]dec-8-yl)-2-phenylethanol (2.98 g, 11.3 mmol) in tetrahydrofuran (30 ml). The solution was stirred at 50° C. overnight. The mixture was rendered alkaline with 4 M sodium hydroxide solution, the phases were separated and the aqueous phase was extracted with methylene chloride (3×20 ml). The combined organic phases were dried with sodium sulfate and concentrated i. vac.

Yield: 2.52 g (100%), colourless oil
$^1$H-NMR (DMSO-$d_6$): 1.40-1.80 (m, 3H); 1.90 (m, 1H); 2.08 (m, 1H); 2.14-2.42 (m, 4H); 2.61 (dd, 1H, J=8.2 and 13.6 Hz); 2.76 (dd, 1H, J=4.6 and 13.6 Hz); 3.59 (m, 1H); 4.57 (d, 1H, J=5.9 Hz); 7.13-7.32 (m, 5H).

Stage 3

4-[1-(1-Ethoxy-ethoxy)-2-phenylethyl]cyclohexanone

Ethyl vinyl ether (998 mg, 1.32 ml, 13.8 mmol) and pyridinium tosylate (44 mg, 0.17 mmol) were added to a solution of 4-(1-hydroxy-2-phenylethyl)cyclohexanone (2.52 g, 11.5 mmol) in anhydrous methylene chloride (50 ml) and the mixture was stirred at room temperature overnight. Methylene chloride (20 ml) was added to the mixture and the mixture was washed with water, 5% sodium bicarbonate solution and sodium chloride solution (50 ml of each). The combined organic phases were dried with sodium sulfate and concentrated i. vac.

Yield: 2.93 g, orange-coloured oil.
$^1$H-NMR (DMSO-$d_6$): The spectrum contains all the expected signals.
The product is a mixture of two diastereoisomers.

Stage 4

1-Dimethylamino-4-[1-(1-ethoxy-ethoxy)-2-phenylethyl]cyclohexanecarbonitrile

40% aqueous dimethylamine solution (6.05 ml, 47.9 mmol) was added to a mixture of 4 M hydrochloric acid (2.61 ml) and methanol (1.56 ml), while cooling with ice. A solution of 4-[1-(1-ethoxy-ethoxy)-2-phenylethyl]cyclohexanone (2.91 g, 10.0 mmol) in methanol (6 ml) and tetrahydrofuran (3 ml) was added to this mixture. Thereafter, potassium cyanide (1.56 g, 24.1 mmol) was added to the mixture, the mixture was stirred at room temperature overnight, water (150 ml) was then added and the mixture was extracted with diethyl ether (4×50 ml). The combined organic phases were dried with sodium sulfate and concentrated i. vac. The residue was taken up in methylene chloride (50 ml) and the mixture was washed with water (30 ml). The organic phase was dried again with sodium sulfate and concentrated i. vac.

Yield: 3.18 g, orange-coloured oil.
$^1$H-NMR (DMSO-$d_6$): The spectrum contains all the expected signals. The product is a mixture of diastereoisomers.

Stage 5

{4-[1-(1-Ethoxy-ethoxy)-2-phenylethyl]-1-thiophen-2-yl-cyclohexyl}dimethylamine

A 1 M solution of 2-thienylmagnesium bromide in tetrahydrofuran (9.25 ml, 9.25 mmol) was added dropwise to a solution of 1-dimethylamino-4-[1-(1-ethoxy-ethoxy)-2-phenylethyl]cyclohexanecarbonitrile (1.06 g, 3.1 mmol) in tetrahydrofuran (15 ml), while cooling with ice and under an argon atmosphere. The mixture was stirred at room temperature for 48 h and water and saturated ammonium chloride solution (10 ml of each) were then added. The phases were separated and the aqueous phase was extracted with diethyl ether (3×10 ml). The combined organic phases were dried with sodium sulfate and concentrated i. vac.

Yield: 1.12 g, yellowish oil.
$^1$H-NMR (DMSO-$d_6$): The spectrum contains all the expected signals. The product is a mixture of diastereoisomers.

Stage 6

1-(4-Dimethylamino-4-thiophen-2-yl-cyclohexyl)-2-phenylethanol

2 M hydrochloric acid (20 ml) was added to a solution of {4-[1-(1-ethoxy-ethoxy)-2-phenylethyl]-1-thiophen-2-yl-cyclohexyl}dimethylamine (1.10 g, 2.73 mmol) in tetrahydrofuran (20 ml) and the reaction mixture was stirred at room temperature overnight. It was then rendered alkaline with 4 M sodium hydroxide solution and extracted with methylene chloride (4×10 ml). The combined organic phases were dried with sodium sulfate and concentrated i. vac. The crude product (956 mg) was purified by flash chromatography with cyclohexane/ethyl acetate (3:2) and then methanol. The two product fractions obtained in this way were each taken up in diethyl ether, and 2 M hydrochloric acid (20 ml) was added. The phases were separated. The acid aqueous phases were extracted with diethyl ether (3×10 ml) and thereafter rendered alkaline with 4 M sodium hydroxide solution. The aqueous phases were extracted with methylene chloride (4×10 ml). The combined organic phases were dried with sodium sulfate and concentrated i. vac.

Polar Diastereoisomer

Yield: 466 mg (46%, based on the stage 2 employed), beige-coloured solid

Melting point: 85° C.

$^1$H-NMR (DMSO-$d_6$): 1.22-1.75 (m, 7H); 2.01 (s, 6H); 2.40-2.46 (m, 2H); 2.55 (dd, 1H, J=13.6 and 8.6 Hz); 2.75 (dd, 1H, J=13.6 and 4.0 Hz); 3.45 (m, 1H); 4.35 (d, 1H, J=6.1 Hz); 6.90 (d, 1H, J=3.5 Hz); 7.03 (dd, 1H, J=3.5 and 5.1 Hz); 7.14-7.30 (m, 5H); 7.37 (d, 1H, J=5.1 Hz).

$^{13}$C-NMR (DMSO-$d_6$): 22.1; 23.9; 35.1; 35.3; 37.5; 40.6; 42.8; 58.1; 75.1; 122.8; 123.5; 125.3; 126.0; 127.7; 129.3; 140.4; 145.2.

LC-MS (method 7): [M+H]$^+$: m/z=330.3, $R_t$=2.8 min.

Nonpolar Diastereoisomer

Yield: 16 mg (1%, based on the stage 2 employed), yellow oil $^1$H-NMR (CDCl$_3$): 1.43-1.82 (m, 8H); 2.12 (s, 6H); 2.51 (d, 2H, J=13.8 Hz); 2.63 (dd, 1H, J=9.5 and 13.6 Hz); 2.97 (dd, 1H, J=3.4 and 13.6 Hz); 3.70 (m, 1H); 6.87 (dd, 1H, J=1.1 and 3.4 Hz); 7.03 (dd, 1H, J=3.6 and 5.1 Hz); 7.20-7.27 (m, 4H); 7.30-7.36 (m, 2H).

LC-MS (method 1): [M+H]$^+$: m/z=330.3, $R_t$=3.3 min.

Example 8

1-(4-Butyl-4-dimethylaminocyclohexyl)-2-phenylethanol

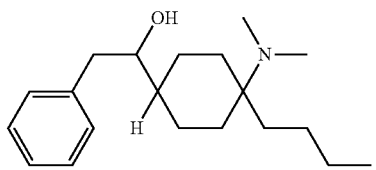

In an analogous procedure to Example 6 and 7 using stage 4 and replacing thienylmagnesium bromide by butylmagnesium bromide in stage 5, Example 8 was obtained.

Stage 5

{1-Butyl-4-[1-(1-ethoxy-ethoxy)-2-phenylethyl]cyclohexyl}dimethylamine

A 2 M solution of n-butylmagnesium chloride in tetrahydrofuran (4.62 ml, 9.25 mmol) was added dropwise to a solution of 1-dimethylamino-4-[1-(1-ethoxy-ethoxy)-2-phenylethyl]cyclohexanecarbonitrile (1.06 g, 3.1 mmol) in tetrahydrofuran (15 ml), while cooling with ice and under an argon atmosphere. The mixture was stirred at room temperature for 48 h and thereafter water and saturated ammonium chloride solution (10 ml of each) were added. The phases were separated and the aqueous phase was extracted with diethyl ether (3×10 ml). The combined organic phases were dried with sodium sulfate and concentrated i. vac.

Yield: 1.12 g, yellowish oil.

$^1$H-NMR (DMSO-$d_6$): The spectrum contains all the expected signals.

The product is a mixture of diastereoisomers.

Stage 6

1-(4-Butyl-4-dimethylaminocyclohexyl)-2-phenylethanol

2 M hydrochloric acid (20 ml) was added to a solution of {1-butyl-4-[1-(1-ethoxy-ethoxy)-2-phenylethyl]cyclohexyl}dimethylamine (1.09 g, 2.90 mmol) in anhydrous tetrahydrofuran (20 ml) and the mixture was stirred at room temperature for 3 d. The tetrahydrofuran was removed i. vac. and the acid aqueous solution was extracted with diethyl ether (3×10 ml) and thereafter rendered alkaline with 4 M sodium hydroxide solution. The alkaline phase was extracted with methylene chloride (4×10 ml). The combined organic phases were dried with sodium sulfate and concentrated i. vac. The crude product (646 mg) was purified by flash chromatography with methylene chloride/methanol (9:1→8:2→0:1). The product obtained in this way was in the form of the hydrochloride. It was taken up in methylene chloride and the suspension was washed with saturated potassium carbonate solution. The organic phase was dried with sodium sulfate and concentrated i. vac.

Yield: 306 mg (35%, based on the stage 2 employed), yellowish oil $^1$H-NMR (DMSO-$d_6$): 0.86 (t, 3H, J=7.0 Hz); 1.45-1.58 (m, 13H); 1.66-1.75 (m, 2H); 2.13 (s, 6H); 2.52 (dd, 1H, J=8.5 and 13.3 Hz, partly overlapped by the DMSO signal); 2.72 (dd, 1H, J=4.1 and 13.6 Hz); 3.38 (m, 1H); 4.26 (d, 1H, J=6.0 Hz); 7.10-7.30 (m, 5H).

$^{13}$C-NMR (DMSO-$d_6$): 13.9; 21.6; 23.4; 23.5; 26.4; 30.8; 32.0; 32.1; 36.8; 40.6; 43.0; 55.5; 75.3; 125.4; 127.8; 129.1; 140.3.

LC-MS (method 7): [M+H]$^+$: m/z=304.5, $R_t$=2.9 min.

Example 9

1-[4-Dimethylamino-4-(3-methoxyphenyl)cyclohexyl]-2-phenylethanol

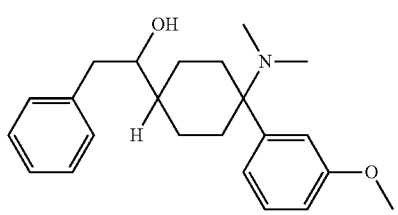

In an analogous procedure to Example 6 and 7 using stage 4 and replacing thienylmagnesium bromide by 3-methoxyphenylmagnesium bromide in stage 5, Example 9 was obtained.

Stage 5

[4-[1-(1-Ethoxy-ethoxy)-2-phenylethyl]-1-(3-methoxyphenyl)cyclohexyl]dimethylamine A 1 M solution of 3-methoxyphenylmagnesium bromide in tetrahydrofuran (9.25 ml, 9.25 mmol) was added dropwise to a solution of 1-dimethylamino-4-[1-(1-ethoxy-ethoxy)-2-phenylethyl]cyclohexanecarbonitrile (1.06 g, 3.1 mmol) in tetrahydrofuran (15 ml), while cooling with ice and under an argon atmosphere. The mixture was stirred at room temperature for 48 h and thereafter water and saturated ammonium chloride solution (10 ml of each) were added. The phases were separated and the aqueous phase was extracted with diethyl ether (3×10 ml). The combined organic phases were dried with sodium sulfate and concentrated i. vac.

Yield: 1.56 g, yellowish oil.
$^1$H-NMR (DMSO-$d_6$): The spectrum contains all the expected signals.
The product is a mixture of diastereoisomers.

Stage 6

1-[4-Dimethylamino-4-(3-methoxyphenyl)cyclohexyl]-2-phenylethanol

2 M hydrochloric acid (20 ml) was added to a solution of WW561 (1.54 g, 3.61 mmol) in anhydrous tetrahydrofuran (20 ml) and the mixture was stirred at room temperature for 2 d. The tetrahydrofuran was removed i. vac. and the acid aqueous solution was extracted with diethyl ether (3×10 ml) and thereafter rendered alkaline with 4 M sodium hydroxide solution. The alkaline aqueous phase was extracted with methylene chloride (4×10 ml). The combined organic phases were dried with sodium sulfate and concentrated i. vac. The crude product (670 mg) was purified by flash chromatography with cyclohexane/ethyl acetate (3:2)→methylene chloride/methanol (9:1).

Yield: 163 mg (15%, based on stage 3), white solid
Melting point: 75° C.
$^1$H-NMR (DMSO-$d_6$): 1.15-1.52 (m, 7H); 1.95 (s, 6H); 2.52-2.68 (m, 3H); 2.77 (dd, 1H, J=3.7 and 13.6 Hz); 3.45 (m, 1H); 3.74 (s, 3H); 4.33 (d, 1H, J=6.1 Hz); 6.78-6.84 (m, 2H); 6.89 (d, 1H, J=7.9 Hz); 7.11-7.30 (m, 6H).
$^{13}$C-NMR (DMSO-$d_6$): 22.2; 24.2; 32.8; 32.9; 37.6; 40.5; 42.9; 58.2; 75.0; 110.9; 112.9; 118.8; 125.3; 127.7; 127.9; 129.3; 140.5; 141.5; 158.6.

A further fraction with impure product (350 mg) was purified again by flash chromatography with methylene chloride/methanol (95:5), as a result of which a further 90 mg of 1-[4-dimethylamino-4-(3-methoxyphenyl)cyclohexyl]-2-phenylethanol were obtained (8%, based on stage 3), white solid.
Melting point: 72° C.

Example 10

1-[4-Dimethylamino-4-(3-methoxyphenyl)cyclohexyl]-2-phenylethanol

Stage 1

4-Dimethylamino-4-(3-methoxyphenyl)cyclohexanecarbonitrile

A solution of 4-(dimethylamino)-4-(3-methoxyphenyl)cyclohexanone (2.47 g, 10 mmol) and tosylmethyl isocyanide (2.54 g, 13 mmol) in anhydrous 1,2-dimethoxyethane (40 ml) and anhydrous ethanol (2 ml) was cooled to −30° C. A solution of potassium tert-butylate (2.70 g, 24 mmol) in anhydrous tetrahydrofuran (20 ml) was then added dropwise such that the internal temperature did not rise above 5° C. The mixture was stirred at 0° C. for 1 h, at room temperature for 24 h and then under reflux for 5 h. The reaction mixture was cooled to room temperature and filtered. The residue on the filter was washed with 1,2-dimethoxyethane. The filtrate was concentrated i. vac., the residue was taken up in diethyl ether and the solution was washed with water (3×20 ml) and saturated sodium chloride solution (20 ml). The organic phase was dried with sodium sulfate and concentrated i. vac. The crude product (1.76 g) was purified by flash chromatography with ethyl acetate and then ethyl acetate/methanol (9:1→8:2).
Nonpolar Diastereoisomer
Yield: 401 mg (15%), yellowish oil.
$^1$H-NMR (DMSO-$d_6$): 1.60-1.90 (m, 6H); 1.94 (s, 6H); 2.22-2.34 (m, 2H); 2.81 (m, 1H); 3.74 (s, 3H); 6.78-6.90 (m, 3H); 7.27 (t, 1H, J=7.9 Hz).
$^{13}$C-NMR (DMSO-$d_6$): 24.7; 26.3; 30.5; 37.4; 54.9; 58.7; 111.3; 113.2; 119.3; 122.9; 128.4; 139.2; 158.8.
LC-MS (method 8): [M+H]$^+$: m/z=259.3, $R_t$=0.9 min.
Polar Diastereoisomer
Yield: 505 mg (19%), yellowish oil.
$^1$H-NMR (DMSO-$d_6$): 1.33-1.52 (m, 2H); 1.92 (s, 6H); 1.93-2.18 (m, 6H); 2.92 (m, 1H); 3.76 (s, 3H); 6.80-6.94 (m, 3H); 7.30 (t, 1H, J=7.9 Hz).
$^{13}$C-NMR (DMSO-$d_6$): 24.9; 26.4; 30.3; 37.7; 54.8; 59.2; 111.4; 113.6; 119.4; 122.8; 128.4; 138.7; 158.8.
LC-MS (method 8): [M+H]$^+$: m/z=259.2, $R_t$=1.0 min.

Stage 2

1-[4-Dimethylamino-4-(3-methoxyphenyl)cyclohexyl]-2-phenylethanone

A 2 M solution of benzylmagnesium chloride in tetrahydrofuran (1.4 ml, 2.8 mmol) was added to a solution of the polar diastereoisomer (240 mg, 0.9 mmol) in anhydrous tetrahydrofuran (5 ml), while cooling with ice, and the mixture was stirred at room temperature for 3 d. Saturated ammonium chloride solution (8 ml) and water (5 ml) were added to the reaction mixture. The solvent was removed i. vac. and the aqueous suspension was extracted with diethyl ether (3×20 ml). The combined organic phases were dried with sodium sulfate and concentrated i. vac. The crude product was purified by flash chromatography with methylene chloride/methanol (95.5).
Yield: 120 mg (36%), yellowish oil.
$^1$H-NMR (CDCl$_3$): 1.33-1.46 (m, 2H); 1.72 (t, 2H, J=14.5 Hz); 1.87 (d, 2H, J=11.1 Hz); 2.13 (s, 6H); 2.56 (m, 1H); 2.70 (d, 2H, J=12.5 Hz); 3.69 (s, 2H); 3.85 (s, 3H); 6.82-6.94 (m, 4 Hz); 7.16 (d, 1H, J=7.1 Hz); 7.22-7.38 (m, 4H).

Stage 3

1-[4-Dimethylamino-4-(3-methoxyphenyl)cyclohexyl]-2-phenylethanol

Sodium borohydride (24 mg, 0.6 mmol) was added to a solution of the product from stage 2 (112 mg, 0.3 mmol) in anhydrous methanol (5 ml) at 0° C. and the mixture was stirred at room temperature for 3 h. Further sodium borohydride (12 mg, 0.3 mmol) was then added and the mixture was stirred at room temperature for a further 2 h. Water (20 ml) was added to the mixture. The solvent was removed i. vac. and the aqueous suspension was extracted with ethyl acetate (3×10 ml). The combined organic phases were dried with sodium sulfate and concentrated i. vac. The crude product (76 mg) was purified by flash chromatography (10 g, 20×1.1 cm) with methylene chloride/methanol [(95.5)+1% ammonia solution (30% in $H_2O$)].

Yield: 57 mg (50%), yellowish solid

Melting point: 120° C.

$^1$H-NMR (DMSO-$d_6$): 0.84-1.12 (m, 2H); 1.18-1.58 (m, 6H); 1.72 (d, 1H, J=12.5 Hz); 1.91 (s, 6H); 2.40-2.50 (m, 1H); 2.54-2.70 (m, 2H); 3.26 (m, 1H); 3.75 (s, 3H); 4.20 (d, 1H, J=6.0 Hz); 6.79-6.92 (m, 3H); 7.10-7.33 (m, 6H).

$^{13}$C-NMR (DMSO-$d_6$): 23.5; 25.9; 32.5; 32.7; 37.9; 40.7; 42.9; 61.1; 74.6; 110.7; 114.4; 120.3; 125.3; 127.8; 128.4; 129.1; 138.4; 140.1; 158.9.

Example 11

1-(4-(Dimethylamino)-4-(3-fluorophenyl)cyclohexyl)-2-(5-(phenylsulfonyl)-3,4-dihydro-1H-pyrido[4,3-b]indol-2(5H)-yl)ethanol

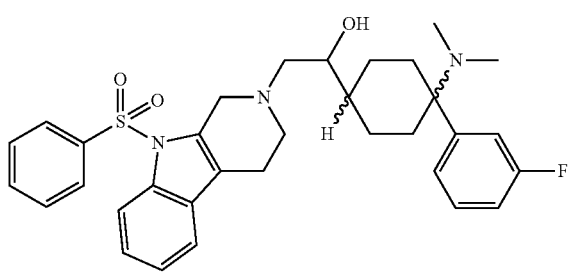

Stage 1

1,3,4,9-Tetrahydro-β-carboline-2-carboxylic acid benzyl ester

A solution of N-(benzyloxycarbonyloxy)succinimide (9.61 g, 38.6 mmol) in anhydrous tetrahydrofuran (30 ml) was added to a suspension of 2,3,4,9-tetrahydro-1H-β-carboline (4.43 g, 25.7 mmol) and 4-N,N-dimethylaminopyridine (266 mg) in anhydrous tetrahydrofuran (30 ml), while cooling with ice. The suspension was stirred at room temperature for 16 h and the tetrahydrofuran was then removed i. vac. The residue was dissolved in ethyl acetate (20 ml) and the solution was washed with water (2×20 ml). The organic phase was dried with sodium sulfate and concentrated i. vac. The crude product (11.0 g) was purified by flash chromatography with cyclohexane/ethyl acetate (4:1).

Yield: 6.64 g (84%), white solid $^1$H-NMR (DMSO-$d_6$): 2.71 (t, 2H, J=5.6 Hz); 3.76 (t, 2H, J=5.3 Hz); 4.64 (br s, 2H); 5.14 (s, 2H); 6.96 (ddd, 1H, J=8.0, 7.1 and 1.1 Hz); 7.04 (ddd, 1H, J=8.2, 7.1 and 1.2 Hz); 7.25-7.44 (m, 7H); 10.78 and 10.84 (2 s, 1H).

Stage 2

9-Benzenesulfonyl-1,3,4,9-tetrahydro-β-carboline-2-carboxylic acid benzyl ester

Powdered sodium hydroxide (1.73 g, 43.3 mmol) and tetra-n-butylammonium hydrogen sulfate (111 mg) were added to a solution of the product from stage 1 (6.61 g, 21.6 mmol) in anhydrous methylene chloride (100 ml) and the mixture was stirred at room temperature for 1 h. Benzenesulfonyl chloride (4.21 g, 3.07 ml, 23.8 mmol) was added to the suspension, while cooling with ice. The mixture was stirred at room temperature for 16 h and water and methylene chloride (50 ml of each) were then added. The organic phase was separated off and washed with sodium chloride solution (40 ml). The organic phase was dried with sodium sulfate and concentrated i. vac. The residue was purified by flash chromatography with cyclohexane/ethyl acetate (4:2).

Yield: 5.66 g (58%), white solid

Melting point: 153° C.

$^1$H-NMR (DMSO-$d_6$): 2.67 (t, 2H, J=5.5 Hz); 3.73 (t, 2H, J=4.7 Hz); 4.97 (br s, 2H); 5.16 (s, 2H); 7.26 (dt, 1H, J=7.4 and 1.0 Hz); 7.31-7.94 (m, 12H); 8.01 (br d, J=8.1 Hz).

Stage 3

9-Benzenesulfonyl-2,3,4,9-tetrahydro-1H-β-carboline

33% hydrogen bromide in glacial acetic acid (20.7 ml) was added to a suspension of the product from stage 2 (4.14 g, 9.27 mmol) in glacial acetic acid (20.7 ml) and the mixture was stirred at room temperature for 1 h. The mixture was poured into diethyl ether (500 ml). The hydrobromide which had precipitated out was filtered off with suction, washed with diethyl ether and dried over potassium hydroxide in a desiccator. Saturated potassium carbonate solution (100 ml) was added to the salt (3.60 g) and the resulting mixture was extracted with methylene chloride (3×25 ml). The combined organic phases were dried with sodium sulfate and concentrated i. vac.

Yield: 2.51 g (86%), white solid

Melting point: 190-195° C.

$^1$H-NMR (DMSO-$d_6$): 2.53 (t, 2H, J=5.5 Hz); 2.91 (t, 2H, J=5.5 Hz); 4.11 (s, 2H); 7.20-7.33 (m, 2H); 7.40-7.43 (m, 1H); 7.52-7.60 (m, 2H); 7.62-7.70 (m, 1H); 7.84-7.90 (m, 2H); 7.96-8.04 (m, 1H).

Stage 4

2-(9-Benzenesulfonyl-1,3,4,9-tetrahydro-β-carbolin-2-yl)-1-(1,4-dioxaspiro[4.5]dec-8-yl)ethanol Calcium trifluoromethanesulfonate (1.22 g, 3.60 mmol) was added to a solution of the product from stage 3 (2.51 g, 8.05 mmol) and 8-oxiranyl-1,4-dioxaspiro[4.5]decane (1.34 g, 7.30 mmol) in anhydrous tetrahydrofuran (50 ml) and the mixture was stirred at room temperature for 48 h. The tetrahydrofuran was removed i. vac. The residue was taken up in methylene chloride (40 ml) and the mixture was washed with 25% potassium carbonate solution (2×25 ml). The organic phase was dried with sodium sulfate and concentrated i. vac. The crude product (4.31 g) was purified by flash chromatography with cyclohexane/ethyl acetate (1:2).

Yield: 2.33 g (64%), white solid

Melting point: 158° C.

¹H-NMR (DMSO-d$_6$): 1.22-1.48 (m, 5H); 1.57 (s, 1H); 1.62-1.78 (m, 3H); 2.48-2.68 (m, 4H); 2.72-2.90 (m, 2H); 3.51 (m, 1H); 3.83 (s, 4H); 3.95 (d, 1H, J=17.0 Hz); 4.03 (d, 1H, J=17.0 Hz); 4.38 (d, 1H, J=4.4 Hz); 7.25 (dt, 1H, J=7.3 and 1.2 Hz); 7.31 (ddd, 1H, J=8.4, 7.3 and 1.5 Hz); 7.40-7.45 (m, 1H); 7.51-7.60 (m, 2H); 7.64-7.71 (m, 1H); 7.82-7.89 (m, 2H); 7.99-8.03 (m, 1H).

Stage 5

4-[2-(9-Benzenesulfonyl-1,3,4,9-tetrahydro-β-carbolin-2-yl)-1-hydroxyethyl]cyclohexanone 2 M hydrochloric acid (30 ml) was added to a solution of the product from stage 4 (748 mg, 1.50 mmol) in tetrahydrofuran (30 ml) and the mixture was stirred at room temperature for 16 h. The mixture was rendered alkaline with 4 M sodium hydroxide solution and extracted with ethyl acetate (3×35 ml). The combined organic phases were dried with sodium sulfate and concentrated i. vac.

Yield: 658 mg (96%), beige-coloured solid
Melting point: 174° C.
¹H-NMR (DMSO-d$_6$): 1.40-1.64 (m, 2H); 1.76-1.98 (m, 2H); 2.02 (m, 1H); 2.15-2.26 (m, 2H); 2.27-2.45 (m, 2H); 2.54-2.70 (m, 4H); 2.77-2.93 (m, 2H); 3.64 (m, 1H); 3.98 (d, 1H, J=17.0 Hz); 4.06 (d, 1H, J=17.0 Hz); 4.56 (d, 1H, J=4.4 Hz); 7.25 (dt, 1H, J=7.3 and 1.1 Hz); 7.32 (ddd, 1H, J=8.6, 7.3 and 1.4 Hz); 7.44 (m, 1H); 7.52-7.60 (m, 2H); 7.67 (m, 1H); 7.83-7.89 (m, 2H); 8.02 (br d, 1H, J=7.8 Hz).
LC-MS (method 7): [M+H]⁺: m/z=453.2, R$_t$=2.7 min.

Stage 6

4-[2-(9-Benzenesulfonyl-1,3,4,9-tetrahydro-β-carbolin-2-yl)-1-(tert-butyldimethylsilanyloxy)ethyl]cyclohexanone A solution of the product from stage 6 (553 mg, 1.22 mmol), imidazole (250 mg, 3.66 mmol) and tert-butyldimethylchlorosilane (275 mg, 1.83 mmol) in anhydrous N,N-dimethylformamide (20 ml) was stirred at room temperature for 48 h. The reaction mixture was concentrated i. vac. 25% potassium carbonate solution (30 ml) was added to the residue and the mixture was extracted with methylene chloride (3×35 ml). The combined organic phases were dried with sodium sulfate and concentrated i. vac. The crude product (1.3 g) was purified by flash chromatography (85 g, 20×3.8 cm) with cyclohexane/ethyl acetate (2:1).

Yield: 588 mg (85%), white solid
Melting point: 150-152° C.
¹H-NMR (DMSO-d$_6$): 0.03 (s, 3H); 0.04 (s, 3H); 0.85 (s, 9H); 1.44-1.66 (m, 2H); 1.86-2.06 (m, 3H); 2.14-2.25 (m, 2H); 2.28-2.47 (m, 2H); 2.55-2.70 (m, 4H); 2.71-2.92 (m, 2H); 3.83 (m, 1H); 3.89 (d, 1H, J=16.8 Hz); 4.00 (d, 1H, J=16.8 Hz); 7.26 (dt, 1H, J=7.3 and 1.2 Hz); 7.32 (ddd, 1H, 8.6, 7.3 and 1.4 Hz); 7.42-7.48 (m, 1H); 7.52-7.60 (m, 2H); 7.64-7.72 (m, 1H); 7.80-7.88 (m, 2H); 8.00-8.06 (m, 1H).

Stage 7

4-[2-(9-Benzenesulfonyl-1,3,4,9-tetrahydro-β-carbolin-2-yl)-1-(tert-butyldimethylsilanyloxy)ethyl]-1-dimethylamino-cyclohexanecarbonitrile 40% aqueous dimethylamine solution (596 μl, 4.73 mmol) was added to a mixture of 4 M hydrochloric acid (256 μl) and methanol (153 μl), while cooling with ice. A solution of the product from stage 6 (557 mg, 0.98 mmol) in methanol (3 ml) and tetrahydrofuran (3 ml) was added to the mixture. Potassium cyanide (153 mg, 2.36 mmol) and water (2 ml) were then added. The suspension was stirred at room temperature overnight and thereafter diluted with water (20 ml). The mixture was extracted with diethyl ether (5×20 ml). The combined organic phases were dried with sodium sulfate and concentrated i. vac.

Yield: 609 mg (100%), yellowish oil.
The product is a diastereoisomer mixture.
¹H-NMR (DMSO-d$_6$): The spectrum contains all the expected signals.

Stage 8

[4-[2-(9-Benzenesulfonyl-1,3,4,9-tetrahydro-β-carbolin-2-yl)-1-(tert-butyldimethylsilanyloxy)ethyl]-1-(3-fluorophenyl)cyclohexyl]dimethylamine A 1 M solution of 3-fluorophenylmagnesium bromide in tetrahydrofuran (2.5 ml, 2.5 mmol) was added to a solution of the product from stage 7 (521 mg, 0.84 mmol) in anhydrous tetrahydrofuran (20 ml), while cooling with ice and under argon, and the mixture was stirred at room temperature for 2 d. Saturated ammonium chloride solution and water (10 ml of each) were then added to the reaction mixture and the phases were separated. The aqueous phase was extracted with diethyl ether (2×30 ml). The combined organic phases were dried with sodium sulfate and concentrated i. vac. The residue (491 mg) was purified by flash chromatography with cyclohexane/ethyl acetate (4:1), as a result of which the product (211 mg) still contaminated with 3-fluorophenol was obtained. This was purified again by flash chromatography with cyclohexane/tert-butyl methyl ether (4:1).

Yield: 149 mg (25%), white solid
¹H-NMR (DMSO-d$_6$): 0.01 (s, 3H); 0.04 (s, 3H); 0.88 (s, 9H); 1.15-1.80 (m, 7H); 1.92 (s, 6H); 2.56-2.56 (m, 6H); 2.56-2.95 (m, 2H); 3.65-3.73 (m, 1H); 3.86 (d, 1H, J=16.9 Hz); 3.99 (d, 1H, J=17.0 Hz); 7.00-7.15 (m, 2H); 7.20-7.45 (m, 5H); 7.50-7.59 (m, 2H); 7.62-7.70 (m, 1H); 7.80-7.87 (m, 2H); 8.01 (d, 1H, J=8.2 Hz).
¹³C-NMR (DMSO-d$_6$): −5.1; −4.9; −4.0; −3.8; 17.9; 20.5; 24.1; 25.8; 25.9; 32.6; 32.7; 37.4; 49.7; 51.6; 58.3; 61.3; 71.3; 74.1; 111.6 (d, J=22 Hz); 112.6 (d, J=21 Hz); 113.1; 113.7; 117.1; 118.6; 120.7 (br); 122.4; 122.5; 123.6; 124.4; 126.0; 128.8 (d, J=8 Hz); 129.3; 129.8; 132.9; 134.5; 135.3; 137.4; 143.1 (d, J=6 Hz); 161.9 (d, J=242 Hz).
LC/MS (method 8): [M+H]⁺: m/z=691.4, R$_t$=4.2 min.

Stage 9

2-(9-Benzenesulfonyl-1,3,4,9-tetrahydro-β-carbolin-2-yl)-1-[4-dimethylamino-4-(3-fluorophenyl)cyclohexyl]ethanol 2 M hydrochloric acid (20 ml) was added to a solution of the product from stage 8 (176 mg, 0.255 mmol) in tetrahydrofuran (20 ml) and the mixture was stirred at room temperature for 1 d. The reaction mixture was then stirred at 50° C. for 15 h and then at room temperature for a further 16 h. The mixture was then rendered alkaline with 2 M sodium hydroxide solution (30 ml) and the phases were separated. The aqueous phase was extracted with diethyl ether (3×10 ml). The combined organic phases were dried with sodium sulfate and concentrated i. vac. The crude product 151 mg) was purified by flash chromatography with methylene chloride/methanol (97:3).

Yield: 35 mg (22%), colourless oil $^1$H-NMR (CDCl$_3$): 1.35-1.78 (m, 7H); 1.85 (br d, 1H, J=12.4 Hz); 2.04 (s, 6H); 2.48-2.66 (m, 3H); 2.50-2.86 (m, 4H); 3.05 (m, 1H); 3.65 (t, 1H, J=7.8 Hz); 4.02 (d, 1H, J=16.4 Hz); 4.13 (d, 1H, J=16.4 Hz); 6.95 (t, 1H, J=8.1 Hz); 7.01 (dd, 1H, J=11.5 and 1.4 Hz); 7.09 (d, 1H, J=7.5 Hz); 7.20-7.46 (m, 6H); 7.52 (m, 1H); 7.77 (m, 2H); 8.12 (d, 1H, J=8.1 Hz).

$^{13}$C-NMR (CDCl$_3$): 20.8; 23.2; 23.8; 32.9; 37.6; 41.9; 49.5; 51.3; 58.7; 60.3; 70.1; 113.1 (d, J=20 Hz); 113.6 (d, J=21 Hz); 114.2; 117.3; 118.2; 122.4; 123.6; 124.3; 126.2; 128.5 (d, J=8 Hz); 129.3; 129.6; 132.6; 133.6; 136.1; 138.7; 143.0 (br); 162 (d, J=245 Hz).

LC-MS (method 7): [M+H]$^+$: m/z=576.3, R$_f$=2.4 min.

Example 12

2-(1,3-Dihydroisoindol-2-yl)-1-(4-dimethylamino-4-phenylcyclohexyl)ethanol

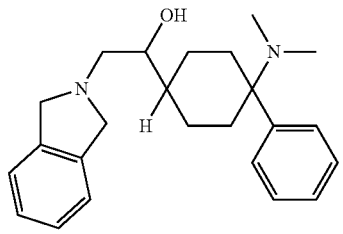

Stage 1

2-(1,3-Dihydroisoindol-2-yl)-1-(1,4-dioxaspiro[4.5]dec-8-yl)ethanol

A solution of 8-oxiranyl-1,4-dioxaspiro[4.5]decane (1.41 g, 7.66 mmol), isoindoline (1.00 g, 8.43 mmol) and calcium trifluoromethanesulfonate (1.29 g, 3.8 mmol) in anhydrous acetonitrile (60 ml) was stirred at room temperature overnight. The solvent was then concentrated in vacuo. The residue was taken up in ethyl acetate (50 ml) and the solution was washed with 25% potassium carbonate solution (3×50 ml). The aqueous phase was extracted with ethyl acetate (3×40 ml) and the combined organic phases were dried with sodium sulfate and concentrated in vacuo.

Yield: 2.04 g (88%), beige-coloured solid $^1$H-NMR (DMSO-d$_6$): 1.24-1.48 (m, 5H); 1.59 (br s, 1H); 1.64-1.74 (m, 3H); 2.56 (dd, 1H, J=7.4, 12.2 Hz); 2.70 (dd, 1H, J=4.7, 12.2 Hz); (m, 2H); 3.44 (m, 1H); 3.83 (s, 4H); 3.83-3.94 (m, 4H); 4.30 (d, 1H, J=4.4 Hz); 7.15-7.26 (m, 4H).

Stage 2

4-[2-(1,3-Dihydroisoindol-2-yl)-1-hydroxyethyl]cyclohexanone

2 M hydrochloric acid (19 ml) was added to a solution of 2-(1,3-dihydroisoindol-2-O-1-(1,4-dioxaspiro[4.5]dec-8-yl)ethanol (2.05 g, 6.74 mmol) in acetone (60 ml) and the mixture was stirred at room temperature overnight. The reaction mixture was concentrated in vacuo, the residue was rendered alkaline with 2 M sodium hydroxide solution and the solution was extracted with methylene chloride (3×40 ml). The combined organic phases were dried with sodium sulfate and concentrated in vacuo. The crude product (1.67 g) was purified by flash chromatography with ethyl acetate/methanol (9:1).

Yield: 1.12 g (64%), beige-coloured solid

Melting point: 136° C.

$^1$H-NMR (DMSO-d$_6$): 1.40-1.68 (m, 2H); 1.82-2.10 (m, 3H); 2.14-2.24 (m, 2H); 2.28-2.46 (m, 2H); 2.70 (dd, 1H, J=7.1, 12.3 Hz); 2.77 (dd, 1H, J=5.2 Hz); 3.58 (m, 1H); 3.85-3.97 (m, 4H); 4.54 (br s, 1H); 7.15-7.25 (m, 4H).

Stage 3

4-[2-(1,3-Dihydroisoindol-2-yl)-1-hydroxyethyl]-1-dimethylaminocyclohexanecarbonitrile 40% aqueous dimethylamine solution (1.72 ml, 12.5 mmol) was added to 4 M hydrochloric acid (706 µl), cooled to 0, in methanol (785 µl). A solution of 4-[2-(1,3-dihydroisoindol-2-yl)-1-hydroxyethyl]cyclohexanone (732 mg, 2.82 mmol) in methanol (4 ml) and tetrahydrofuran (6 ml) was then added. Potassium cyanide (445 mg, 6.67 mmol) was then added to the mixture and the mixture was stirred at room temperature overnight. Thereafter, water (80 ml) was added to the reaction mixture and the mixture was extracted with diethyl ether (3×20 ml). The combined organic phases were dried with sodium sulfate and concentrated in vacuo.

Yield: 672 mg (76%), white solid $^1$H-NMR (DMSO-d$_6$): 1.20-1.50 (m, 7H); 1.60-1.90 (m, 2H); 2.22 and 2.33 (2 s, 6H); 2.63-2.75 (m, 2H); 3.45 (m, 1H); 3.82-3.94 (m, 4H); 4.36 and 4.45 (2 d, 1H, J=in each case 4.7 Hz); 7.15-7.24 (m, 4H).

A diastereoisomer mixture in the ratio of approx. 4.5:1 was obtained.

Stage 4

2-(1,3-Dihydroisoindol-2-yl)-1-(4-dimethylamino-4-phenylcyclohexyl)ethanol

A solution of 4-[2-(1,3-dihydroisoindol-2-yl)-1-hydroxyethyl]-1-dimethylaminocyclohexanecarbonitrile (666 mg, 2.12 mmol) in anhydrous tetrahydrofuran (30 ml) was added dropwise to a 2 M solution of phenylmagnesium chloride in tetrahydrofuran (4.25 ml, 8.49 mmol), while cooling with ice, and the mixture was stirred at room temperature overnight. Saturated ammonium chloride solution and water (10 ml of each) were then added dropwise to the mixture, while cooling with ice. The tetrahydrofuran was distilled off in vacuo and the residue was extracted with diethyl ether (3×30 ml). The combined organic phases were dried with sodium sulfate and concentrated in vacuo. The crude product (761 mg) was purified by flash chromatography with chloroform/methanol (9:1). Renewed flash chromatography with chloroform (saturated with 25% aqueous ammonia solution)/methanol (95:5) gave a yield of 83 mg (10%) of beige-coloured solid.

Melting point: 130-135° C.

$^1$H-NMR (CDCl$_3$): 1.26 (s, 1H); 1.40-1.90 (m, 7H); 2.05 (s, 6H); 2.58-2.70 (m, 2H); 2.79 (dd, 1H, J=10.2, 11.8 Hz); 2.84 (dd, 1H, J=3.5, 11.8 Hz); 3.63 (m, 1H); 3.93 (d, 2H, J=11.1 Hz); 4.12 (d, 2H, J=11.1 Hz); 7.21-7.29 (m, 5H); 7.30-7.39 (m, 4H).

A diastereoisomer mixture in the ratio of approx. 4:1 was obtained.

Example 13 and Example 14

(1-(4-Dimethylamino-4-phenylcyclohexyl)-2-phenoxyethanol, Nonpolar Diastereoisomer)

(1-(4-Dimethylamino-4-phenylcyclohexyl)-2-phenoxyethanol, Polar Diastereoisomer)

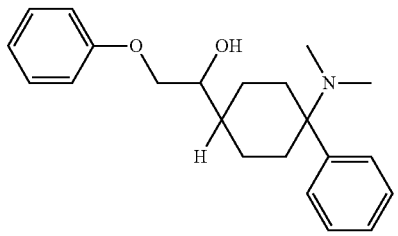

Stage 1

8-Oxiranyl-1,4-dioxaspiro[4.5]decane

A 60% strength dispersion of sodium hydride in mineral oil (1.78 g, 44.59 mmol) was taken up in dimethylsulfoxide (25 ml), and trimethylsulfoxonium iodide (9.80 g, 44.6 mmol) was added. The mixture was stirred at room temperature for 45 min. A solution of 1,4-dioxaspiro[4,5]decane-8-carbaldehyde (7.59 g, 44.6 mmol) in dimethylsulfoxide (20 ml) was then added to the mixture. The reaction mixture was stirred at 60° C. for 18 h. After cooling, the mixture was poured into water (100 ml) and extracted with diethyl ether (4×20 ml). The combined organic phases were dried with sodium sulfate and concentrated in vacuo. The crude product (4.64 g) was purified by flash chromatography with cyclohexane/ethyl acetate (4:1).

Yield: 1.09 g (13%), colourless oil $^1$H-NMR (DMSO-$d_6$): 1.10-1.85 (m, 8H); 2.50 (2H, overlapped by the DMSO signal); 2.64 (dd, 1H, J=5.0, 4.0 Hz); 2.71 (ddd, 1H, J=6.6, 4.0, 2.7 Hz); 3.84 (s, 4H).

The following product batches were obtained in an analogous manner:
a) from 1.16 g of 1,4-dioxaspiro[4,5]decane-8-carbaldehyde 247 mg, 20% of th.
b) from 2.99 g of 1,4-dioxaspiro[4,5]decane-8-carbaldehyde 560 mg, 17% of th.
c) from 7.6 g of 1,4-dioxaspiro[4,5]decane-8-carbaldehyde 7.34 g, 17% of th., this batch containing large amounts of methylene chloride and cyclohexane. The content of product was at most approx. 30% of th.

Stage 2

1-(1,4-Dioxaspiro[4.5]dec-8-yl)-2-phenoxyethanol

A 60% strength dispersion of sodium hydride in mineral oil (834 mg, 20.7 mmol) was taken up in anhydrous N,N-dimethylformamide (10 ml), and phenol (1.96 g, 20.8 mmol) was added. The mixture was stirred at room temperature for 15 min and a solution of 8-oxiranyl-1,4-dioxaspiro[4.5]decane (2.62 g, content approx. 30%, approx. 4 mmol) in N,N-dimethylformamide (6 ml) was then added. The reaction mixture was stirred at 120° C. for 5.5 h and then cooled to room temperature, water (1 ml) was added and the mixture was concentrated in vacuo. Toluene was repeatedly added to the residue and the mixture was concentrated again in vacuo each time. The crude product (2.9 g) was purified by flash chromatography (200 g, 20×5.6 cm) with cyclohexane/ethyl acetate (4:1).

Yield: 1.01 g (90%), colourless oil $^1$H-NMR (DMSO-$d_6$): 1.30-1.80 (m, 9H); 3.59 (m, 1H); 3.82-3.88 (s, 4H, overlapped by dd, 1H); 3.93 (dd, 1H, J=4.2, 9.9 Hz); 4.79 (d, 1H, J=5.4 Hz); 6.88-6.95 (m, 3H); 7.24-7.30 (m, 2H).

Stage 3

4-(1-Hydroxy-2-phenoxyethyl)cyclohexanone

2 M hydrochloric acid was added to a solution of 1-(1,4-dioxaspiro[4.5]dec-8-yl)-2-phenoxyethanol (1.25 g, 4.5 mmol) in acetone (30 ml) and the mixture was stirred at room temperature for 48 h. The acetone was removed in vacuo, the pH of the aqueous residue was rendered alkaline with 2 M sodium hydroxide solution and the aqueous residue was extracted with methylene chloride (4×20 ml). The combined organic phases were dried with sodium sulfate and concentrated in vacuo.

Yield: 928 mg (88%), yellowish oil.

$^1$H-NMR (DMSO-$d_6$): 1.45-1.65 (m, 2H); 1.88-2.13 (m, 3H); 2.15-2.26 (m, 2H); 2.31-2.45 (m, 2H); 3.72 (m, 1H); 3.90 (dd, 1H, J=6.2, 9.9 Hz); 3.99 (dd, 1H, J=4.4, 9.9 Hz); 4.96 (d, 1H, J=5.4 Hz); 6.90-6.98 (m, 3H); 7.25-7.32 (m, 2H).

Stage 4

4-[1-(1-Ethoxy-ethoxy)-2-phenoxyethyl]cyclohexanone

Pyridinium tosylate (15 mg, 0.06 mmol) and ethyl vinyl ether (339 mg, 450 μl, 4.70 mmol) were added to a solution of 4-(1-hydroxy-2-phenoxyethyl)cyclohexanone (919 mg, 3.92 mmol) in anhydrous methylene chloride (20 ml) and the mixture was stirred at room temperature overnight. Methylene chloride (20 ml) was then added to the mixture and the mixture was washed with water, 5% strength sodium bicarbonate solution and saturated sodium chloride solution (50 ml of each). The organic phase was dried with sodium sulfate and concentrated in vacuo.

The crude product (1.09 g) was purified by flash chromatography with cyclohexane/ethyl acetate (4:1).

Yield: 929 mg (77%), colourless oil $^1$H-NMR (DMSO-$d_6$): 1.02-1.13 (m, 3H); 1.21 (dd, 3H, J=5.2, 9.1 Hz); 1.44-1.70 (m, 3H); 1.90-2.30 (m, 4H); 2.32-2.47 (m, 2H); 3.38-3.64 (m, 2H); 3.71-3.88 (m, 1H); 3.94-4.15 (m, 2H); 4.80 and 4.90 (2 q, 1H, J=5.3 Hz); 6.90-6.94 (m 3H); 7.29 (t, 2H, J=8.0 Hz).

The product was obtained as a diastereoisomer mixture.

Stage 5

1-Dimethylamino-4-[1-(1-ethoxy-ethoxy)-2-phenoxyethyl]cyclohexanecarbonitrile

40% aqueous dimethylamine solution (1.73 ml, 13.7 mmol) was added to a mixture of 4 M hydrochloric acid (747 μl) and methanol (448 μl), while cooling with ice, and the mixture was added to 4-[1-(1-ethoxy-ethoxy)-2-phenoxyethyl]cyclohexanone (880 mg, 2.87 mmol), before potassium cyanide (448 mg, 6.88 mg) was added. Tetrahydrofuran (3 ml) was also added for solubilization. The reaction mixture was stirred at room temperature for 6 h, water (50 ml) was then added and the mixture was extracted with diethyl ether (4×30 ml). The combined organic phases were concentrated in vacuo, the residue was taken up in methylene chloride (30 ml) and the mixture was washed with water (30 ml). The organic phase was dried with sodium sulfate and concentrated in vacuo.

Yield: 877 mg (84%), colourless oil $^1$H-NMR (DMSO-$d_6$): 1.00-1.12 (m, 3H); 1.16-1.24 (m, 3H); 1.30-2.00 (m, 8H); 2.10-2.30 (m, 7H); 3.40-3.70 (m, 3H); 4.00-4.10 (m, 2H); 4.74-4.90 (m, 1H); 6.90-6.99 (m, 3H); 7.25-7.32 (m, 2H).

The product is in the form of a mixture of diastereoisomers.

Stage 6

{4-[1-(1-Ethoxy-ethoxy)-2-phenoxyethyl]-1-phenylcyclohexyl}dimethylamine

A solution of 1-dimethylamino-4-[1-(1-ethoxy-ethoxy)-2-phenoxyethyl]cyclohexanecarbonitrile (871 mg, 2.4 mmol) in anhydrous tetrahydrofuran (15 ml) was added dropwise to a 2 M solution of phenylmagnesium chloride in tetrahydrofuran (3.6 ml, 7.3 mmol), while cooling with ice. The mixture was stirred at room temperature overnight and saturated ammonium chloride solution and water (5 ml of each) were then added. The phases were separated and the aqueous phase was extracted with diethyl ether (3×20 ml). The combined organic phases were dried with sodium sulfate and concentrated in vacuo.

Yield: 946 mg (99%), yellowish oil.

$^1$H-NMR (DMSO-$d_6$): 0.90-1.26 (m, 6H); 1.26-1.80 (m, 9H); 1.93 (s, 6H); 2.61-2.71 (m, 1H); 3.40-3.69 (m, 2H); 3.93-4.14 (m, 2H); 4.71-4.92 (m, 1H); 6.70-7.70 (m, 10H).

The product was obtained as a diastereoisomer mixture.

Stage 7

1-(4-Dimethylamino-4-phenylcyclohexyl)-2-phenoxyethanol

2 M hydrochloric acid (10 ml) was added to a solution of {4-[1-(1-ethoxy-ethoxy)-2-phenoxyethyl]-1-phenylcyclohexyl}dimethylamine (892 mg, 2.16 mmol) in acetone (30 ml) and the mixture was stirred at room temperature overnight. The pH of the mixture was then rendered alkaline with 0.5 M sodium hydroxide solution and the mixture was subsequently extracted with methylene chloride (3×30 ml). The combined organic phases were dried with sodium sulfate and concentrated in vacuo. The crude product (1.26 g) was purified by flash chromatography with ethyl acetate/methanol (9:1→0:1).

1-(4-Dimethylamino-4-phenylcyclohexyl)-2-phenoxyethanol (Nonpolar Diastereoisomer)

Yield: 317 mg (43%), yellowish oil.

$^1$H-NMR (DMSO-$d_6$): 1.22-1.38 (m, 2H); 1.40-1.74 (m, 5H); 1.92 (s, 6H); 2.58-2.74 (m, 2H); 3.56-3.65 (m, 1H); 3.88 (dd, 1H, J=10.0, 6.3 Hz); 3.98 (dd, 1H, J=10.0, 4.0 Hz); 4.78 (d, 1H, J=5.5 Hz); 6.88-6.97 (m, 3H); 7.18-7.37 (m, 7H).

1-(4-Dimethylamino-4-phenylcyclohexyl)-2-phenoxyethanol (Polar Diastereoisomer)

Yield: 41 mg (5%), yellowish solid

Melting point: 145-147° C.

$^1$H-NMR (DMSO-$d_6$): 0.80-1.10 (m, 2H); 1.38-1.54 (m, 4H); 1.72 (br d, 1H, J=12.8 Hz); 1.89 (s, 6H); 2.58-2.74 (m, 2H); 3.40-3.52 (m, 1H); 3.77 (dd, 1H, J=9.9, 6.1 Hz); 3.84 (dd, 1H, J=9.9, 4.4 Hz); 4.67 (br s, 1H); 6.84-6.92 (m, 3H); 7.20-7.40 (m, 7H).

Example 15

2-Benzyloxy-1-(4-dimethylamino-4-phenylcyclohexyl)ethanol

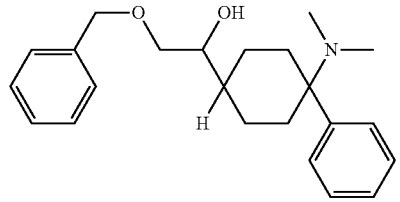

Stage 1

By replacing phenol by benzyl alcohol in Example 13 and 14, stage 2 and subsequent analogous reaction, Example 15 was obtained:

$^1$H-NMR (DMSO-$d_6$): 1.15-1.68 (m, 8H); 1.92 (s, 6H); 2.52-2.70 (m, 2H); 3.35-3.50 (m, 2H); 4.49 (m, 3H); 7.18-7.40 (m, 10 H).

$^{13}$C-NMR (DMSO-$d_6$): 22.3; 23.7; 32.6; 32.7; 37.5; 58.1; 72.1; 72.7; 72.9; 126.1 (br); 126.3 (br); 127.1 (br); 127.4; 128.1; 138.7; 139.7.

Only one diastereoisomer was isolated.

Example 16

2-(Cyclohexyloxy)-1-(4-(dimethylamino)-4-phenylcyclohexyl)ethanol

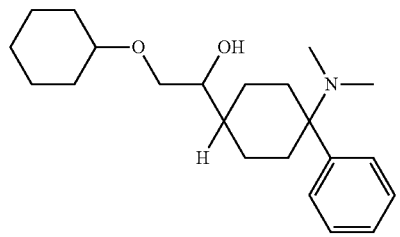

By replacing phenol by cyclohexanol in Example 13 and 14, stage 2 and subsequent analogous reaction, Example 16 was obtained:

$^1$H-NMR (DMSO-$d_6$): 1.10-1.57 (m, 16H); 1.80 (m, 2H); 1.92 (s, 6H); 2.63 (br d, 2H, J=13.9 Hz); 3.22 (m, 1H); 3.28-3.45 (m, 3H); 4.31 (d, 1H, J=4.7 Hz); 7.23 (m, 1H); 7.28-7.35 (m, 4H).

$^{13}$C-NMR (DMSO-$d_6$): 22.7; 23.2; 23.7; 25.3; 31.7; 32.6; 37.4; 58.3; 70.2; 73.0; 76.4; 126.1; 126.5; 127.0; 139.6.

Only one diastereoisomer was isolated.

Example 17

2-Cyclohexyloxy-1-(4-dimethylamino-4-thiophen-2-yl-cyclohexyl)ethanol

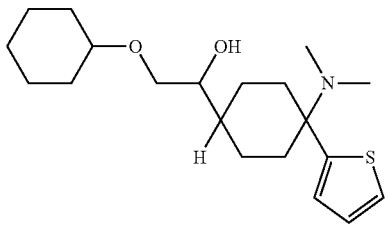

In an analogous procedure to Example 16, replacing phenylmagnesium chloride by 2-thienylmagnesium bromide in stage 6, Example 17 was obtained analogously.

$^1$H-NMR (DMSO-d$_6$): 1.10-1.57 (m, 15H); 1.80 (m, 2H); 1.99 (s, 6H); 2.42 (d, 2H, J=13.7 Hz); 3.21 (m, 1H); 3.27-3.44 (m, 3H); 4.34 (d, 1H, J=4.7 Hz); 6.89 (dd, 1H, J=1.1 and 3.4 Hz); 7.02 (dd, 1H, J=3.4 and 5.1 Hz); 7.37 (dd, 1H, J=1.1 and 5.1 Hz).

$^{13}$C-NMR (DMSO-d$_6$): 22.2; 23.2; 23.6; 25.3; 31.7; 35.1; 37.3; 58.1; 70.1; 72.9; 76.4; 122.8; 123.5; 126.0; 145.2.

Only one diastereoisomer was isolated.

Example 18

1-(4-Dimethylamino-4-phenylcyclohexyl)-2-indol-1-yl-ethanol

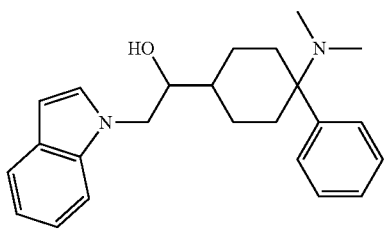

By replacing phenol by indole in Example 13 and 14, stage 2 and subsequent analogous reaction, Example 18 was obtained:

$^1$H-NMR (CDCl$_3$): 1.44-1.64 (m, 3H); 1.64-1.90 (m, 4H); 2.05 (s, 6H); 2.65-2.74 (m, 2H); 3.89 (ddd, 1H, J=2.8, 6.6, 9.2 Hz); 4.06 (dd, 1H, J=9.1, 14.3 Hz); 4.40 (dd, 1H, J=2.8, 14.3 Hz); 6.52 (d, 1H, J=3.1 Hz); 7.11 (m, 1H); 7.18 (d, 1H, J=3.1 Hz); 7.22 (ddd, 1H, J=1.2, 7.1, 8.2 Hz); 7.16-7.42 (m, 6H); 7.64 (d, 1H, J=7.9 Hz).

Example 19

1-(4-Dimethylamino-4-phenylcyclohexyl)-2-phenylsulfanylethanol

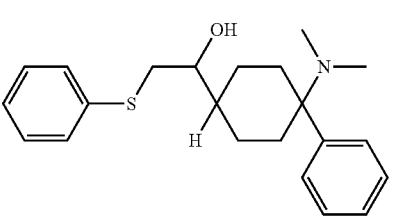

By replacing phenol by thiophenol in Example 13 and 14, stage 2 and subsequent analogous reaction, Example 19 was obtained:

$^1$H-NMR (CDCl$_3$): 1.48-1.64 (m, 4H); 1.66-1.82 (m, 4H); 2.10 (s, 6H); 2.60-2.72 (m, 2H); 2.94 (dd, 1H, J=8.8 and 13.6 Hz); 3.29 (dd, 1H, J=3.4 and 13.6 Hz) 3.64 (m, 1H); 7.21 (m, 1H); 7.25-7.43 (m, 9H).

LC-MS (method 8): [M+H]$^+$: m/z=356.2, R$_t$=2.6 min.

Example 20

2-(4-(Dimethylamino)-4-phenylcyclohexyl)-1-phenoxypropan-2-ol

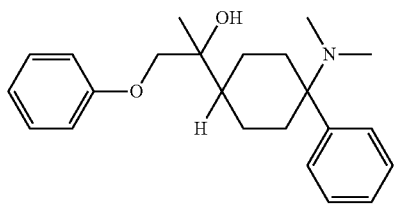

Stage 7 was prepared analogously to Example 13 and 14, and starting from this the synthesis of Example 20 was carried out as described below:

Stage 8

1-(4-Dimethylamino-4-phenylcyclohexyl)-2-phenoxyethanone

A 15% solution of Dess-Martin periodinane in methylene chloride (22.9 g, 8.10 mmol) was added to a solution of 1-(4-dimethylamino-4-phenylcyclohexyl)-2-phenoxyethanol (800 mg, 2.35 mmol) in anhydrous methylene chloride (25 ml). The mixture was stirred at room temperature for 4 h and then at 40° C. for 1.5 h and diethyl ether (100 ml) was then added. The suspension was washed with 25% potassium carbonate solution, 5% sodium bicarbonate solution, 1 M sodium thiosulfate solution and water (50 ml of each). The organic phase was dried with sodium sulfate and concentrated i. vac.

Yield: 931 mg (>100%), yellowish solid $^1$H-NMR (DMSO-d$_6$): 1.40-1.53 (m, 2H); 1.62-1.72 (m, 2H); 1.75-1.88 (m, 2H); 1.95 (s, 6H); 2.58-2.70 (m, 3H); 4.94 (s, 2H); 6.86-6.90 (m, 2H); 6.91-6.96 (m, 1H); 7.25-7.30 (m, 3H); 7.33-7.37 (m, 4H).

Stage 9

2-(4-Dimethylamino-4-phenylcyclohexyl)-1-phenoxypropan-2-ol

A 3 M solution of methylmagnesium bromide in diethyl ether (8.8 ml, 26.7 mmol) was added to a suspension of the product from stage 7 (crude product, 300 mg, max. 0.89 mmol) in anhydrous tetrahydrofuran (30 ml), under argon and while cooling with ice, and the mixture was stirred at room temperature for 3 h. Saturated ammonium chloride solution and water (10 ml of each) were then added dropwise to the mixture, while cooling with ice, and the mixture was extracted with diethyl ether (3×20 ml). The combined organic phases were dried with sodium sulfate and concentrated i.

vac. The crude product (167 mg) was purified by flash chromatography (20 g, 20×2.0 cm) with ethyl acetate/methanol (9:1).

Yield: 102 mg (32%, based on stage 6), colourless oil
$^1$H-NMR (DMSO-$d_6$): 1.15 (s, 3H); 1.20-1.30 (m, 2H); 1.50-1.70 (m, 5H); 1.92 (s, 6H); 2.71 (br, d, 2H, J=14.3 Hz); 3.76 (d, 1H, J=9.3 Hz); 3.83 (d, 1H, J=9.3 Hz); 4.38 (s, 1H); 6.88-6.97 (m, 3H); 7.18-7.40 (m, 7H).
LC-MS (method 7): [M+H]$^+$: m/z=354.3, $R_t$=3.3 min.

Comparison Example 1

3-{3-[4-(Dimethylamino)-4-phenylcyclohexyl]-3-hydroxyprop-1-ynyl}-1H-indole-1-carboxylic acid tert-butyl ester

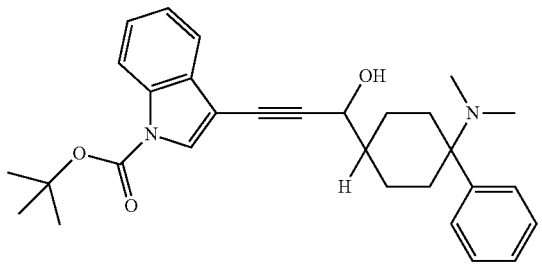

The synthesis of this compound and the following data on the biological activity are described in the literature (WO 04/043900)

Comparison Example 2

4-(Dimethylamino)-4-phenyl-4',9'-dihydro-3'H-spiro [cyclohexane-1,1'-pyrano[3,4-b]indol]-2-yl)methanol

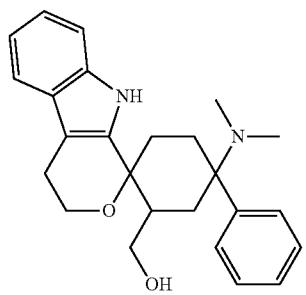

Stage 1

4-(Dimethylamino)-4-phenyl-4',9'-dihydro-3'H-spiro [cyclohexane-1'-pyrano[3,4-b]indol]-2-yl)methanol (One of 4 Possible Racemic Diastereoisomer Pairs)

2-(4-(Dimethylamino)-4-phenyl-4',9'-dihydro-3'H-spiro [cyclohexane-1,1'-pyrano[3,4-b]indol]-2-yl)acetic acid methyl ester (190 mg, 0.44 mmol) was dissolved in a mixture of 2 N HCl (20 ml) and ethanol (20 ml) and the mixture was stirred at RT for 18 h. For working up, the ethanol was stripped off in vacuo and the aqueous residue was neutralized with NaHCO$_3$ and rendered strongly basic with 2 N NaOH. The aqueous solution was extracted with ethyl acetate (3×10 ml). The combined organic phases were dried over MgSO$_4$ and then concentrated. The solid residue obtained proved to be one of the four possible diastereoisomers of the desired alcohol in the pure form. The product was obtained in this way in a yield of 153 mg (89%) with a melting point of 219-233° C. (from propan-2-ol).
$^{13}$C-NMR (101 MHz, DMSO-$d_6$, δ ppm): 22.1, 27.9, 30.5, 31.0, 37.9, 43.9, 59.1, 60.8, 61.6, 73.8, 106.5, 111.0, 117.3, 118.2, 120.4, 126.2, 126.3, 127.59, 127.63, 135.9, 136.6, 137.4

Investigations of the Activity of the Compounds According to the Invention

Measurement of the ORL1 Binding

The compounds were investigated in a receptor binding assay with $^3$H-nociceptin/orphanin FQ with membranes from recombinant CHO-ORL1 cells. This test system was conducted in accordance with the method described by Ardati et al. (Mol. Pharmacol., 51, 1997, p. 816-824). The concentration of $^3$H-nociceptin/orphanin FQ in these experiments was 0.5 nM. The binding assays were carried out with in each case 20 μg of membrane protein per 200 μl batch in 50 mM hepes, pH 7.4, 10 mM MgCl$_2$ and 1 mM EDTA. The binding to the ORL1 receptor was determined using in each case 1 mg of WGA-SPA beads (Amersham-Pharmacia, Freiburg) by incubation of the batch at RT for one hour and subsequent measurement in a Trilux scintillation counter (Wallac, Finland). The affinity is stated in Table 1 as the nanomolar $K_i$ value in or % inhibition at c=1 μM.

Measurement of the μ Binding

The receptor affinity for the human μ opiate receptor was determined in a homogeneous setup in microtitre plates. For this, dilution series of the compound to be tested in each case were incubated with a receptor membrane preparation (15-40 μg of protein per 250 μl of incubation batch) of CHO-K1 cells which express the human μ opiate receptor (RB-HOM receptor membrane preparation from NEN, Zaventem, Belgium) in the presence of 1 nmol/l of the radioactive ligand [$^3$H]-naloxone (NET719, NEN, Zaventem, Belgium) and of 1 mg of WGA-SPA-Beads (wheat germ agglutinin SPA beads from Amersham/Pharmacia, Freiburg, Germany) in a total volume of 250 μl for 90 minutes at room temperature. 50 mmol/l of Tris-HCl supplemented with 0.05 wt. % of sodium azide and with 0.06 wt. % of bovine serum albumin was used as the incubation buffer. 25 μmol/l of naloxone were additionally added for determination of the non-specific binding. After the end of the ninety-minute incubation time, the microtitre plates were centrifuged for 20 minutes at 1,000 g and the radioactivity was measured in a β-counter (Microbeta-Trilux, PerkinElmer Wallac, Freiburg, Germany). The percentage displacement of the radioactive ligand from its binding to the human μ opiate receptor was determined at a concentration of the test substances of 1 μmol/l and stated as the percentage inhibition (% inhibition) of the specific binding. Starting from the percentage displacement by various concentrations of the substances of the general formula I to be tested, IC$_{50}$ inhibitory concentrations which cause a 50 percent displacement of the radioactive ligand were calculated in some cases. By conversion by means of the Cheng-Prusoff relationship, $K_i$ values for the test substances were obtained. In some cases determination of the $K_i$ value was dispensed with and only the inhibition at a test concentration of 1 μM was determined.

Testing of Analgesia in the Tail Flick Test in Rats

The analgesic activity of the test compounds of Example 3 was investigated in the focal ray (tail flick) test in rats in accordance with the method of D'Amour and Smith (J. Pharm. Exp. Ther. 72, 74 79 (1941)). Female Sprague-Dawley weighing between 134 and 189 g were used for this. The animals were placed individually in special test cages and the base of the tail was exposed to a focused heat ray of a lamp (Tail-flick type 50/08/1.bc, Labtec, Dr Hess). The intensity of the lamp was adjusted such that in the case of untreated animals the time between switching on of the lamp to sudden pulling away of the tail (pain latency) was 2.5-5 seconds. Before administration of a test compound, the animals were pretested twice in the course of 30 minutes and the mean of these measurements was calculated as the pretest mean The pain was measured 20, 40 and 60 min after intravenous administration. The analgesic action was determined as the increase in pain latency (% MPE) according to the following formula:

$$[(T_1-T_0)/(T_2-T_0)] \times 100$$

In this formula, $T_0$ is the latency period before and $T_1$ the latency period after administration of the substance, $T_2$ is the maximum exposure time (12 sec).

To determine the dose dependency, the particular test compound was administered in 3-5 logarithmically increasing doses, which included the threshold and the maximum active dose in each case, and the $ED_{50}$ values were determined with the aid of regression analysis. The $ED_{50}$ calculation was performed at the action maximum, 20 minutes after intravenous administration of the substance.

Nephelometric Solubility Study (Phosphate Buffer pH 7.4)

This method investigates the solubility of a substance at fixed concentrations (1 µM, 3 µM, 10 µM, 30 µM and 100 µM) in 10 mM phosphate buffer solution at pH 7.4. A 10 mM solution of the substances in DMSO is initially required, from which 100-fold stock solutions of the abovementioned concentration levels are prepared, again in DMSO, the final DMSO concentration in the test batch being 1% (v/v). The experiment is carried out in a multiple determination. After addition of the DMSO stock solutions to the buffer, the batch is incubated at 37° C. for 2 h, before a determination of the absorption at 620 nm takes place. If the absorption of the samples rises above that of the pure buffer/DMSO solution, this is an indicator of formation of a precipitate. The lower solubility limit ("lower boundary") is the concentration which precedes that with the first formation of a precipitate (e.g. 3 µM, if formation of a precipitate was detected at 10 µM).

Comparison Studies

|  | % inhibition (ORL1) [1 µM] | Ki (ORL1) mean [nm] | % inhibition (µ) [1 µM] | Ki (µ) mean [nm] | TF rat $ED_{50}$ i.v. [µg/kg] | Solubility (pH 7) [µmol/l] |
|---|---|---|---|---|---|---|
| Example 1 | 93 |  | 99 |  |  |  |
| Example 3 |  | 1.9 |  | 3.2 | 31.7 |  |
| Example 4 |  | 605 |  | 2075 |  | 100 |
| Example 5 | 97 |  | 103 |  |  |  |
| Example 6 |  | 0.76 |  | 1.3 |  |  |
| Example 7 |  | 0.94 |  | 1.8 |  |  |
| Example 8 |  | 400 |  | 11 |  |  |
| Example 9 |  | 370 |  | 11.3 |  |  |
| Example 12 | 71 |  | 99 |  |  |  |
| Example 13 |  | 30 |  | 6.5 |  |  |
| Example 15 |  | 130 |  | 10.7 |  |  |
| Example 16 |  | 91 |  | 12 |  |  |
| Example 17 |  | 45 |  | 4.6 |  |  |
| Example 18 |  | 4.1 |  | 1.0 |  |  |
| Comparison 1 |  | 730 |  | 86 |  |  |
| Comparison 2 | 80 |  | 99 |  |  | 10 |

It can be seen from the present table that compared with the similar structure of the known compound of Comparison Example 1, the compounds according to the invention of Examples 1, 3, 4, 5, 6, 7, 8, 9, 12, 13, 15, 16, 17 and 18 show a surprisingly high binding to the ORL1 receptor and sometimes additionally also to the µ opioid receptor. It can furthermore be seen that the compound according to the invention according to Example 4 has an about 10-fold better solubility in aqueous media than the compound of Comparison Example 2.

The invention claimed is:

1. A compound of the formula (1):

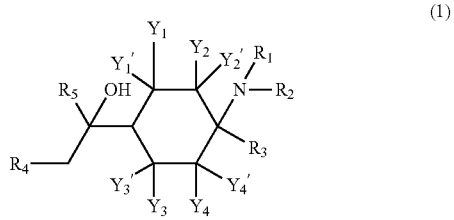

(1)

wherein $Y_1$, $Y_1'$, $Y_2$, $Y_2'$, $Y_3$, $Y_3'$, $Y_4$ and $Y_4'$ in each case independently of each other are chosen from the group consisting of —H, —F, —Cl, —Br, —I, —CN, —NO$_2$, —CHO, —R$_0$, —C(=O)R$_0$, —C(=O)H, —C(=O)—OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)N(R$_0$)$_2$, —SH, —SR$_0$, —S(=O)$_{1-2}$R$_0$, —S(=O)$_{1-2}$OH, —S(=O)$_{1-2}$OR$_0$, —S(=O)$_{1-2}$NH$_2$, —S(=O)$_{1-2}$NHR$_0$ or —S(=O)$_{1-2}$N(R$_0$)$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)NHR$_0$, and —NHC(=O)N(R$_0$)$_2$; or $Y_1$ and $Y_1'$, or $Y_2$ and $Y_2'$, or $Y_3$ and $Y_3'$, or $Y_4$ and $Y_4'$ together represent =O;

$R_0$ in each case independently represents —C$_{1-8}$-aliphatic, —C$_{3-12}$-cycloaliphatic, -aryl, -heteroaryl, —C$_{1-8}$-aliphatic-C$_{3-12}$-cycloaliphatic, —C$_{1-8}$-aliphatic-aryl, —C$_{1-8}$-aliphatic-heteroaryl, —C$_{3-8}$-cycloaliphatic-C$_{1-8}$-aliphatic, —C$_{3-8}$-cycloaliphatic-aryl or —C$_{3-8}$-cycloaliphatic-heteroaryl;

$R_1$ and $R_2$ independently of each other represent —H or —C$_{1-8}$-aliphatic; or $R_1$ and $R_2$ together form a ring and represent —(CH$_2$)$_{2-4}$—;

$R_3$ represents —R$_0$;

$R_4$ represents —H, —F, —Cl, —Br, —I, —R$_0$, —C(=O)H, —C(=O)OR$_0$, —CN, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)—N(R$_0$)$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NHR$_0$, —NHC(=O)—N(R$_0$)$_2$, —NO$_2$, —SH, —SR$_0$, —S(=O)$_{1-2}$R$_0$, —S(=O)$_{1-2}$OH, —S(=O)$_{1-2}$OR$_0$, —S(=O)$_{1-2}$NH$_2$, —S(=O)$_{1-2}$NHR$_0$, —S(=O)$_{1-2}$N(R$_0$)$_2$, —OS(=O)$_{1-2}$R$_0$, —OS(=O)$_{1-2}$OH, —OS(=O)$_{1-2}$OR$_0$, —OS(=O)$_{1-2}$NH$_2$, —OS(=O)$_{1-2}$NHR$_0$ or —OS(=O)$_{1-2}$N(R$_0$)$_2$;

$R_5$ represents —H, —R$_0$, —C(=O)H, —C(=O)R$_0$, —C(=O)OR$_0$, —CN, —C(=O)NH$_2$, —C(=O)NHR$_0$ or —C(=O)N(R$_0$)$_2$;

wherein

"aliphatic" in each case is a branched or unbranched, saturated or mono- or polyunsaturated, unsubstituted or mono- or polysubstituted, aliphatic hydrocarbon radical;

"cycloaliphatic" in each case is a saturated or mono- or polyunsaturated, unsubstituted or mono- or polysubstituted, alicyclic, mono- or multicyclic hydrocarbon radical;

wherein with respect to "aliphatic" and "cycloaliphatic", "mono- or polysubstituted" is substitution once or several times by substituents chosen independently of each other from the group consisting of —F, —Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$,—OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)—NHR$_0$, —NH—C(=O)N(R$_0$)$_2$, —Si(R$_0$)$_3$ and —PO(OR$_0$)$_2$;

"aryl" in each case independently represents a carbocyclic ring system having at least one aromatic ring, but without hetero atoms in this ring, wherein the aryl radicals can optionally be fused with further saturated, (partially) unsaturated or aromatic ring systems, which in their turn can have one or more hetero ring atoms, in each case independently of each other chosen from N, O and S, and wherein each aryl radical can be unsubstituted or mono- or polysubstituted, wherein the substituents on aryl can be identical or different and can be in any desired and possible position of the aryl;

"heteroaryl" represents a 5-, 6- or 7-membered cyclic aromatic radical which contains 1, 2, 3, 4 or 5 hetero atoms, wherein the hetero atoms are identical or different and are nitrogen, oxygen or sulfur and the heteroaryl can be unsubstituted or mono- or polysubstituted; wherein in the case of substitution on the heteroaryl the substituents can be identical or different and can be in any desired and possible position of the heteroaryl; and wherein the heterocyclyl can also be part of a bi- or polycyclic system;

wherein with respect to "aryl" and "heteroaryl", "mono- or polysubstituted" is substitution once or several times of the ring system by substituents chosen from the group consisting of —F, Cl, —Br, —I, —CN, —NO$_2$, —CHO, =O, —R$_0$, —C(=O)R$_0$, —C(=O)H, —C(=O)OH, —C(=O)OR$_0$, —C(=O)NH$_2$, —C(=O)NHR$_0$, —C(=O)N(R$_0$)$_2$, —OH, —O(CH$_2$)$_{1-2}$O—, —OR$_0$, —OC(=O)H, —OC(=O)R$_0$, —OC(=O)OR$_0$, —OC(=O)NHR$_0$, —OC(=O)—N(R$_0$)$_2$, —SH, —SR$_0$, —SO$_3$H, —S(=O)$_{1-2}$—R$_0$, —S(=O)$_{1-2}$NH$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NH$_2$, —NHC(=O)—NHR$_0$, —NH—C(=O)N(R$_0$)$_2$, —Si(R$_0$)$_3$ and —PO(OR$_0$)$_2$; wherein N ring atoms optionally present can in each case be oxidized;

in the form of an individual stereoisomer or mixture thereof, a free compound and/or a physiologically acceptable salt and/or solvate thereof.

2. Compound according to claim 1, wherein R$_4$ represents —H, —F, —Cl, —Br, —I, —C$_{3-12}$-cycloaliphatic, -aryl, -heteroaryl, —C$_{3-8}$-cycloaliphatic-C$_{1-8}$-aliphatic, —C$_{3-8}$-cycloaliphatic-aryl, —C$_{3-8}$-cycloaliphatic-heteroaryl, —C(=O)H, —C(=O)R$_0$, —C(=O)OR$_0$, —CN, —C(=O)NH$_2$, —C(=O)NHR$_0$, —C(=O)N(R$_0$)$_2$, —OH, —OR$_0$, —OC(=O)H, —OC(=O)R$_0$, —OC(=O)OR$_0$, —OC(=O)NHR$_0$, —OC(=O)—N(R$_0$)$_2$, —NH$_2$, —NHR$_0$, —N(R$_0$)$_2$, —N$^+$(R$_0$)$_3$, —N$^+$(R$_0$)$_2$O$^-$, —NHC(=O)R$_0$, —NHC(=O)OR$_0$, —NHC(=O)NHR$_0$, —NHC(=O)—N(R$_0$)$_2$, —NO$_2$, —SH, —SR$_0$, —S(=O)$_{1-2}$R$_0$, —S(=O)$_{1-2}$OH, —S(=O)$_{1-2}$OR$_0$, —S(=O)$_{1-2}$NH$_2$, —S(=O)$_{1-2}$NHR$_0$ or —S(=O)$_{1-2}$N(R$_0$)$_2$, —OS(=O)$_{1-2}$R$_0$, —OS(=O)$_{1-2}$OH, OS(=O)$_{1-2}$OR$_0$, —OS(=O)$_{1-2}$NH$_2$, —OS(=O)$_{1-2}$NHR$_0$ or —OS(=O)$_{1-2}$N(R$_0$)$_2$.

3. Compound according to claim 1, wherein Y$_1$, Y$_1$', Y$_2$, Y$_2$', Y$_3$, Y$_3$', Y$_4$ and Y$_4$' in each case represent —H.

4. Compound according to claim 1, wherein R$_3$ is chosen from the group consisting of -phenyl, -benzyl or -phenethyl, in each case unsubstituted or mono- or polysubstituted on the ring; —C$_{1-5}$-aliphatic, —C$_{4-6}$-cycloaliphatic, -pyridyl, -thienyl, -thiazolyl, -imidazolyl, -1,2,4-triazolyl and -benzimidazolyl, in each case unsubstituted or mono- or polysubstituted.

5. Compound according to claim 1, wherein R$_5$ represents —H.

6. Compound according to claim 1, which has the formula (4), (5), (6), (7), (8) or (9):

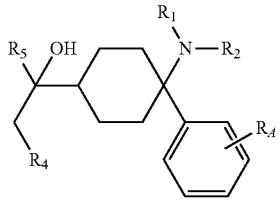

(4)

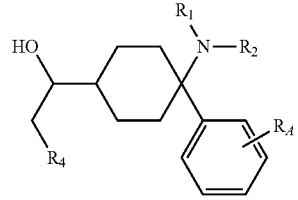

(5)

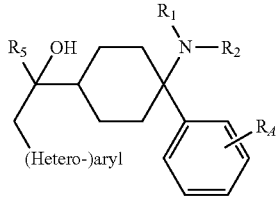

(6)

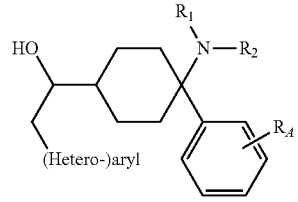

(7)

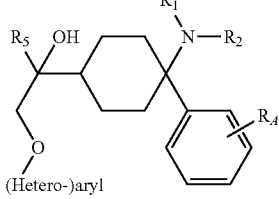

(8)

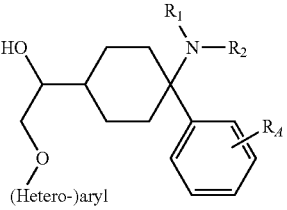

(9)

wherein, if present,

R$_4$ represents —H, —F, —Cl, —CN, —NO$_2$ or —OCH$_3$; and (Hetero-)aryl represents heteroaryl or aryl, in each case unsubstituted or mono- or polysubstituted.

7. Compound according to claim 1, chosen from the group consisting of 1-(4-(dimethylamino)-4-phenylcyclohexyl)-2-phenylethanol;

1-(4-(dimethylamino)-4-phenylcyclohexyl)-2-phenoxyethanol;

1-(4-(dimethylamino)-4-phenylcyclohexyl)-2-(1H-indol-1-yl)ethanol;

1-(4-(dimethylamino)-4-phenylcyclohexyl)-2-(isoindolin-2-yl)ethanol, 1-(4-(dimethylamino)-4-phenylcyclohexyl)-2-(4-fluorophenyl)ethanol;

1-(4-(dimethylamino)-4-(3-fluorophenyl)cyclohexyl)-2-phenylethanol;

1-(4-(dimethylamino)-4-(3-methoxyphenyl)cyclohexyl)-2-phenylethanol;

1-(4-(dimethylamino)-4-(thiophen-2-yl)cyclohexyl)-2-phenylethanol;

1-(4-butyl-4-(dimethylamino)cyclohexyl)-2-phenylethanol;

1-cyclopentyl-2-(4-(dimethylamino)-4-phenylcyclohexyl)-3-phenylpropan-2-ol;

1-(4-(dimethylamino)-4-phenylcyclohexyl)-1-phenyl-2-(pyridin-4-yl)ethanol;

1-(4-(dimethylamino)-4-phenylcyclohexyl)-2-(phenylthio)ethanol;

1-(4-(dimethylamino)-4-phenylcyclohexyl)-2-(phenylsulfonyl)ethanol;

2-(cyclohexyloxy)-1-(4-(dimethylamino)-4-phenylcyclohexyl)ethanol;

2-(benzyloxy)-1-(4-(dimethylamino)-4-phenylcyclohexyl)ethanol;

1-(4-(dimethylamino)-4-phenylcyclohexyl)-2-phenethoxyethanol;

2-((1H-indol-3-yl)methoxy)-1-(4-(dimethylamino)-4-phenylcyclohexyl)ethanol;

2-(2-(1H-indol-3-yl)ethoxy)-1-(4-(dimethylamino)-4-phenylcyclohexyl)ethanol;

1-(4-(dimethylamino)-4-phenylcyclohexyl)-2-((2-(triethylsilyl)-1H-indol-3-yl)-methoxy)ethanol;

1-(2-(4-(dimethylamino)-4-(3-fluorophenyl)cyclohexyl)-2-hydroxyethyl)piperidin-2-one;

2-(4,4a-dihydro-1H-pyrido[3,4-b]indol-2(3H,9H,9aH)-yl)-1-(4-(dimethylamino)-4-(3-fluorophenyl)cyclohexyl)ethanol;

1-cinnamoyl-3-(2-(4-(dimethylamino)-4-(3-fluorophenyl)cyclohexyl)-2-hydroxyethyl)tetrahydropyrimidin-2(1H)-one;

2-(4-(dimethylamino)-4-phenylcyclohexyl)-1-phenylpropan-2-ol;

2-(4-(dimethylamino)-4-phenylcyclohexyl)-1,3-diphenylpropan-2-ol;

2-(4-(dimethylamino)-4-phenylcyclohexyl)-1-phenyl-3-(pyridin-2-yl)propan-2-ol;

2-(4-(dimethylamino)-4-phenylcyclohexyl)-1-phenyl-3-(pyridin-3-yl)propan-2-ol; and 2-(4-(dimethylamino)-4-phenylcyclohexyl)-1-phenyl-3-(pyridin-4-yl)propan-2-ol;

or a physiologically acceptable salt thereof.

8. A pharmaceutical composition comprising a therapeutically effective amount of at least one compound according to claim 1 in the form of an individual stereoisomer or mixture thereof, a free compound and/or a physiologically acceptable salt thereof, and optionally one or more suitable additives and/or auxiliary substances and/or optionally further active compounds.

9. A method of treating pain in a patient in need of such treatment, said method comprising administering to said patient an effective amount therefor of a compound according to claim 1 in the form of an individual stereoisomer or mixture thereof, a free compound and/or a physiologically acceptable salt thereof.

10. A method for treating a condition selected from the group consisting of anxiety states, of stress and syndromes associated with stress, depression, epilepsy, Alzheimer's disease, senile dementia, general cognitive dysfunctions, learning and memory disorders (as a nootropic), withdrawal symptoms, alcohol and/or drug and/or medicament abuse and/or dependency, sexual dysfunctions, cardiovascular diseases, hypotension, hypertension, tinnitus, pruritus, migraine, impaired hearing, lack of intestinal motility, impaired food intake, anorexia, obesity, locomotor disorders, diarrhoea, cachexia, urinary incontinence or as a muscle relaxant, anticonvulsive or anaesthetic or for co-administration in treatment with an opioid analgesic or with an anaesthetic, for diuresis or antinatriuresis, anxiolysis, for modulation of motor activity, for modulation of neurotransmitter secretion and treatment of neurodegenerative diseases associated therewith, for treatment of withdrawal symptoms and/or for reduction of the addiction potential of opioids, said method comprising administering to a patient in need of such treatment an effective amount therefor of a compound according to claim 1 in the form of an individual stereoisomer or mixture thereof, a free compound and/or a physiologically acceptable salt and/or solvate thereof.

\* \* \* \* \*